United States Patent
Blaskowski et al.

(10) Patent No.: US 11,053,506 B2
(45) Date of Patent: *Jul. 6, 2021

(54) ITERATIVE GENOME EDITING IN MICROBES

(71) Applicant: Zymergen Inc., Emeryville, CA (US)

(72) Inventors: Stephen Blaskowski, Oakland, CA (US); Sara da Luz Areosa Cleto, Emeryville, CA (US); Cameron Coates, Oakland, CA (US); Aaron Miller, Berkeley, CA (US); Sharon Nademanee, Alameda, CA (US); Melissa Netwal, Oakland, CA (US); Kedar Patel, Fremont, CA (US); Shawn Szyjka, Martinez, CA (US); Philip Weyman, Alameda, CA (US); Solomon Henry Stonebloom, Alameda, CA (US); Colin Scott Maxwell, Emeryville, CA (US); Elizabeth Lauren Meier, Oakland, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/825,683

(22) Filed: Mar. 20, 2020

(65) Prior Publication Data
US 2020/0283780 A1    Sep. 10, 2020

Related U.S. Application Data

(63) Continuation of application No. PCT/US2020/021472, filed on Mar. 6, 2020.

(60) Provisional application No. 62/816,031, filed on Mar. 8, 2019.

(51) Int. Cl.
| | | |
|---|---|---|
| *C12N 15/70* | (2006.01) | |
| *C12N 15/113* | (2010.01) | |
| *C12N 9/22* | (2006.01) | |
| *C12N 15/81* | (2006.01) | |
| *C12N 15/77* | (2006.01) | |
| *C12N 15/80* | (2006.01) | |

(52) U.S. Cl.
CPC .............. *C12N 15/70* (2013.01); *C12N 9/22* (2013.01); *C12N 15/113* (2013.01); *C12N 15/77* (2013.01); *C12N 15/80* (2013.01); *C12N 15/81* (2013.01); *C12N 2310/20* (2017.05); *C12N 2800/10* (2013.01); *C12N 2800/80* (2013.01)

(58) Field of Classification Search
None
See application file for complete search history.

(56) References Cited

U.S. PATENT DOCUMENTS

| | | |
|---|---|---|
| 5,605,793 A | 2/1997 | Stemmer |
| 5,837,458 A | 11/1998 | Minshull et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,260,723 B2 | 2/2016 | Mali et al. |
| 9,580,701 B2 | 2/2017 | May et al. |
| 9,580,719 B2 | 2/2017 | Retallack et al. |
| 9,637,739 B2 | 5/2017 | Šikšnys et al. |
| 9,677,090 B2 | 6/2017 | Donohue et al. |
| 9,688,972 B2 | 6/2017 | May et al. |
| 9,738,687 B2 | 8/2017 | Guay et al. |
| 9,745,562 B2 | 8/2017 | Donohue et al. |
| 9,790,490 B2 | 10/2017 | Zhang et al. |
| 9,816,081 B1 | 11/2017 | Donohue et al. |
| 9,822,372 B2 | 11/2017 | Zhang et al. |
| 9,834,791 B2 | 12/2017 | Zhang et al. |
| 9,840,713 B2 | 12/2017 | Zhang |
| 9,896,696 B2 | 2/2018 | Begemann et al. |
| 9,970,011 B2 | 5/2018 | Duffield et al. |
| 9,982,279 B1 | 5/2018 | Gill et al. |
| 2014/0068797 A1 | 3/2014 | Doudna et al. |
| 2014/0248702 A1 | 9/2014 | Zhang et al. |
| 2015/0240261 A1 | 8/2015 | Siksnys et al. |
| 2015/0291961 A1 | 10/2015 | Siksnys et al. |
| 2016/0168592 A1 | 6/2016 | Church et al. |
| 2017/0369879 A1 | 12/2017 | Duffield et al. |
| 2020/0283802 A1 | 9/2020 | Blaskowski et al. |

FOREIGN PATENT DOCUMENTS

| | | | |
|---|---|---|---|
| WO | WO 2014/143381 A1 * | 9/2014 | ......... C12N 2310/20 |
| WO | WO 2017/100376 A2 | 6/2017 | |

(Continued)

OTHER PUBLICATIONS

Kuivanen et al., "Engineering Aspergillus niger for galactaric acid production: elimination of galactaric acid catabolism by using RNA sequencing and CRISPR/Cas9" 15 Microbial Cell Factories 210 1-9 (2016).*

(Continued)

*Primary Examiner* — Nancy J Leith
(74) *Attorney, Agent, or Firm* — Cooley LLP

(57) ABSTRACT

The present invention relates to methods for editing the genome of a microbial host cell in successive rounds of transformation. The method allows the introduction of genetic edits into the genome of a microbial host cell in an iterative fashion that does not require the use of functional counterselection following at least one round of transformation. It can be used to rapidly stack genetic edits in the genome of a microbial host cell. Kits for performing the methods are also disclosed.

27 Claims, 21 Drawing Sheets

(56) References Cited

FOREIGN PATENT DOCUMENTS

| WO | WO 2017/100377 A1 | 6/2017 |
|---|---|---|
| WO | WO 2017/191210 A1 | 11/2017 |
| WO | WO 2018/226880 A1 | 12/2018 |
| WO | WO 2018/226900 A2 | 12/2018 |
| WO | WO 2019/032926 A1 | 2/2019 |
| WO | WO 2020/185584 A1 | 9/2020 |
| WO | WO 2020/185590 A1 | 9/2020 |

OTHER PUBLICATIONS

Lauritsen et al., "A versatile one-step CRISPR-Cas9 based approach to plasmid-curing" 16 Microbial Cell Factories 135, 1-10 (Year: 2017).*
Becker and Guarente, "[12] High-efficiency transformation of yeast by electroporation." Methods in Enzymology (1991); 194: 182-187.
Crameri, et al., "DNA shuffling of a family of genes from diverse species accelerates directed evolution." Nature (Jan. 15, 1998); 391(6664): 288-291.
Crameri, et al., "Molecular evolution of an arsenate detoxification pathway by DNA shuffling." Nature Biotechnology (May 1997); 15(5): 436-438.
Datsenko and Wanner, "One-step inactivation of chromosomal genes in *Escherichia coli* K-12 using PCR products". PNAS (Jun. 6, 2000); 97(12): 6640-6645.
De Almeida, et al. "Transgenic expression of two marker genes under the control of an *Arabidopsis* rbcS promoter: Sequences encoding the Rubisco transit peptide increase expression levels." Molecular and General Genetics MGG (1989); 218(1): 78-86.
Gietz and Woods, "Transformation of yeast by lithium acetate/single-stranded carrier DNA/polyethylene glycol method". Methods in Enzymology (2002); 350: 87-96.
Gillings, M.R., "Integrons: Past, Present, and Future". Microbiol Mol Biol Rev. (Jun. 2014); 78(2): 257-277.
Ito, Hisao, et al., "Transformation of intact yeast cells treated with alkali cations." Journal of Bacteriology (1983); 153(1): 163-168.
Jiang, et al., "RNA-guided editing of bacterial genomes using CRISPR-Cas systems". Nature Biotechnology (2013); 31: 233-239.
Jones, Jonathan DG, et al., "High level expression of introduced chimaeric genes in regenerated transformed plants." The EMBO Journal (1985); 4(10): 2411-2418.
Khanna, et al., "Identification of the template binding polypeptide in the pea chloroplast transcriptional complex." Nucleic Acids Research (Jan. 11, 1992); 20(1): 69-74.
Moore, J.C., et al., "Strategies for the in vitro evolution of protein function: enzyme evolution by random recombination of improved sequences." Journal of Molecular Biology (Sep. 26, 1997); 272(3)3: 336-347.
Muyrers, et al., "Rapid modification of bacterial artificial chromosomes by ET-recombination". Nucleic Acids Research (Mar. 1, 1999); 27(6): 1555-1557.
Muyrers, et al., "Techniques: Recombinogenic engineering—new options for cloning and manipulating DNA". Trends Biochem Sci. (May 2001); 26(5): 325-331.

Nakashima and Miyazaki, "Bacterial cellular engineering by genome editing and gene silencing." International Journal of Molecular Sciences (Feb. 18, 2014); 15(2): 2773-2793.
Reyrat, et al., "Counterselectable markers: untapped tools for bacterial genetics and pathogenesis." Infection and Immunity (Sep. 1998); 66(9): 4011-4017.
Rivero-Müller, et al., "Assisted large fragment insertion by Red/ET-recombination (ALFIRE)—an alternative and enhanced method for large fragment recombineering". Nucleic Acids Res. (May 15, 2007); 35(10): e78. Epub May 21, 2007.
Sharan, et al., "Recombineering: A Homologous Recombination-Based Method of Genetic Engineering." Nature Protocols 2009; 4(2): 206-223.
Stemmer, W.P., "DNA shuffling by random fragmentation and reassembly: In vitro recombination for molecular evolution." Proceedings of the National Academy of Sciences (Oct. 25, 1994); 91(22): 10747-10751.
Stemmer, W.P., "Rapid evolution of a protein in vitro by DNA shuffling." Nature (Aug. 4, 1994); 370(6488): 389-391.
Tear, et al., "Excision of Unstable Artificial Gene-Specific Inverted Repeats Mediates Scar-Free Gene Deletions in *Escherichia coli*." Applied Biochemistry and Biotechnology (Feb. 2015); 175(4): 1858-1867. Epub Nov. 27, 2014.
Thomason, et al., "Recombineering: Genetic Engineering in Bacteria Using Homologous Recombination." Current Protocols in Molecular Biology (Apr. 14, 2014); 106:1.16:1-39.
Zhang, et al. "Directed evolution of a fucosidase from a galactosidase by DNA shuffling and screening." Proc Natl Acad Sci U S A. (1997); 94 (9): 4504-4509.
Zhang, Y., et al., "A new logic for DNA engineering using recombination in *Escherichia coli*". Nature Genetics (Oct. 1998); 20(2): 123-128.
Zhang, Y., et al., "DNA cloning by homologous recombination in *Escherichia coli*". Nature Biotechnology (Dec. 2000); 18(12): 1314-1317.
Ronda et al. "CRMAGE: CRISPR Optimized MAGE Recombineering". Scientific Reports (2016); vol. 6, Article number: 19452.
Reisch and Prather, "The no-SCAR (Scarless Cas9 Assisted Recombineering) system for genome editing in *Escherichia coli*". Scientific Reports (2015); vol. 5, Article No. 15096.
Datta et al. "A set of recombineering plasmids for gram-negative bacteria." Gene (Sep. 1, 2006); 379: 109-115. Epub May 4, 2006.
Garst et al. "Genome-wide mapping of mutations at single-nucleotide resolution for protein, metabolic and genome engineering." Nat Biotechnol. (2017); 35(1): 48-55.
Liu et al. "Iterative genome editing of *Escherichia coli* for 3-hydroxypropionic acid production". Metab Eng. (May 2018); 47: 303-313. Epub Apr. 14, 2018.
International Application No. PCT/US2020/021472, International Search Report and Written Opinion dated Aug. 12, 2020, 24 pages.
International Application No. PCT/US2020/021472, Invitation to Pay Additional Fees, dated May 29, 2020, 4 pages.
International Application No. PCT/US2020/021448, International Search Report and Written Opinion dated Jul. 23, 2020, 18 pages.
International Application No. PCT/US2020/021448, Invitation to Pay Additional Fees, dated May 29, 2020, 4 pages.

* cited by examiner

FIG. 2
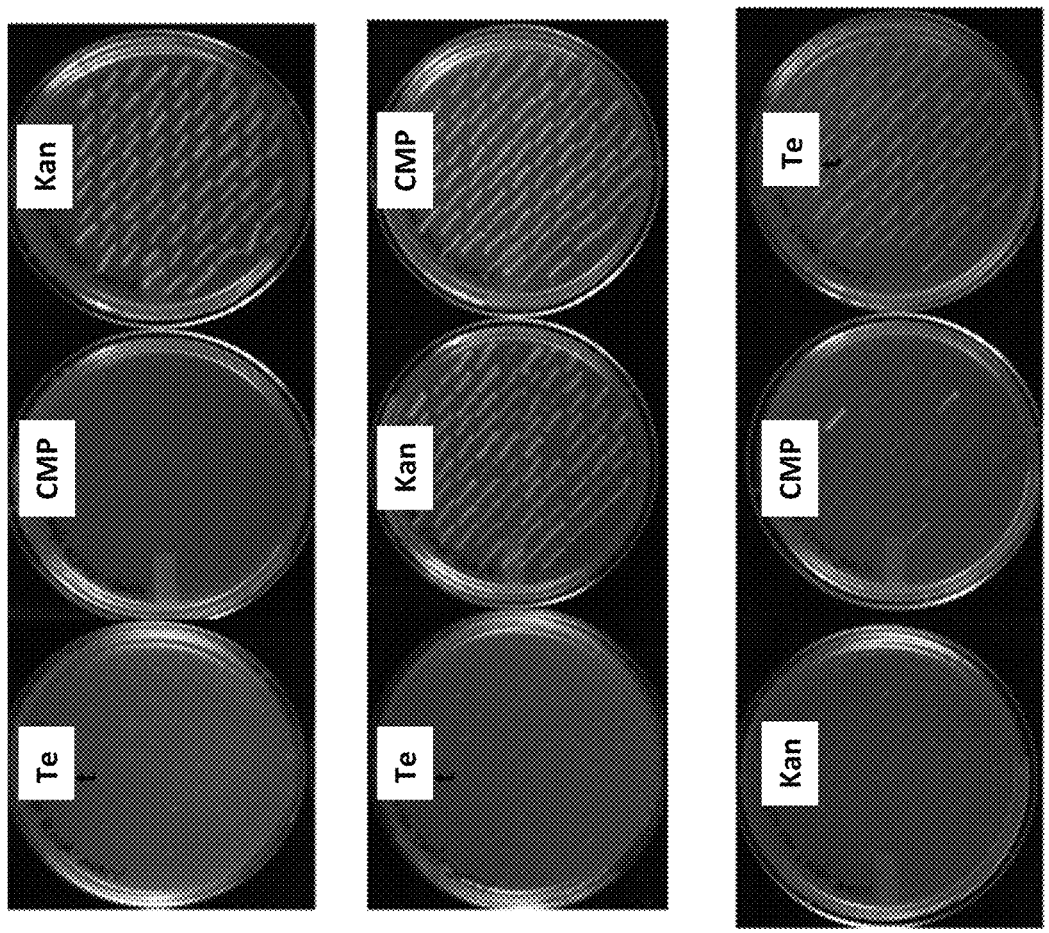
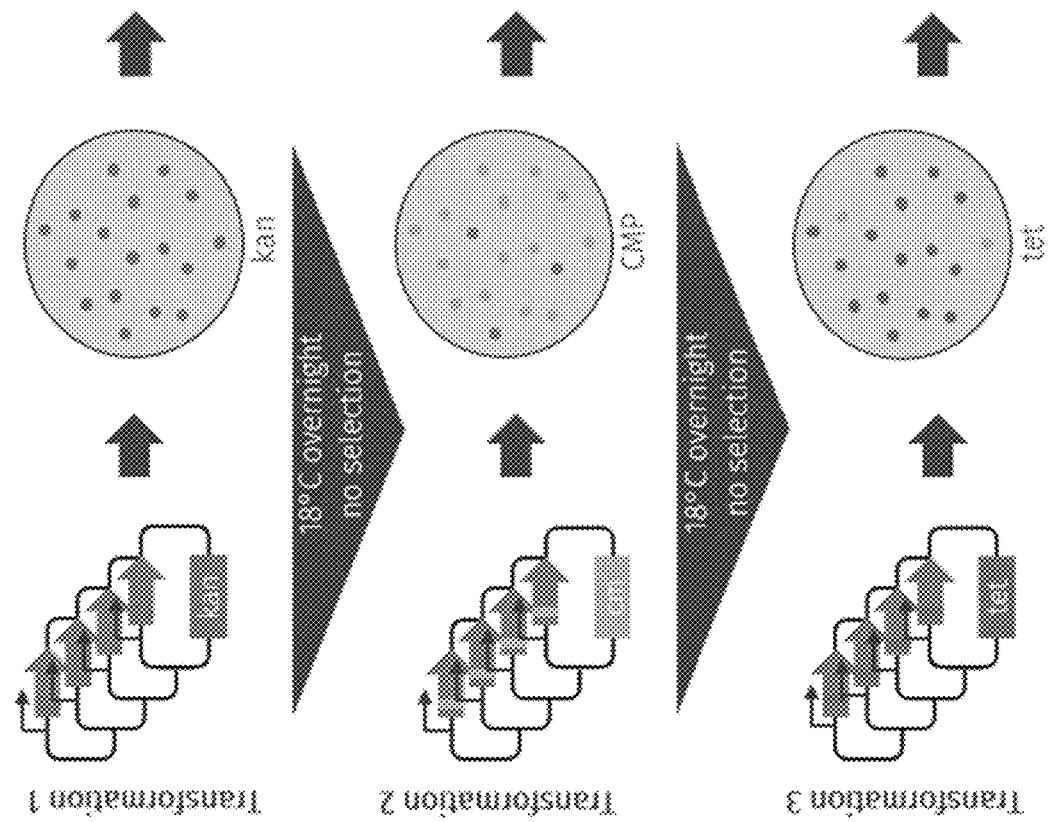

FIG. 5A
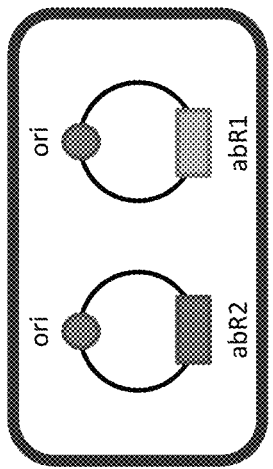
FIG. 5B
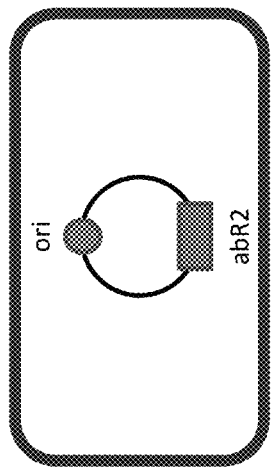
FIG. 5C
FIG. 5D

ITERATIVE GENOME EDITING IN MICROBES

CROSS-REFERENCE TO RELATED APPLICATIONS

This application is a Continuation of International PCT Application No. PCT/US2020/021472, filed Mar. 6, 2020, which claims the benefit of priority to U.S. Provisional Application Ser. No. 62/816,031, filed on Mar. 8, 2019, each of which is herein incorporated by reference in its entirety for all purposes.

FIELD

The present disclosure is directed to compositions and methods for iteratively editing a microbial host cell without requiring active expression and utilization of a counter-selectable marker in each round of editing. The disclosed methods and compositions can be useful for stacking multiple genetic edits in the genome of desired host cells or organisms.

BACKGROUND

Metabolic engineering is widely applied to modify microbial host cells such as *Escherichia coli* to produce industrially relevant biofuels or biochemicals, including ethanol, higher alcohols, fatty acids, amino acids, shikimate precursors, terpenoids, polyketides, and polymeric precursors of 1,4-butanediol. Often, industrially optimized strains require numerous genomic modifications, including insertions, deletions, and regulatory modifications in order to produce such industrially relevant products. Such large numbers of genome editing targets require efficient tools to perform time-saving sequential manipulations or multiplex manipulations.

While there are a number of approaches utilizing phage recombinase-mediated homologous recombination (recombineering) using either the Rac prophage system or the three bacteriophage λ Red proteins Exo, Beta, and Gam for manipulating the chromosomal DNA of *E. coli*, these approaches are often not ideal for high-throughput applications given that they can be laborious, time consuming, and/or feature mutagenesis efficiencies often below 1%. Recently, an approach that utilizes both phage recombinase-mediated homologous recombination and CRISPR/Cas9 technology was introduced by Jiang W et al., (see Jiang et al., RNA-guided editing of bacterial genomes using CRISPR-Cas systems. Nat Biotechnol. 2013 March; 31(3):233-9). Briefly, in the method of Jiang and co-workers, the strain to be modified is first genetically manipulated to express the Cas9 nuclease and the λ Red machinery, and subsequently the strain is co-transformed with (i) a plasmid (pCRISPR) encoding the guide RNA, which anneals with the chromosomal region to be modified and promotes a site-specific DNA cleavage by the Cas9, and (ii) a donor DNA (PCR-derived or chemically synthesized) partially homologous to the cleaved extremities, which promotes the repair of the double stranded break through λ Red-mediated recombination, thereby introducing the desired mutation. While the strategy of Jiang and co-workers reported mutation efficiencies as high as 65%, the method is still time consuming and requires the presence and use of counter-selectable markers in order to effectively cure host cells of plasmids introduced throughout the procedure.

Thus, there is a need in the art for new methods for introducing and iteratively stacking genetic edits in microbial host cells in an efficient, rapid, and cost-effective manner that can be utilized in a wide-range of microbial hosts. The compositions and methods provided herein address the aforementioned drawbacks inherent with current methods for metabolically engineering microbial host cells.

SUMMARY

In one aspect, provided herein is a method for iteratively editing a microbial host cell genome, the method comprising: a.) introducing into the microbial host cell a first plasmid comprising a first repair fragment and a selection marker gene, wherein the microbial host cell comprises a site-specific restriction enzyme or a sequence encoding a site-specific restriction enzyme is introduced into the microbial host cell along with the first plasmid, wherein the site-specific restriction enzyme targets a first locus in the genome of the microbial host cell, and wherein the first repair fragment comprises homology arms separated by a sequence for a genetic edit in or adjacent to a first locus in the genome of the microbial host cell, wherein the homology arms comprise sequence homologous to sequence that flanks the first locus in the genome of the microbial host cell; b.) growing the microbial host cells from step (a) in a media selective for microbial host cells expressing the selection marker gene and isolating microbial host cells from cultures derived therefrom; c.) growing the microbial host cells isolated in step (b) in media not selective for the selection marker gene and isolating microbial host cells from cultures derived therefrom; and d.) repeating steps (a)-(c) in one or more additional rounds in the microbial host cells isolated in step (c), wherein each of the one or more additional rounds comprises introducing an additional plasmid comprising an additional repair fragment, wherein the additional repair fragment comprises homology arms separated by a sequence for a genetic edit in or adjacent to a locus in the genome of the microbial host cell, wherein the homology arms comprise sequence homologous to sequence that flanks the locus in the genome of the microbial host cell, wherein the additional plasmid comprises a different selection marker gene than the selection marker gene introduced in a previous round of selection, and wherein the microbial host cell comprises a site-specific restriction enzyme or a sequence encoding a site-specific restriction enzyme is introduced into the microbial host cell along with the additional plasmid that targets the first locus or another locus in the genome of the microbial host cell, thereby iteratively editing the microbial host cell genome; wherein a counterselection is not performed after at least one round of editing. In some cases, the counterselection is not performed after every round of editing. In some cases, the counterselection is not performed after any round of editing. In some cases, the counterselection is not performed after at least one round, after every round, or after any round of editing. In some cases, the counterselection is an antibiotic, chemical, or temperature-based counterselection. In some cases, the first and the additional plasmids comprise an identical origin of replication to each other or additional plasmids previously introduced into the microbial host cell. In some cases, the selection marker gene comprises an antibiotic or auxotrophic selection marker gene. In some cases, each additional repair fragment comprises sequence for the same genetic edit as one or more of the genetic edits present on a previous repair fragment. In some cases, each additional repair fragment comprises sequence for a different genetic edit as one or more of the genetic edits present on a previous repair fragment. In some cases, a plurality of different first repair fragments are introduced, wherein each repair fragment in the plurality of first repair fragments comprises a sequence for a genetic edit in or adjacent to different loci. In some cases, a plurality of different additional repair fragments are introduced, wherein the plurality of additional repair fragments comprise a sequence for a genetic edit in or adjacent to different loci. In some cases, the site-specific restriction enzyme of step (a) cleaves a sequence at the first locus in the genome of the microbial host cell. In some cases, the site-specific restriction enzyme of step (d) cleaves a sequence at the locus targeted in each of the one or more additional rounds in the genome of the microbial host cell. In some cases, the site-specific restriction enzyme of step (a) and/or step (d) is selected from the group consisting of an RNA-guided DNA endonuclease, a meganuclease, a transcription activator-like effector nucleases (TALEN), and a zinc-finger nuclease (ZFN). In some cases, the site-specific restriction enzyme of step (a) and/or step (d) is encoded on a plasmid, encoded in the genome, translated from RNA, or introduced into the cell as protein. In some cases, the RNA-guided DNA endonuclease of step (a) cleaves a sequence at the first locus in the genome of the microbial host cell. In some cases, the RNA-guided DNA endonuclease of step (d) cleaves a sequence at the locus targeted in each of the one or more additional rounds in the genome of the microbial host cell. In some cases, the RNA-guided DNA endonuclease is selected from Cas9, Cas12a, Cas12b, Cas12c, Cas12d, Cas12e, Cas13a, Cas13b, Cas13c, Cpf1, and MAD7, or homologs, orthologs or paralogs thereof. In some cases, the genetic edit is selected from the group consisting of an insertion, a deletion, a single nucleotide polymorphism, a genome shuffling, a large scale deletion, a genomic edit, a plasmid edit, and multiple edits, or any combination thereof. In some cases, the additional repair fragment introduced in each of the one or more additional rounds target a different locus and are associated with a different selection marker gene from a previous round of editing. In some cases, the method further comprises step (e), wherein step (e) comprises introducing a final plasmid comprising a final repair fragment in a terminal round of repeating steps (a)-(c), wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a sequence for a different selection marker gene than the selection marker gene introduced in a previous round of selection, wherein the microbial host cell comprises a site-specific restriction enzyme or a sequence encoding a site-specific restriction enzyme is introduced into the microbial host cell along with the final plasmid that targets the final locus in the genome of the microbial host cell. In some cases, the final locus is a different locus from any locus edited previously. In some cases, the method further comprises a step (f), wherein step (f) comprises introducing a gRNA comprising a guide sequence complementary to a sequence present on or associated with the final repair fragment to facilitate removal of the final repair fragment following the terminal round via an RNA-guided DNA endonuclease. In some cases, the microbial host cell comprises a set of proteins from one or more heterologous recombination systems In some cases, the microbial host cell comprises a set of proteins from a heterologous recombination system selected from a lambda red recombination system, a RecET recombination system, a Red/ET recombination system, any homologs, orthologs or paralogs of proteins from a lambda red recombination system or a RecET recombination system, or any combination thereof. In some cases, the set of proteins from the lambda red recombination system comprise a beta protein, a gam protein, and an exo protein. In some cases, the set of proteins from the heterologous recombination system are introduced into the microbial host cell on a plasmid comprising genes encoding the set of proteins from the heterologous recombination system prior to step (a). In some cases, the set of proteins from the heterologous recombination system are stably expressed by the microbial host cell due to integration of genes encoding the set of proteins from the heterologous recombination system into the microbial host cell's genome. In some cases, the set of proteins from the heterologous recombination system are in an operon operably linked to an inducible promoter. In some cases, the inducible promoter is inducible by addition or depletion of a reagent or by a change in temperature. In some cases, the reagent is selected from the group consisting of arabinose, isopropyl beta-D-1-thiogalactopyranoside (IPTG), and tetracycline. In some cases, the introducing steps comprise transforming the microbial host cell. In some cases, the microbial host cell is a eukaryotic cell. In some cases, the microbial host cell is a yeast cell. In some cases, the yeast cell is *Saccharomyces cerevisiae*. In some cases, the microbial host cell is a filamentous fungus. In some cases, the filamentous fungus is *Aspergillus niger*. In some cases, the microbial host cell is a prokaryotic cell. In some cases, the prokaryotic host cell is *Escherichia coli* or *Corynebacterium glutamicum*.

In another aspect provided herein is a method for iteratively editing a microbial host cell genome, the method comprising: a.) introducing into the microbial host cell a first plasmid, a first guide RNA (gRNA) and a first repair fragment, wherein the gRNA comprises a sequence complementary to a first locus in the genome of the microbial host cell, wherein the first repair fragment comprises homology arms separated by a sequence for a genetic edit in or adjacent to a first locus in the genome of the microbial host cell, wherein the homology arms comprise sequence homologous to sequence that flanks the first locus in the genome of the microbial host cell, wherein the first plasmid comprises a selection marker gene and at least one or both of the gRNA and the repair fragment, and wherein: i. the microbial host cell comprises an RNA-guided DNA endonuclease; or ii. an RNA-guided DNA endonuclease is introduced into the microbial host cell along with the first plasmid; b.) growing the microbial host cells from step (a) in a media selective for microbial host cells expressing the selection marker gene and isolating microbial host cells from cultures derived therefrom; c.) growing the microbial host cells isolated in step (b) in media not selective for the selection marker gene and isolating microbial host cells from cultures derived therefrom; and d.) repeating steps (a)-(c) in one or more additional rounds in the microbial host cells isolated in step (c), wherein each of the one or more additional rounds comprises introducing an additional plasmid, an additional gRNA and an additional repair fragment, wherein the additional gRNA comprises sequence complementary to a locus in the genome of the microbial host cell, wherein the additional repair fragment homology arms separated by a sequence for a genetic edit in or adjacent to a locus in the genome of the microbial host cell, wherein the homology arms comprise sequence homologous to sequence that flanks the locus in the genome of the microbial host cell, wherein the additional plasmid comprises a different selection marker gene than the selection marker gene introduced in a previous round of selection, and wherein the additional plasmid comprises at least one or both of the additional gRNA and the additional repair fragment, thereby iteratively editing the microbial host cell genome; wherein a counterselection is not performed after at least one round of editing. In some cases, the counterselection is not performed after every round of editing. In some cases, the counterselection is not performed after every round of editing. In some cases, the counterselection is not performed after any round of editing. In some cases, the counterselection is not performed after at least one round, after every round, or after any round of editing. In some cases, the counterselection is an antibiotic, chemical, or temperature-based counterselection. In some cases, the first and the additional plasmids comprise an identical origin of replication to each other or additional plasmids previously introduced into the microbial host cell. In some cases, the selection marker gene comprises an antibiotic or auxotrophic selection marker gene. In some cases, each additional repair fragment comprises sequence for the same genetic edit as one or more of the genetic edits present on a previous repair fragment. In some cases, each additional repair fragment comprises sequence for a different genetic edit as one or more of the genetic edits present on a previous repair fragment. In some cases, a plurality of different first repair fragments are introduced, wherein each repair fragment in the plurality of first repair fragments comprises a sequence for a genetic edit in or adjacent to different loci. In some cases, a plurality of different additional repair fragments are introduced, wherein the plurality of additional repair fragments comprise a sequence for a genetic edit in or adjacent to different loci. In some cases, the RNA-guided DNA endonuclease cleaves a sequence at the first locus from step (a) in the genome of the microbial host cell and the locus from step (d) in the genome of the microbial host cell in each of the one or more additional rounds. In some cases, the RNA-guided DNA endonuclease is selected from Cas9, Cas12a, Cas12b, Cas12c, Cas12d, Cas12e, Cas13a, Cas13b, Cas13c, Cpf1, and MAD7, or homologs, orthologs or paralogs thereof. In some cases, the RNA-guided DNA endonuclease is encoded on a plasmid, encoded in the genome, translated from RNA, or introduced into the cell as protein. In some cases, the first plasmid comprises the first gRNA and the first repair fragment. In some cases, the additional plasmid comprises the additional gRNA and the additional repair fragment. In some cases, the first gRNA and/or the additional gRNA is provided as a linear fragment. In some cases, the first repair fragment and/or the additional repair fragment is/are provided as a linear fragment, and, optionally, wherein the first repair fragment and/or the additional repair fragment is provided as ssDNA or dsDNA. In some cases, the first gRNA and/or the additional gRNA comprise a CRISPR RNA (crRNA) and a trans-activating crRNA (tracrRNA). In some cases, the first gRNA and/or the additional gRNA is a single gRNA (sgRNA). In some cases, the genetic edit is selected from the group consisting of an insertion, a deletion, a single nucleotide polymorphism, a genome shuffling, a large scale deletion, a genomic edit, a plasmid edit, and multiple edits, or any combination thereof. In some cases, the additional repair fragment introduced in each of the one or more additional rounds target a different locus and are associated with a different selection marker gene from a previous round of editing. In some cases, the additional gRNA introduced in each of the one or more additional rounds target a different locus and are associated with a different antibiotic selection marker gene from a previous round of editing. In some cases, the method further comprises step (e), wherein step (e) comprises introducing a final plasmid, a final gRNA and a final repair fragment in a terminal round of repeating steps (a)-(c), wherein the final gRNA comprises a sequence complementary to a final locus in the genome of the microbial host cell, wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a different selection marker gene than the selection marker gene introduced in a previous round of selection, and wherein the final plasmid comprises at least one or both of the final gRNA and the final repair fragment. In some cases, the final locus is a different locus from any locus edited previously. In some cases, the final locus is a different locus from any locus targeted by a gRNA previously introduced into the microbial host cell. In some cases, the method further comprises a step (f), wherein step (f) comprises introducing a gRNA comprising a guide sequence complementary to a sequence present on or associated with the final repair fragment to facilitate removal of the final repair fragment following the terminal round via an RNA guided DNA endonuclease. In some cases, the microbial host cell comprises a set of proteins from one or more heterologous recombination systems. In some cases, the microbial host cell comprises a set of proteins from a heterologous recombination system selected from a lambda red recombination system, a RecET recombination system, a Red/ET recombination system, any homologs, orthologs or paralogs of proteins from a lambda red recombination system or a RecET recombination system, or any combination thereof. In some cases, the set of proteins from the lambda red recombination system comprise a beta protein, a gam protein, and an exo protein. In some cases, the set of proteins from the heterologous recombination system are introduced into the microbial host cell on a plasmid comprising genes encoding the set of proteins from the heterologous recombination system prior to step (a). In some cases, the set of proteins from the heterologous recombination system are stably expressed by the microbial host cell due to integration of genes encoding the set of proteins from the heterologous recombination system into the microbial host cell's genome. In some cases, the set of proteins from the heterologous recombination system are in an operon operably linked to an inducible promoter. In some cases, the inducible promoter is inducible by addition or depletion of a reagent or by a change in temperature. In some cases, the reagent is selected from the group consisting of arabinose, isopropyl beta-D-1-thiogalactopyranoside (IPTG), and tetracycline. In some cases, the introducing steps comprise transforming the microbial host cell. In some cases, the microbial host cell is a eukaryotic cell. In some cases, the microbial host cell is a yeast cell. In some cases, the yeast cell is *Saccharomyces cerevisiae*. In some cases, the microbial host cell is a filamentous fungus. In some cases, the filamentous fungus is *Aspergillus niger*. In some cases, the microbial host cell is a prokaryotic cell. In some cases, the prokaryotic host cell is *Escherichia coli* or *Corynebacterium glutamicum*. In some cases, the method further comprises genotyping microbial host cells grown in a media selective for microbial host cells expressing a selection marker gene or in a media not selective for a selection marker gene.

In yet another aspect, provided herein is a method for iteratively editing a microbial host cell genome, the method comprising: a.) introducing into the microbial host cell a first plasmid comprising a first repair fragment and a selection marker gene, wherein the first repair fragment comprises homology arms separated by a sequence for a genetic edit in or adjacent to a first locus in the genome of the microbial host cell, wherein the homology arms comprise sequence homologous to sequence that flanks the first locus in the genome of the microbial host cell; b.) growing the microbial host cells from step (a) in a media selective for microbial host cells expressing the selection marker gene and isolating microbial host cells from cultures derived therefrom; c.) growing the microbial host cells isolated in step (b) in media not selective for the selection marker gene and isolating microbial host cells from cultures derived therefrom; and d.) repeating steps (a)-(c) in one or more additional rounds in the microbial host cells isolated in step (c), wherein each of the one or more additional rounds comprises introducing an additional plasmid comprising an additional repair fragment, wherein the additional repair fragment comprises homology arms separated by sequence for a genetic edit in or adjacent to a locus in the genome of the microbial host cell, wherein the homology arms comprise sequence homologous to sequence that flanks the locus in the genome of the microbial host cell, and wherein the additional plasmid comprises a different selection marker gene than the selection marker gene introduced in a previous round of selection, thereby iteratively editing the microbial host cell genome; wherein a counterselection is not performed after at least one round of editing. In some cases, the counterselection is not performed after every round of editing. In some cases, the counterselection is not performed after any round of editing. In some cases, the counterselection is not performed after at least one round, after every round, or after any round of editing. In some cases, the counterselection is an antibiotic, chemical, or temperature-based counterselection. In some cases, the first and the additional plasmids comprise an identical origin of replication to each other or additional plasmids previously introduced into the microbial host cell. In some cases, the selection marker gene comprises an antibiotic or auxotrophic selection marker gene. In some cases, each additional repair fragment comprises sequence for the same genetic edit as one or more of the genetic edits present on a previous repair fragment. In some cases, each additional repair fragment comprises sequence for a different genetic edit as one or more of the genetic edits present on a previous repair fragment. In some cases, a plurality of different first repair fragments are introduced, wherein each repair fragment in the plurality of first repair fragments comprises a sequence for a genetic edit in or adjacent to different loci. In some cases, a plurality of different additional repair fragments are introduced, wherein the plurality of additional repair fragments comprise a sequence for a genetic edit in or adjacent to different loci. In some cases, the genetic edit is selected from the group consisting of an insertion, a deletion, a single nucleotide polymorphism, a genome shuffling, a large scale deletion, a genomic edit, a plasmid edit, and multiple edits, or any combination thereof. In some cases, the additional repair fragment introduced in each of the one or more additional rounds target a different locus and are associated with a different selection marker gene from a previous round of editing. In some cases, the method further comprises step (e), wherein step (e) comprises introducing a final plasmid comprising a final repair fragment in a terminal round of repeating steps (a)-(c), wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a different selection marker gene than the selection marker gene introduced in a previous round of selection. In some cases, the final locus is a different locus from any locus edited previously. In some cases, the method further comprises a step (f), wherein step (f) comprises introducing a gRNA comprising a guide sequence complementary to a sequence present on or associated with the final repair fragment to facilitate removal of the final repair fragment following the terminal round via an RNA guided DNA endonuclease. In some cases, the microbial host cell comprises a set of proteins from one or more heterologous recombination systems. In some cases, the microbial host cell comprises a set of proteins from a heterologous recombination system selected from a lambda red recombination system, a RecET recombination system, a Red/ET recombination system, any homologs, orthologs or paralogs of proteins from a lambda red recombination system or a RecET recombination system, or any combination thereof.

In some cases, the set of proteins from the lambda red recombination system comprise a beta protein, a gam protein, and an exo protein. In some cases, the set of proteins from the heterologous recombination system are introduced into the microbial host cell on a plasmid comprising genes encoding the set of proteins from the heterologous recombination system prior to step (a). In some cases, the set of proteins from the heterologous recombination system are stably expressed by the microbial host cell due to integration of genes encoding the set of proteins from the heterologous recombination system into the microbial host cell's genome. In some cases, the set of proteins from the heterologous recombination system are in an operon operably linked to an inducible promoter. In some cases, the inducible promoter is inducible by addition or depletion of a reagent or by a change in temperature. In some cases, the reagent is selected from the group consisting of arabinose, isopropyl beta-D-1-thiogalactopyranoside (IPTG), and tetracycline. In some cases, the introducing steps comprise transforming the microbial host cell. In some cases, the microbial host cell is a eukaryotic cell. In some cases, the microbial host cell is a yeast cell. In some cases, the yeast cell is *Saccharomyces cerevisiae*. In some cases, the microbial host cell is a filamentous fungus. In some cases, the filamentous fungus is *Aspergillus niger*. In some cases, the microbial host cell is a prokaryotic cell. In some cases, the prokaryotic host cell is *Escherichia coli* or *Corynebacterium glutamicum*. In some cases, the method further comprises genotyping microbial host cells grown in a media selective for microbial host cells expressing a selection marker gene or in a media not selective for a selection marker gene.

In a still further aspect, provided herein is a method for clearing a previously present plasmid from a microbial host cell, the method comprising: a.) introducing into the microbial host cell comprising a previously present plasmid a first plasmid comprising a first selection marker gene; and b.) growing the microbial host cells from step (a) in a media selective for microbial host cells expressing the selection marker gene and isolating microbial host cells from cultures derived therefrom, wherein the previously present and the introduced first plasmids comprise an identical origin of replication, thereby clearing the previously present plasmid from a microbial host cell; wherein a counterselection is not performed to facilitate clearance of a previously present plasmid. In some cases, the method further comprises step (c), comprising growing the microbial host cells isolated in step (b) in media not selective for the selection marker gene and isolating microbial host cells from cultures derived therefrom. In some cases, the method further comprises repeating steps (a)-(c) in one or more rounds, wherein each of the one or more rounds comprises introducing an additional plasmid comprising a different selection marker gene than the selection marker gene introduced in a previous round of selection, wherein the previously present and additionally introduced plasmids comprise an identical origin of replication. In some cases, the previously present plasmid is a native plasmid or a heterologous plasmid. In some cases, the counterselection is not performed after at least one round, after every round, or after any round of editing. In some cases, the counterselection is an antibiotic, chemical, or temperature-based counterselection, and the counterselection is not performed after at least one round, after every round, or after any round of editing. In some cases, the selection marker gene comprises an antibiotic or auxotrophic selection marker gene. In some cases, the introducing steps comprise transforming the microbial host cell. In some cases, the microbial host cell is a eukaryotic cell. In some cases, wherein the microbial host cell is a yeast cell. In some cases, the yeast cell is *Saccharomyces cerevisiae*. In some cases, the microbial host cell is a filamentous fungus. In some cases, the filamentous fungus is *Aspergillus niger*. In some cases, the microbial host cell is a prokaryotic cell. In some cases, the prokaryotic host cell is *Escherichia coli* or *Corynebacterium glutamicum*. In some cases, the method further comprises genotyping microbial host cells grown in a media selective for microbial host cells expressing a selection marker gene or in a media not selective for a selection marker gene.

In a further aspect, provided herein is a method for iteratively clearing a previously introduced plasmid from a microbial host cell, the method comprising: a.) introducing into the microbial host cell a first plasmid comprising a first selection marker gene; b.) growing the microbial host cells from step (a) in a media selective for microbial host cells expressing the selection marker gene and isolating microbial host cells from cultures derived therefrom; c.) growing the microbial host cells isolated in step (b) in media not selective for the selection marker gene and isolating microbial host cells from cultures derived therefrom; and d.) repeating steps (a)-(c) in one or more rounds, wherein each of the one or more rounds comprises introducing an additional plasmid comprising a different selection marker gene than the selection marker gene introduced in a previous round of selection, and wherein the first and the additional plasmids comprise an identical origin of replication to each other first or additional plasmid previously introduced into the microbial host cell, thereby iteratively clearing the previously introduced first or additional plasmid from a microbial host cell; wherein a counterselection is not performed to facilitate clearance of a previously introduced plasmid. In some cases, the counterselection is not performed after at least one round, after every round, or after any round of editing. In some cases, the counterselection is an antibiotic, chemical, or temperature-based counterselection, and the counterselection is not performed after at least one round, after every round, or after any round of editing. In some cases, the selection marker gene comprises an antibiotic or auxotrophic selection marker gene. In some cases, the introducing steps comprise transforming the microbial host cell. In some cases, the microbial host cell is a eukaryotic cell. In some cases, the microbial host cell is a yeast cell. In some cases, the yeast cell is *Saccharomyces cerevisiae*. In some cases, the microbial host cell is a filamentous fungus. In some cases, the filamentous fungus is *Aspergillus niger*. In some cases, the microbial host cell is a prokaryotic cell. In some cases, the prokaryotic host cell is *Escherichia coli* or *Corynebacterium glutamicum*. In some cases, the method further comprises genotyping microbial host cells grown in a media selective for microbial host cells expressing a selection marker gene or in a media not selective for a selection marker gene.

In one aspect, provided herein is a method for generating a library of genetically edited microbial strains, the method comprising: (a) introducing a selection marker gene and a first genetic edit into the genome of each individual microbial host cell from a plurality of microbial host cells, wherein the first genetic edit introduced into the genome of each individual microbial host cell from the plurality of microbial host cells is different than the first genetic edit introduced into the genome of each other individual microbial host cell from the plurality of microbial host cells; (b) clearing the selection marker gene from each of the individual microbial host cells from step (a) to generate individual microbial host cells comprising a first genetic edit that is cleared of the selectable marker gene; (c) mixing each of the individual microbial host cells from step (b) to form a main culture; (d) dividing the main culture of step (c) into separate microbial host cell cultures; and (e) repeating steps (a)-(d) for one or more additional rounds, wherein each of the one or more additional rounds comprises introducing a different selection marker gene than the selection marker gene introduced in a previous round of selection and a different genetic edit than the first genetic edit introduced in a previous round, thereby generating a library of genetically edited microbial strains. In some cases, the introducing the selectable marker gene and the first genetic edit in step (a) comprises introducing into the individual microbial host cell a first plasmid comprising a first repair fragment and the selection marker gene, wherein the individual microbial host cell comprises a site-specific restriction enzyme or a sequence encoding a site-specific restriction enzyme is introduced into the individual microbial host cell along with the first plasmid, wherein the site-specific restriction enzyme targets a first locus in the genome of the individual microbial host cell, and wherein the first repair fragment comprises homology arms separated by a sequence for the first genetic edit in or adjacent to the first locus in the genome of the individual microbial host cell, wherein the homology arms comprise sequence homologous to sequence that flanks the first locus in the genome of the individual microbial host cell. In some cases, the one or more additional rounds of step (e) comprises introducing into each individual microbial host cell from the main culture of step (c) an additional plasmid comprising an additional repair fragment, wherein the additional repair fragment comprises homology arms separated by a sequence for a genetic edit in or adjacent to a locus in the genome of the microbial host cell, wherein the homology arms comprise sequence homologous to sequence that flanks the locus in the genome of the microbial host cell, wherein the additional plasmid comprises a different selection marker gene than the selection marker gene introduced in a previous round of selection, and wherein the microbial host cell comprises a site-specific restriction enzyme or a sequence encoding a site-specific restriction enzyme is introduced into the microbial host cell along with the additional plasmid that targets the first locus or another locus in the genome of the microbial host cell. In some cases, the introducing the selectable marker gene and first genetic edit comprises introducing into the individual microbial host cell a first plasmid comprising a first repair fragment and the selection marker gene, wherein the first repair fragment comprises homology arms separated by a sequence for the first genetic edit in or adjacent to a first locus in the genome of the individual microbial host cell, wherein the homology arms comprise sequence homologous to sequence that flanks the first locus in the genome of the individual microbial host cell. In some cases, the one or more additional rounds of step (e) comprises introducing into each individual microbial host cell from the main culture of step (c) an additional plasmid comprising an additional repair fragment, wherein the additional repair fragment comprises homology arms separated by sequence for a genetic edit in or adjacent to a locus in the genome of the microbial host cell, wherein the homology arms comprise sequence homologous to sequence that flanks the locus in the genome of the microbial host cell, and wherein the additional plasmid comprises a different selection marker gene than the selection marker gene introduced in a previous round of selection. In some cases, the introducing the selectable marker gene and first genetic edit comprises introducing into the individual microbial host cell a first plasmid, a first guide RNA (gRNA) and a first repair fragment, wherein the gRNA comprises a sequence complementary to a first locus in the genome of the individual microbial host cell, wherein the first repair fragment comprises homology arms separated by a sequence for the first genetic edit in or adjacent to a first locus in the genome of the individual microbial host cell, wherein the homology arms comprise sequence homologous to sequence that flanks the first locus in the genome of the individual microbial host cell, wherein the first plasmid comprises the selection marker gene and at least one or both of the gRNA and the repair fragment, and wherein: (i) the individual microbial host cell comprises an RNA-guided DNA endonuclease; or (ii) an RNA-guided DNA endonuclease is introduced into the individual microbial host cell along with the first plasmid. In some cases, the one or more additional rounds of step (e) comprises introducing into each individual microbial host cell from the main culture of step (c) an additional plasmid, an additional gRNA and an additional repair fragment, wherein the additional gRNA comprises sequence complementary to a locus in the genome of the microbial host cell, wherein the additional repair fragment homology arms separated by a sequence for a genetic edit in or adjacent to a locus in the genome of the microbial host cell, wherein the homology arms comprise sequence homologous to sequence that flanks the locus in the genome of the microbial host cell, wherein the additional plasmid comprises a different selection marker gene than the selection marker gene introduced in a previous round of selection, and wherein the additional plasmid comprises at least one or both of the additional gRNA and the additional repair fragment. In some cases, the clearing the selection marker gene comprises: (a) growing the individual microbial host cells from step in a media selective for individual microbial host cells expressing the selection marker gene and isolating microbial host cells from cultures derived therefrom; and (b) growing the microbial host cells isolated in step (a) in media not selective for the selection marker gene and isolating microbial host cells from cultures derived therefrom. In some cases, a counterselection is not performed after at least one round of editing to facilitate clearance of a previously introduced selection marker gene. In some cases, the counterselection is not performed after every round of editing. In some cases, the counterselection is not performed after any round of editing. In some cases, the counterselection is not performed after at least one round, after every round, or after any round of editing. In some cases, the counterselection is an antibiotic, chemical, or temperature-based counterselection. In some cases, the first and the additional plasmids, comprise an identical origin of replication to each other or additional plasmids previously introduced into the microbial host cell. In some cases, the selection marker gene comprises an antibiotic or auxotrophic selection marker gene. In some cases, each additional repair fragment comprises sequence for the same genetic edit as one or more of the genetic edits present on a previous repair fragment. In some cases, each additional repair fragment comprises sequence for a different genetic edit as one or more of the genetic edits present on a previous repair fragment. In some cases, the site-specific restriction enzyme cleaves a sequence at the first locus in the genome of the microbial host cell. In some cases, the site-specific restriction enzyme cleaves a sequence at the locus targeted in each of the one or more additional rounds in the genome of the microbial host cell. In some cases, the site-specific restriction enzyme is selected from the group consisting of an RNA-guided DNA endonuclease, a meganuclease, a transcription activator-like effector nucleases (TALEN), and a zinc-finger nuclease (ZFN). In some cases, the site-specific restriction enzyme is selected from the group consisting of an RNA-guided DNA endonuclease, a meganuclease, a transcription activator-like effector nucleases (TALEN), and a zinc-finger nuclease (ZFN). In some cases, the site-specific restriction enzyme is encoded on a plasmid, encoded in the genome, translated from RNA, or introduced into the cell as protein. In some cases, the site-specific restriction enzyme is encoded on a plasmid, encoded in the genome, translated from RNA, or introduced into the cell as protein. In some cases, the RNA-guided DNA endonuclease cleaves a sequence at the first locus in the genome of the microbial host cell. In some cases, the RNA-guided DNA endonuclease cleaves a sequence at the locus targeted in each of the one or more additional rounds in the genome of the microbial host cell. In some cases, the RNA-guided DNA endonuclease cleaves a sequence at the first locus in the genome of the microbial host cell and the locus in the genome of the microbial host cell in each of the one or more additional rounds. In some cases, the RNA-guided DNA endonuclease is selected from Cas9, Cas12a, Cas12b, Cas12c, Cas12d, Cas12e, Cas13a, Cas13b, Cas13c, Cpf1, and MAD7, or homologs, orthologs or paralogs thereof. In some cases, the RNA-guided DNA endonuclease is encoded on a plasmid, encoded in the genome, translated from RNA, or introduced into the cell as protein. In some cases, the first plasmid comprises the first gRNA and the first repair fragment. In some cases, the additional plasmid comprises the additional gRNA and the additional repair fragment. In some cases, the first gRNA and/or the additional gRNA is provided as a linear fragment. In some cases, the first repair fragment and/or the additional repair fragment is/are provided as a linear fragment, and, optionally, wherein the first repair fragment and/or the additional repair fragment is provided as ssDNA or dsDNA. In some cases, the first gRNA and/or the additional gRNA comprise a CRISPR RNA (crRNA) and a trans-activating crRNA (tracrRNA). In some cases, the first gRNA and/or the additional gRNA is a single gRNA (sgRNA). In some cases, the genetic edit is selected from the group consisting of an insertion, a deletion, a single nucleotide polymorphism, a genome shuffling, a large scale deletion, a genomic edit, a plasmid edit, and multiple edits, or any combination thereof. In some cases, the additional repair fragment introduced in each of the one or more additional rounds target a different locus and are associated with a different selection marker gene from a previous round of editing. In some cases, the additional gRNA introduced in each of the one or more additional rounds target a different locus and are associated with a different antibiotic selection marker gene from a previous round of editing. In some cases, the method further comprises step (f), wherein step (f) comprises introducing a final plasmid comprising a final repair fragment in a terminal round of repeating steps (a)-(d), wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a sequence for a different selection marker gene than the selection marker gene introduced in a previous round of selection, wherein the microbial host cell comprises a site-specific restriction enzyme or a sequence encoding a site-specific restriction enzyme is introduced into the microbial host cell along with the final plasmid that targets the final locus in the genome of the microbial host cell. In some cases, the method further comprises step (f), wherein step (f) comprises introducing a final plasmid, a final gRNA and a final repair fragment in a terminal round of repeating steps (a)-(d), wherein the final gRNA comprises a sequence complementary to a final locus in the genome of the microbial host cell, wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a different selection marker gene than the selection marker gene introduced in a previous round of selection, and wherein the final plasmid comprises at least one or both of the final gRNA and the final repair fragment. In some cases, the method further comprises step (f), wherein step (f) comprises introducing a final plasmid comprising a final repair fragment in a terminal round of repeating steps (a)-(d), wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a different selection marker gene than the selection marker gene introduced in a previous round of selection. In some cases, the final locus is a different locus from any locus edited previously. In some cases, the final locus is a different locus from any locus targeted by a gRNA previously introduced into the microbial host cell. In some cases, the method further comprises a step (f), wherein step (f) comprises introducing a gRNA comprising a guide sequence complementary to a sequence present on or associated with the final repair fragment to facilitate removal of the final repair fragment following the terminal round via an RNA-guided DNA endonuclease. In some cases, each individual microbial host cell comprises a set of proteins from one or more heterologous recombination systems. In some cases, each individual microbial host cell comprises a set of proteins from a heterologous recombination system selected from a lambda red recombination system, a RecET recombination system, a Red/ET recombination system, any homologs, orthologs or paralogs of proteins from a lambda red recombination system or a RecET recombination system, or any combination thereof. In some cases, the set of proteins from the lambda red recombination system comprise a beta protein, a gam protein, and an exo protein. In some cases, the set of proteins from the heterologous recombination system are introduced into each individual microbial host cell on a plasmid comprising genes encoding the set of proteins from the heterologous recombination system prior to step (a). In some cases, the set of proteins from the heterologous recombination system are stably expressed by each individual microbial host cell due to integration of genes encoding the set of proteins from the heterologous recombination system into the microbial host cell's genome. In some cases, the set of proteins from the heterologous recombination system are in an operon operably linked to an inducible promoter. In some cases, the inducible promoter is inducible by addition or depletion of a reagent or by a change in temperature. In some cases, the reagent is selected from the group consisting of arabinose, isopropyl beta-D-1-thiogalactopyranoside (IPTG), and tetracycline. In some cases, the introducing steps comprise transforming each individual microbial host cell. In some cases, each individual microbial host cell is a eukaryotic cell. In some cases, each individual microbial host cell is a yeast cell. In some cases, the yeast cell is *Saccharomyces cerevisiae*. In some cases, the microbial host cell is a filamentous fungus. In some cases, the filamentous fungus is *Aspergillus niger*. In some cases, each individual microbial host cell is a prokaryotic cell. In some cases, the prokaryotic host cell is *Escherichia coli* or *Corynebacterium glutamicum*.

BRIEF DESCRIPTION OF THE FIGURES

FIG. 2 illustrates the loss of selectable markers as a function of transformation.

FIGS. 5A-5D illustrates an example of the clearance of a previously present plasmid from a strain via transformation and selection for a second plasmid. FIG. 5A shows a cell containing a plasmid with an antibiotic resistance marker (abR1) is transformed with a second plasmid that has the same origin of replication (circle) and a different antibiotic selection marker (abR2). FIG. 5B shows selection for transformants containing the second plasmid is performed by plating on media containing the antibiotic for the second marker, resulting in a cell that contains both plasmids.

FIG. 5C shows growth under selection for the second plasmid results in the loss of the first plasmid. FIG. 5D shows an optional final step involves loss of the second plasmid either by active counterselection or by relief from antibiotic selection to result in a final strain free of plasmids.

FIG. 7A depicts CRISPR/Cas9 mediated transformations performed by introducing three (3) classes of linear DNA molecules: a plasmid backbone encoding a Cas9 expression gene and an antibiotic (i.e., Nourseothricin) resistance marker gene, an sgRNA expression cassette with homology for integration into the Cas9 expression plasmid, and multiple edit payloads for the genomic locus targeted by the sgRNA. FIG. 7B shows genotyping data from six (6) transformation experiments introducing a pool of 3 payloads for insertion into each of six (6) possible genomic loci (i.e., ARI1 gene, TRP1 gene, ADH6 gene, ECM13 gene, MCH5 gene or PRB1 gene) targeted by an sgRNA targeting one of the six (6) loci in the *S. cerevisiae* genome. In each experiment, multiple genotypes were recovered following pooled genome editing.

FIG. 8A depicts the rapid iterative transformation process: following a standard transformation process, transformants are selected on antibiotic media. Colonies are cultured as a pool then transformed a second time with an alternate plasmid backbone containing antibiotic marker 2 and transformants are selected on solid media containing antibiotic 2. This process is repeated with antibiotic 3 to produce strains with 3 edits. FIG. 8B shows CRISPR/Cas9 mediated transformation performed by transformation with 3 linear DNA molecules: a plasmid backbone encoding a Cas9 expression gene and one of three antibiotic markers, an sgRNA expression cassette with homology for integration into the Cas9 expression plasmid, and a repair template for the genomic locus targeted by the sgRNA. FIG. 8C shows results from genotyping of two genomic edits introduced by rapidly iterated transformations following a traditional transformation. 17.8% of 28 colonies genotyped contained both iterated edits.

FIG. 9A illustrates the process for conducting pooled plasmid iterative stacking (PPIS), while

FIG. 10A illustrates the process for conducting pooled parent iterative stacking (PPAIS), while

DETAILED DESCRIPTION

Definitions

Figure 1:
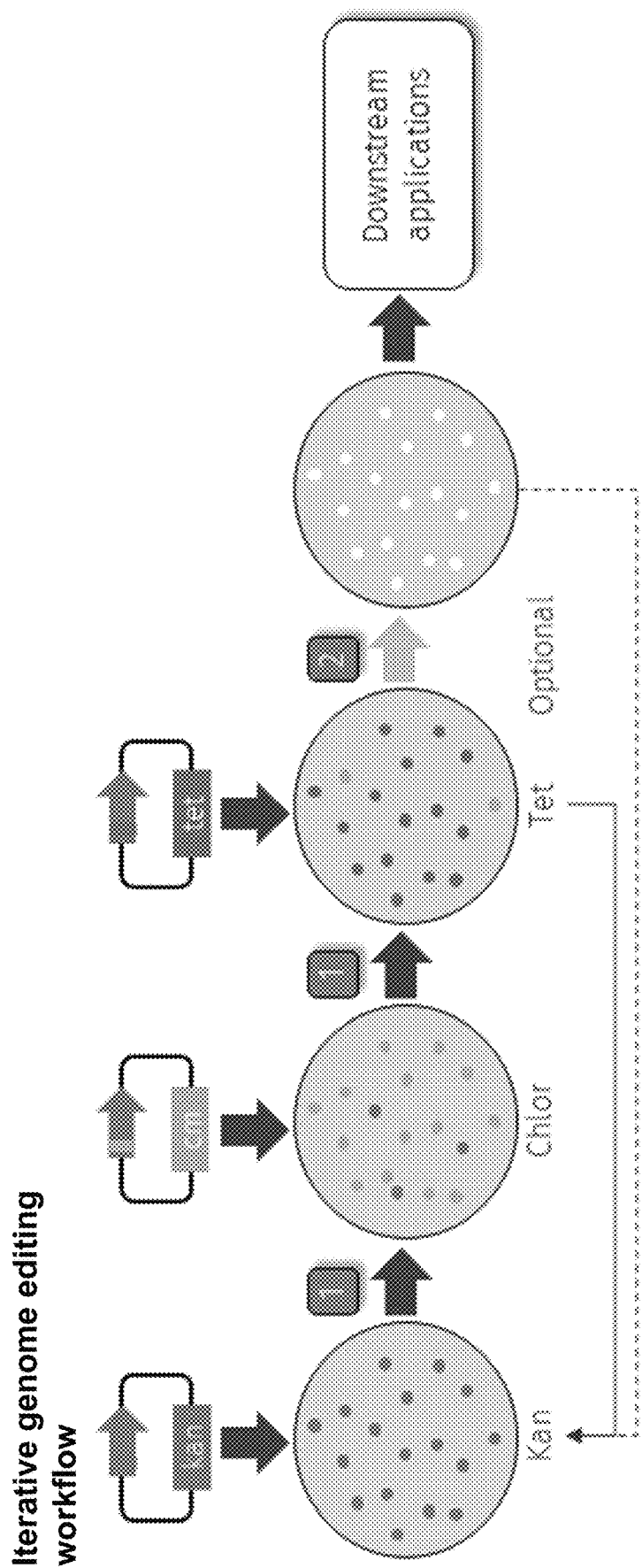
FIG. 1 depicts a workflow schematic for an embodiment of iterative genomic editing as provided herein and detailed in Example 1.

While the following terms are believed to be well understood by one of ordinary skill in the art, the following definitions are set forth to facilitate explanation of the presently disclosed subject matter.

As used herein, the term "a" or "an" can refer to one or more of that entity, i.e. can refer to a plural referents. As such, the terms "a" or "an", "one or more" and "at least one" can be used interchangeably herein. In addition, reference to "an element" by the indefinite article "a" or "an" does not exclude the possibility that more than one of the elements is present, unless the context clearly requires that there is one and only one of the elements.

Unless the context requires otherwise, throughout the present specification and claims, the word "comprise" and variations thereof, such as, "comprises" and "comprising" are to be construed in an open, inclusive sense that is as "including, but not limited to".

Reference throughout this specification to "one embodiment" or "an embodiment" means that a particular feature, structure or characteristic described in connection with the embodiment may be included in at least one embodiment of the present disclosure. Thus, the appearances of the phrases "in one embodiment" or "in an embodiment" in various places throughout this specification may not necessarily all referring to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

As used herein, the terms "cellular organism" "microorganism" or "microbe" should be taken broadly. These terms are used interchangeably and include, but are not limited to, the two prokaryotic domains, Bacteria and Archaea, as well as certain eukaryotic fungi and protists. In some embodiments, the disclosure refers to the "microorganisms" or "cellular organisms" or "microbes" of lists/tables and figures present in the disclosure. This characterization can refer to not only the identified taxonomic genera provided herein, but also the identified taxonomic species, as well as the various novel and newly identified or designed strains of any organism provided herein.

As used herein, the term "prokaryotes" is art recognized and refers to cells that contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

As used herein, the term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) *thermophilus* (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

As used herein, "bacteria" or "eubacteria" can refer to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

As used herein, a "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

As used herein, the terms "genetically modified host cell," "recombinant host cell," and "recombinant strain" are used interchangeably herein and can refer to host cells that have been genetically modified by the iterative genetic editing methods provided herein. Thus, the terms include a host cell (e.g., bacteria, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell.

As used herein, the term "wild-type microorganism" or "wild-type host cell" can describe a cell that occurs in nature, i.e. a cell that has not been genetically modified.

As used herein, the term "genetically engineered" may refer to any manipulation of a host cell's genome (e.g. by insertion, deletion, mutation, or replacement of nucleic acids).

As used herein, the term "control" or "control host cell" can refer to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell. In some embodiments, the present disclosure teaches the use of parent strains as control host cells. In other embodiments, a host cell may be a genetically identical cell that lacks a specific promoter or SNP being tested in the treatment host cell.

As used herein, the term "allele(s)" can mean any of one or more alternative forms of a gene, all of which alleles relate to at least one trait or characteristic. In a diploid cell, the two alleles of a given gene occupy corresponding loci on a pair of homologous chromosomes.

As used herein, the term "locus" (loci plural) can mean any site at which an edit to the native genomic sequence is desired. In one embodiment, said term can mean a specific place or places or a site on a chromosome where for example a gene or genetic marker is found.

As used herein, the term "genetically linked" can refer to two or more traits that are co-inherited at a high rate during breeding such that they are difficult to separate through crossing.

A "recombination" or "recombination event" as used herein can refer to a chromosomal crossing over or independent assortment.

As used herein, the term "phenotype" can refer to the observable characteristics of an individual cell, cell culture, organism, or group of organisms, which results from the interaction between that individual's genetic makeup (i.e., genotype) and the environment.

As used herein, the term "chimeric" or "recombinant" when describing a nucleic acid sequence or a protein sequence can refer to a nucleic acid, or a protein sequence, that links at least two heterologous polynucleotides, or two heterologous polypeptides, into a single macromolecule, or that rearranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence can comprise at least one nucleotide difference when compared to any other naturally occurring nucleotide sequence.

As used herein, the term "nucleic acid" can refer to a polymeric form of nucleotides of any length, either ribonucleotides or deoxyribonucleotides, or analogs thereof. This term can refer to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" can refer to any segment of DNA associated with a biological function. Thus, genes can include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" or "orthologue" is known in the art and can refer to related sequences that share a common ancestor or family member and are determined based on the degree of sequence identity.

The terms "homology," "homologous," "substantially similar" and "corresponding substantially" can be used interchangeably herein. Said terms can refer to nucleic acid fragments wherein changes in one or more nucleotide bases do not affect the ability of the nucleic acid fragment to mediate gene expression or produce a certain phenotype. These terms can also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared.

"Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Sequence homology between amino acid or nucleic acid sequences can be defined in terms of shared ancestry. Two segments of nucleic acid can have shared ancestry because of either a speciation event (orthologs) or a duplication event (paralogs). Homology among amino acid or nucleic acid sequences can be inferred from their sequence similarity such that amino acid or nucleic acid sequences are said to be homologous if said amino acid or nucleic acid sequences share significant similarity. Significant similarity can be strong evidence that two sequences are related by divergent evolution from a common ancestor. Alignments of multiple sequences can be used to discover the homologous regions. Homology can be determined using software programs readily available in the art, such as those discussed in Current Protocols in Molecular Biology (F. M. Ausubel et al., eds., 1987) Supplement 30, section 7.718, Table 7.71. Some alignment programs are BLAST (NCBI), MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "endogenous" or "endogenous gene," can refer to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" can be used interchangeably with the term "heterologous," and refers to a substance coming from some source other than its native source. For example, the terms "exogenous protein," or "exogenous gene" refer to a protein or gene from a non-native source or location, and that have been artificially supplied to a biological system.

As used herein, the term "nucleotide change" refers to, e.g., nucleotide substitution, deletion, and/or insertion, as is well understood in the art. For example, mutations can contain alterations that produce silent substitutions, additions, or deletions, but do not alter the properties or activities of the encoded protein or how the proteins are made. Alternatively, mutations can be nonsynonymous substitutions or changes that can alter the amino acid sequence of the encoded protein and can result in an alteration in properties or activities of the protein.

As used herein, the term "protein modification" can refer to, e.g., amino acid substitution, amino acid modification, deletion, and/or insertion, as is well understood in the art.

As used herein, the term "at least a portion" or "fragment" of a nucleic acid or polypeptide can mean a portion having the minimal size characteristics of such sequences, or any larger fragment of the full-length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 1 amino acid, 2 amino acids, 3 amino acids, 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides can also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual (3$^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, multiplex methods using multiple sets of paired primers to simultaneously amplify more than one DNA segment, and the like.

The term "primer" as used herein can refer to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer can be single stranded for maximum efficiency in amplification. The primer can be an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

As used herein, "promoter" can refer to a DNA sequence capable of controlling the expression of a coding sequence or functional RNA. In some embodiments, the promoter sequence consists of proximal and more distal upstream elements, the latter elements often referred to as enhancers. Accordingly, an "enhancer" can be a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. For example, promoters can be used to change the level of expression of a gene in a manner that is constitutive or that responds to an endogenous or exogenous stimulus. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" can be used interchangeably herein. A recombinant construct can comprise an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by direct sequencing, Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" or "functionally linked" can mean the sequential arrangement of any functional genetic element according to the disclosure (e.g., promoter, terminator, degron, solubility tag, etc.) with a further oligo- or polynucleotide. In some cases, the sequential arrangement can result in transcription of said further polynucleotide. In some cases, the sequential arrangement can result in translation of said further polynucleotide. The functional genetic elements can be present upstream or downstream of the further oligo or polynucleotide. In one example, "operably linked" or "functionally linked" can mean a promoter controls the transcription of the gene adjacent or downstream or 3' to said promoter. In another example, "operably linked" or "functionally linked" can mean a terminator controls termination of transcription of the gene adjacent or upstream or 5' to said terminator.

The term "product of interest" or "biomolecule" as used herein can refer to any product produced by microbes from feedstock. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a microbe, such as: a microbial enzyme, including: catalase, amylase, protease, pectinase, glucose isomerase, cellulase, hemicellulase, lipase, lactase, streptokinase, and many others. The intracellular component may also include recombinant proteins, such as insulin, hepatitis B vaccine, interferon, granulocyte colony-stimulating factor, streptokinase and others.

As used herein, the term "HTP genetic design library" or "library" refers to collections of genetic perturbations according to the present disclosure. In some embodiments, the libraries of the present invention may manifest as i) a collection of sequence information in a database or other computer file, ii) a collection of genetic constructs comprising the aforementioned series of genetic elements, or iii) host cell strains comprising said genetic elements. In some embodiments, the libraries of the present disclosure may refer to collections of individual elements (e.g., collections of promoters for PRO swap libraries, collections of terminators for STOP swap libraries, collections of protein solubility tags for SOLUBILITY TAG swap libraries, or collections of protein degradation tags for DEGRADATION TAG swap libraries). In other embodiments, the libraries of the present disclosure may also refer to combinations of genetic elements, such as combinations of promoter:genes, gene:terminator, or even promoter:gene:terminators. In some embodiments, the libraries of the present disclosure may also refer to combinations of promoters, terminators, protein solubility tags and/or protein degradation tags. In some embodiments, the libraries of the present disclosure further comprise metadata associated with the effects of applying each member of the library in host organisms. For example, a library as used herein can include a collection of promoter::gene sequence combinations, together with the resulting effect of those combinations on one or more phenotypes in a particular species, thus improving the future predictive value of using said combination in future promoter swaps.

As used herein, the term "SNP" can refer to Small Nuclear Polymorphism(s). In some embodiments, SNPs of the present disclosure should be construed broadly, and include single nucleotide polymorphisms, sequence insertions, deletions, inversions, and other sequence replacements. As used herein, the term "non-synonymous" or "non-synonymous SNPs" can refer to mutations that lead to coding changes in host cell proteins.

A "high-throughput (HTP)" method of genomic engineering may involve the utilization of at least one piece of equipment that enables one to evaluate a large number of experiments or conditions, for example, automated equipment (e.g. a liquid handler or plate handler machine) to carry out at least one-step of said method.

The term "polynucleotide" as used herein can encompass oligonucleotides and refers to a nucleic acid of any length. Polynucleotides may be DNA or RNA. Polynucleotides may be single-stranded (ss) or double-stranded (ds) unless otherwise specified. Polynucleotides may be synthetic, for example, synthesized in a DNA synthesizer, or naturally occurring, for example, extracted from a natural source, or derived from cloned or amplified material. Polynucleotides referred to herein can contain modified bases or nucleotides.

The term "pool", as used herein, can refer to a collection of at least 2 polynucleotides. A pool of polynucleotides may comprise a plurality of different polynucleotides. In some embodiments, a set of polynucleotides in a pool may comprise at least 5, at least 10, at least 12 or at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, at least 500, at least 600, at least 700, at least 800, at least 900, or at least 1000 or more polynucleotides.

As used herein, the term "assembling", can refer to a reaction in which two or more, four or more, six or more, eight or more, ten or more, 12 or more 15 or more polynucleotides, e.g., four or more polynucleotides are joined to another to make a longer polynucleotide.

As used herein, the term "incubating under suitable reaction conditions", can refer to maintaining a reaction a suitable temperature and time to achieve the desired results, i.e., polynucleotide assembly. Reaction conditions suitable for the enzymes and reagents used in the present method are known (e.g. as described in the Examples herein) and, as such, suitable reaction conditions for the present method can be readily determined. These reactions conditions may change depending on the enzymes used (e.g., depending on their optimum temperatures, etc.).

As used herein, the term "joining", can refer to the production of covalent linkage between two sequences.

As used herein, the term "composition" can refer to a combination of reagents that may contain other reagents, e.g., glycerol, salt, dNTPs, etc., in addition to those listed. A composition may be in any form, e.g., aqueous or lyophilized, and may be at any state (e.g., frozen or in liquid form).

As used herein a "vector" is a suitable DNA into which a fragment or DNA assembly may be integrated such that the engineered vector can be replicated in a host cell. A linearized vector may be created restriction endonuclease digestion of a circular vector or by PCR. The concentration of fragments and/or linearized vectors can be determined by gel electrophoresis or other means.

As used herein, the term "integron" can refer to a mobile genetic element or a genetic element integrated into a nucleic acid (e.g., a genome, plasmid, etc.) that comprises or contains a gene cassette comprising an exogenous gene, a gene encoding an integron integrase (IntI), an integron-associated recombination site (attI) and an integron-associated promoter (Pc) as described in Gillings, Michael R, "Integrons: Past, Present, and Future" Microbiology and Molecular Biology Review, June 2014 Vol. 78:2, pp. 257-277, the contents of which are herein incorporated by reference.

Overview

Provided herein are compositions and kits for use in generating one or more genetically modified microbial strains. Also provided herein are methods for iteratively editing the genome of a microbial host cell that can be used to generate one or more genetically modified microbial strains. That is, the methods can be useful for introducing and/or stacking a plurality of genetic edits in the genome of a microbial host cell. In order to facilitate the stacking of the plurality of genetic edits within its genome, the microbial host cell can comprise a site-specific restriction enzyme and/or one or more recombination systems and/or each genetic edit from the plurality of genetic edits can comprise sequence on both it's 5' and 3' ends (e.g., homology arms) that is complementary or homologous to sequence at a locus or sequence adjacent to or flanking a locus present within a nucleic acid (e.g., genome, plasmid, etc.) in the microbial host cell. The methods provided herein can entail introducing the genetic edits on repair or donor nucleic acids into the microbial host cell in successive rounds of transformation and selection such that at least one of the rounds does not entail the use of functional counterselection (e.g., antibiotic, chemical, temperature, etc.). In one embodiment, the repair or donor nucleic acids are present on plasmids, which are introduced in each round and comprise a selectable marker gene that is different from a selectable marker gene present on a plasmid introduced in the preceding and the succeeding round of transformation and selection. Further, the plasmids introduced in each round of transformation and selection can comprise an origin of replication that is identical to each other plasmid introduced throughout the method. Curing or removal of plasmids from the microbial host cell that were introduced in a preceding round of transformation can be facilitated via growth on media comprising reagents that exert selective pressure for microbial host cells expressing the selectable marker gene of the current round. Also provided herein are compositions and kits for use in the methods provided herein for iteratively editing the genome of a microbial host cell. The genetic edits can be selected from the group consisting of an insertion (e.g., ranging from a small insertion of one or a few nucleotides to pathway insertions of multiple genes), a deletion (e.g., ranging from a small deletion of one or a few nucleotides to pathway deletions of multiple genes), a single nucleotide polymorphism, a genome shuffling, a large scale deletion, a genomic edit, a plasmid edit, and multiple edits, or any combination thereof. Each round of transformation in the methods provided herein can introduce a single genetic edit into a single locus within a nucleic acid (e.g., genome, plasmid, etc.) in a microbial host cell or a plurality of genetic edits into a plurality of loci with a nucleic acid (e.g., genome, plasmid, etc.) in a microbial host cell. The microbial host cells for use in the methods, compositions and kits provided herein can be a prokaryotic or eukaryotic cell.

Figure 10A:
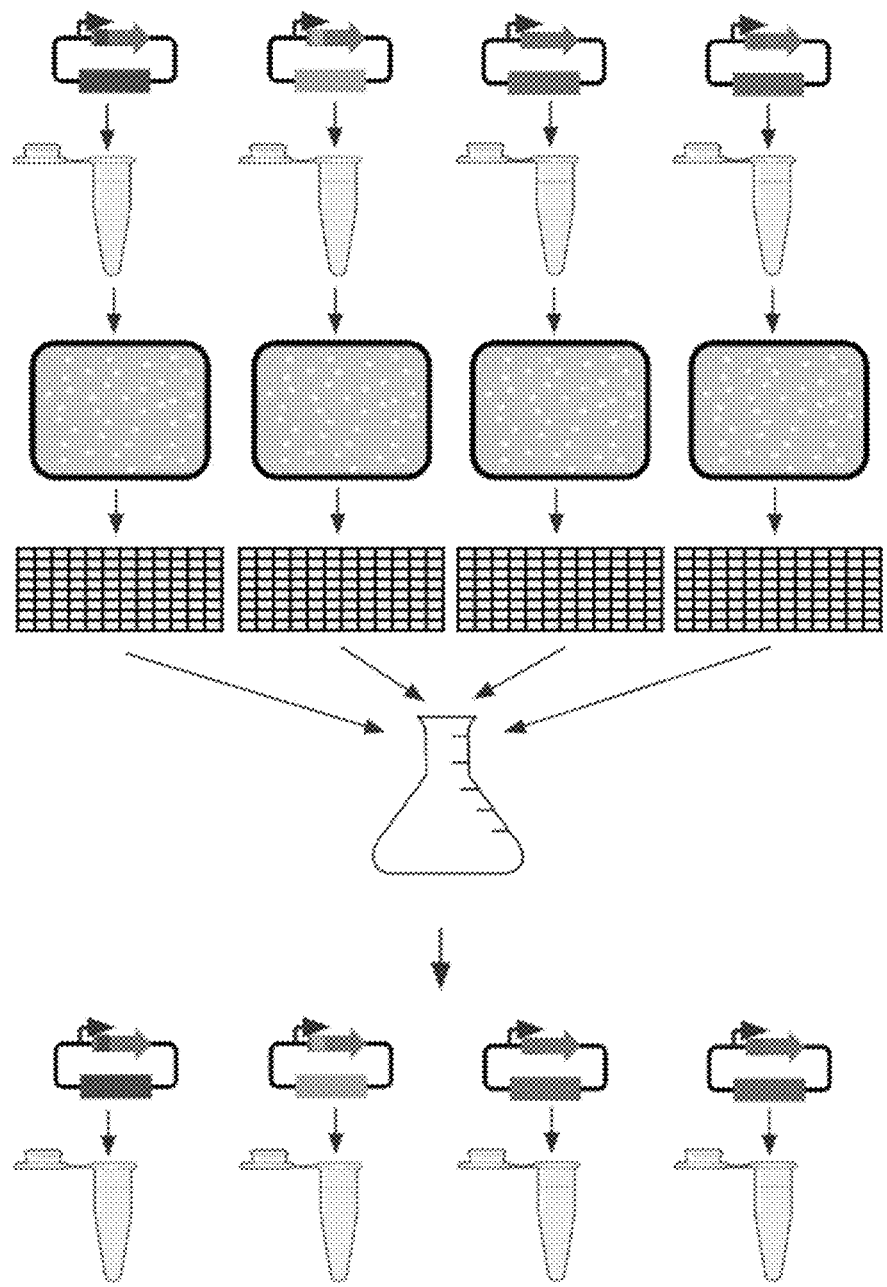

In one embodiment provided herein is a method for editing a microbial host cell genome, the method comprising: (a) introducing into the microbial host cell a first plasmid comprising a first repair fragment and a selection marker gene, wherein the first repair fragment comprises homology arms separated by a sequence for a genetic edit in or adjacent to a first locus in the genome of the microbial host cell, wherein the homology arms comprise sequence complementary or homologous to sequence that flanks the first locus in the genome of the microbial host cell; (b) growing the microbial host cells from step (a) in a media selective for microbial host cells expressing the selection marker gene and isolating microbial host cells from cultures derived therefrom; and (c) growing the microbial host cells isolated in step (b) in media not selective for the selection marker gene and isolating microbial host cells from cultures derived therefrom. In one embodiment, the editing method comprises a single round of introducing a genetic edit to the microbial host cell. In one embodiment, the editing method comprises performing a single round of introducing a genetic edit to the microbial host cell of several individual microbial host cells and then pooling each of the several or subsets of the several individual microbial host cells to form a main culture. In one embodiment, the method is iterative and further comprises step (d) that comprises repeating steps (a)-(c) in one or more additional rounds in the microbial host cells isolated in step (c), wherein each of the one or more additional rounds comprises introducing an additional plasmid comprising an additional repair fragment, wherein the additional repair fragment comprises homology arms separated by sequence for a genetic edit in or adjacent to a locus in the genome of the microbial host cell, wherein the homology arms comprise sequence complementary or homologous to sequence that flanks the locus in the genome of the microbial host cell, and wherein the additional plasmid comprises a different selection marker gene than the selection marker gene introduced in a previous round of selection, thereby iteratively editing the microbial host cell genome. The one or more additional rounds can be at least, at most or exactly 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1000 rounds of introducing a genetic edit to the microbial host cell. In one embodiment, counterselection is not performed after at least one round of editing. In another embodiment, counterselection is not performed after every round of editing. In another embodiment, counterselection is not performed after any round of editing. In yet another embodiment, counterselection is performed only after alternating rounds of editing. In still another embodiment, counterselection is performed only after a final round of editing. The counterselection can be antibiotic, chemical or temperature-based. The counterselection can be via expression of a counter-selectable marker gene by the microbial host cell. The selection marker gene can be an antibiotic or auxotrophic selection marker gene such as, for example, an antibiotic or auxotrophic selection marker gene provided herein. The locus targeted in each of the one or more additional rounds can be the first locus or another or different locus from the first locus. The locus targeted in each of the one or more additional rounds can be the same locus as the locus from another round of the iterative method. The locus targeted in each of the one or more additional rounds can be another or a different locus as the locus from another round of the iterative method. In one embodiment, the editing method comprises performing a single round of introducing a genetic edit to the microbial host cell of several individual microbial host cells and then pooling each of the several or subsets of the several individual microbial host cells to form a main culture and then iteratively editing individual microbial host cells separated out from the main culture. Further to this embodiment, individual microbial host cells can be pooled after each round of editing to form a main culture after each round and then separate microbial host cell cultures can be divided from the main culture after each round of editing and subjected to further rounds of editing. This can be referred to as pooled parent iterative editing and can follow the general process outlined in FIG. 10A. It should be noted that pooled parent iterative editing can be multiplexed in nature such that each repair fragment introduced to an individual host cell culture can comprise multiple genetics edits.

In one embodiment, each repair fragment (i.e., first and/or additional repair fragment(s)) can comprise sequence for the same genetic edit as one or more of the genetic edits from a previous repair fragment. Thus, sequence for the same genetic edit can be introduced at each locus in each round (first and/or additional rounds) of the method. In one embodiment, each repair fragment (i.e., first and/or additional repair fragment(s)) can comprise sequence for a different genetic edit as one or more of the genetic edits from a previous repair fragment. Thus, sequence for a different genetic edit can be introduced at each locus in each round (first and/or additional rounds) of the method. In one embodiment, a plurality of different first repair fragments are introduced. The plurality of different first repair fragments can comprise a sequence for a genetic edit in or adjacent to different loci. In one embodiment, a plurality of different additional repair fragments are introduced. The plurality of additional repair fragments can comprise a sequence for a genetic edit in or adjacent to different loci. In one embodiment, the genetic edit introduced at each different locus in each round of the method is the same genetic edit. In one embodiment, the genetic edit introduced at each different locus in each round of the method is a different genetic edit. The genetic edit can be selected from the group consisting of an insertion, a deletion, a single nucleotide polymorphism, a genome shuffling, a large scale deletion, a genomic edit, a plasmid edit, and multiple edits, or any combination thereof.

In one embodiment, the method further comprises a step (e) that comprises introducing a final plasmid comprising a final repair fragment in a terminal round of repeating steps (a)-(c). The final repair fragment can comprise homology arms separated by sequence for a genetic edit in or adjacent to a final locus in the genome of the microbial host cell such that the homology arms comprise sequence complementary or homologous to sequence that flanks the final locus in the genome of the microbial host cell. The final locus can be a different locus from any locus edited previously. The final plasmid can comprise sequence for a different selection marker gene than the selection marker gene introduced in a previous round of selection. In one embodiment, counterselection is performed following the terminal round. In one embodiment, the method further comprises introducing a guide RNA (gRNA) comprising a guide sequence complementary or homologous to a sequence present on or associated with the final repair fragment to facilitate removal of the final repair fragment following the terminal round via an RNA-guided DNA endonuclease. The RNA-guided DNA endonuclease can be any such endonuclease known in the art and/or provided herein. The gRNA can comprise a CRISPR RNA (crRNA) and a trans-activating crRNA (tracrRNA). In one embodiment, the gRNAs comprises a single gRNA (sgRNA).

In one embodiment provided herein is a method for editing a microbial host cell genome that comprises or entails: (a) introducing into the microbial host cell a first plasmid comprising a first repair fragment and a selection marker gene, wherein the microbial host cell comprises a site-specific restriction enzyme or a sequence encoding a site-specific restriction enzyme is introduced into the microbial host cell along with the first plasmid, wherein the site-specific restriction enzyme targets (e.g., binds to) a first locus in the genome of the microbial host cell, and wherein the first repair fragment comprises homology arms separated by a sequence for a genetic edit in or adjacent to the first locus, wherein the homology arms comprise sequence complementary or homologous to sequence that flanks the first locus in the genome of the microbial host cell; (b) growing the microbial host cells from step (a) in a media selective for microbial host cells expressing the selection marker gene and isolating microbial host cells from cultures derived therefrom; and (c) growing the microbial host cells isolated in step (b) in media not selective for the selection marker gene and isolating microbial host cells from cultures derived therefrom. In one embodiment, the editing method comprises a single round of introducing sequence for a genetic edit to the microbial host cell. In one embodiment, the editing method comprises performing a single round of introducing a genetic edit to the microbial host cell of several individual microbial host cells and then pooling each of the several or subsets of the several individual microbial host cells to form a main culture. In one embodiment, the method is iterative and further comprises step (d) which comprises or entails repeating steps (a)-(c) in one or more additional rounds in the microbial host cells isolated in step (c), wherein each of the one or more additional rounds comprises introducing an additional plasmid comprising an additional repair fragment, wherein the additional repair fragment comprises homology arms separated sequence for a genetic edit in or adjacent to a locus in the genome of the microbial host cell, wherein the homology arms comprise sequence complementary or homologous to sequence that flanks the locus in the genome of the microbial host cell and wherein the additional plasmid comprises a different selection marker gene than the selection marker gene introduced in a previous round of selection, and wherein the microbial host cell comprises a site-specific restriction enzyme or a sequence encoding a site-specific restriction enzyme is introduced into the microbial host cell along with the additional plasmid that targets the first locus or another locus in the genome of the microbial host cell, thereby iteratively editing the microbial host cell genome. The one or more additional rounds can be at least, at most or exactly 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1000 rounds of introducing sequence for a genetic edit to the microbial host cell. In one embodiment, counterselection is not performed after at least one round of editing. In another embodiment, counterselection is not performed after every round of editing. In another embodiment, counterselection is not performed after any round of editing. In yet another embodiment, counterselection is performed only after alternating rounds of editing. In still another embodiment, counterselection is performed only after a final round of editing. The counterselection can be antibiotic, chemical or temperature-based. The counterselection can be via expression of a counter-selectable marker gene by the microbial host cell.

The selection marker gene can be an antibiotic or auxotrophic selection marker gene, such as, for example, any antibiotic or auxotrophic selection marker gene provided herein. In one embodiment, the site-specific enzyme of step (a) cleaves a sequence at the first locus in the genome of the microbial host cell. In one embodiment, the site-specific restriction enzyme of step (d) cleaves a sequence at the locus targeted in each of the one or more additional rounds in the genome of the microbial host cell. The locus targeted in each of the one or more additional rounds can be the first locus or another or different locus from the first locus. The locus targeted in each of the one or more additional rounds can be the same locus as the locus from another round of the iterative method. The locus targeted in each of the one or more additional rounds can be another or a different locus as the locus from another round of the iterative method. In one embodiment, the editing method comprises performing a single round of introducing a genetic edit to the microbial host cell of several individual microbial host cells and then pooling each of the several or subsets of the several individual microbial host cells to form a main culture and then iteratively editing individual microbial host cells divided from the main culture. Further to this embodiment, individual microbial host cells can be pooled after each round of editing to form a main culture after each round and then separate microbial host cell cultures can be divided from the main culture after each round of editing and subjected to further rounds of editing. This can be referred to as pooled parent iterative editing and can follow the general process outlined in FIG. 10A. It should be noted that pooled parent iterative editing can be multiplexed in nature such that each repair fragment introduced to an individual host cell culture can comprise multiple genetics edits.

Each of the repair fragments comprising sequence for a genetic edit introduced in each round (e.g., first and/or additional round) of the editing method can comprise sequence complementary or homologous to a locus targeted by a site-specific restriction enzyme in the microbial host cell. Each of the genetic edits present on a repair fragment introduced in each round (e.g., first and/or additional rounds) of the editing method can be flanked by sequence complementary or homologous to a locus targeted by a site-specific restriction enzyme in the microbial host cell. The sequence complementary or homologous to a locus targeted by a site-specific restriction enzyme in the microbial host cell can be present on both a 5' and 3' end of each of the repair fragments or genetic edits and can be referred to as homology arms. In one embodiment, each repair fragment (i.e., first and/or additional repair fragment(s)) can comprise sequence for the same genetic edit as one or more of the genetic edits present on a previous repair fragment. Thus, sequence for the same genetic edit can be introduced at each locus in each round (first and/or additional rounds) of the method. In one embodiment, each repair fragment (i.e., first and/or additional repair fragment(s)) can comprise sequence for a different genetic edit as one or more of the genetic edits present on a previous repair fragment. Thus, sequence for a different genetic edit can be introduced at each locus in each round (first and/or additional rounds) of the method. In one embodiment, a plurality of different first repair fragments are introduced. The plurality of different first repair fragments can comprise a sequence for a genetic edit in or adjacent to different loci. In one embodiment, a plurality of different additional repair fragments are introduced. Each repair fragment in the plurality of additional repair fragments can comprise a sequence for a genetic edit in or adjacent to different loci. In one embodiment, the genetic edit introduced at each different locus in each round of the method is the same genetic edit. In one embodiment, the genetic edit introduced at each different locus in each round of the method is a different genetic edit. Further to this embodiment, a site-specific restriction enzyme in the microbial host cell can cleave a sequence at each different locus in the one or more repeated rounds. The genetic edit can be selected from the group consisting of an insertion, a deletion, a single nucleotide polymorphism, a genome shuffling, a large scale deletion, a genomic edit, a plasmid edit, and multiple edits, or any combination thereof.

In one embodiment, the method further comprises a step (e) that comprises introducing a final plasmid comprising a final repair fragment in a terminal round of repeating steps (a)-(c). The final repair fragment can comprise a sequence for a genetic edit in or adjacent to a final locus in the genome of the microbial host cell. The final locus can be a different locus from any locus edited previously. The final plasmid can comprise sequence for a different selection marker gene than the selection marker gene introduced in a previous round of selection. The microbial host cell can comprise a site-specific restriction enzyme or a sequence encoding a site-specific restriction enzyme can be introduced into the microbial host cell along with the final plasmid that targets the final locus in the genome of the microbial host cell. The final repair fragment can comprise homology arms that comprise sequence complementary or homologous to the final locus or loci cleaved by the site-specific restriction enzyme. In one embodiment, the method further comprises introducing a guide RNA (gRNA) comprising a guide sequence complementary or homologous to a sequence present on or associated with the final repair fragment to facilitate removal of the final repair fragment following the terminal round via an RNA-guided DNA endonuclease. The RNA-guided DNA endonuclease can be any such endonuclease known in the art and/or provided herein. The gRNA can comprise a CRISPR RNA (crRNA) and a trans-activating crRNA (tracrRNA). In one embodiment, the gRNAs comprises a single gRNA (sgRNA).

The site-specific restriction enzyme for use in any step of any of the methods provided herein can be any site-specific restriction enzyme known in the art. The site-specific restriction enzyme can be selected from the group consisting of an RNA-guided DNA endonuclease, a meganuclease, a transcription activator-like effector nucleases (TALEN), and a zinc-finger nuclease (ZFN). In one embodiment, the site-specific restriction enzyme is encoded on a plasmid.

In one embodiment, the site-specific restriction enzyme is encoded on an integron. In one embodiment, the site-specific restriction enzyme is encoded in the genome. In one embodiment, the site-specific restriction enzyme is translated from RNA. In one embodiment, the site-specific restriction enzyme is introduced into the cell as protein. In one embodiment, the site-specific restriction enzyme is an RNA-guided DNA endonuclease. The RNA guided DNA endonuclease can be a Class 2 CRISPR-Cas System RNA guided endonuclease. The Class 2 CRISPR-Cas system RNA guided DNA endonuclease is a Type II, Type V or Type VI RNA guided endonuclease. In one embodiment, the CRISPR-Cas system RNA guided DNA endonuclease is selected from Cas9, Cas12a, Cas12b, Cas12c, Cas12d, Cas12e, Cas13a, Cas13b, Cas13c, Cpf1, and MAD7, or homologs, orthologs, mutants, variants or modified versions thereof.

In one embodiment, the aforementioned editing methods can be multiplex in nature, meaning that multiple genetic edits can be introduced into a nucleic acid (e.g., genome, plasmid, etc.) of a single microbe per editing round. Further to this embodiment, the repair fragment introduced in each round or transformation of the aforementioned iterative editing method comprises sequence for 2 or more genetic edits. As provided herein, each of the repair fragments can be present on a plasmid. The repair fragment introduced in each round or transformation of the aforementioned iterative editing method can comprise sequence for at least, at most or exactly 2, 3, 4, 5, 6, 7, 8, 9, 10, 15, 20, 25, 30, 35, 40, 45, 50, 55, 60, 65, 70, 75, 80, 85, 90, 95, or 100 genetic edits. Sequence for each of the genetic edits on a repair fragment can be selected from the group consisting of an insertion, a deletion, a single nucleotide polymorphism, a genome shuffling, a large scale deletion, a genomic edit, a plasmid edit, or multiple edits as provided herein.

In one embodiment, the aforementioned editing methods are pooled in nature, meaning that components for generating multiple edits in a population of microbes are mixed or pooled per a round of editing. Further to this embodiment, each round or transformation of the aforementioned iterative editing method can comprise adding 2 or more repair fragments. Each repair fragment can target a different locus than each other repair fragment of the 2 or more repair fragments. Each repair fragment can comprise sequence for a different genetic edit than each other repair fragment of the 2 or more repair fragments. Each round or transformation of the aforementioned iterative editing method can add at least, at most or exactly 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1000 repair fragments per round or transformation. As provided herein, each of the 2 or more repair fragments can be present on a plasmid, which can be referred to as an editing plasmid. Each of the 2 or more repair fragments can be present on the same plasmid. Each of the 2 or more repair fragments can be present on different plasmids. In one embodiment, each of the 2 or more repair fragments added in each round or transformation can comprise sequence for 2 or more genetic edits as provided herein. Different gRNA/repair fragment pairs can comprise at least, at most or exactly 2, 3, 4, 5, 6, 7, 8, 9, 10, 12, 14, 16, 18, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 different gRNAs and/or repair fragments, and can thereby generate at least, at most or exactly 2, 3, 4, 5, 6, 7, 8, 9, 10, 12, 14, 16, 18, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 different genetically modified microbial strains in an edited population of the microbial host cells. The sequence for each of the genetic edits on a repair fragment can be selected from the group consisting of an insertion, a deletion, a single nucleotide polymorphism, a genome shuffling, a large scale deletion, a genomic edit, a plasmid edit, or multiple edits as provided herein.

In another embodiment, provided herein is a method for editing a microbial host cell genome comprising: (a) introducing into the microbial host cell a first plasmid, a first guide RNA (gRNA) and a first repair fragment, wherein the gRNA comprises a sequence complementary or homologous to a first locus in the genome of the microbial host cell, wherein the first repair fragment comprises homology arms separated by a sequence for a genetic edit in or adjacent to the first locus, wherein the homology arms comprise sequence complementary or homologous to sequence that flanks the first locus in the genome of the microbial host cell, and wherein the first plasmid comprises a selection marker gene and at least one or both of the gRNA and the repair fragment, and wherein the microbial host cell comprises an RNA-guided DNA endonuclease or an RNA-guided DNA endonuclease is introduced into the host cell along with the first plasmid; (b) growing the microbial host cells from step (a) in a media selective for the microbial host cells expressing the selection marker gene and isolating microbial host cells from cultures derived therefrom; (c) growing the microbial host cells isolated in step (b) in media not selective for the selection marker gene and isolating microbial host cells from cultures derived therefrom. In one embodiment, the editing method comprises a single round of introducing a genetic edit to the microbial host cell. In one embodiment, the editing method comprises performing a single round of introducing a genetic edit to the microbial host cell of several individual microbial host cells and then pooling each of the several or subsets of the several individual microbial host cells to form a main culture. In one embodiment, the method is iterative and further comprises step (d) which comprises or entails repeating steps (a)-(c) in one or more additional rounds in the microbial host cells isolated in step (c), wherein each of the one or more additional rounds comprises introducing an additional plasmid, an additional gRNA and an additional repair fragment, wherein the additional gRNA comprises sequence complementary or homologous to a locus in the genome of the microbial host cell, wherein the additional repair fragment comprise homology arms separated by a sequence for a genetic edit in or adjacent to the locus in the genome of the microbial host cell, wherein the homology arms comprise sequence complementary or homologous to sequence that flanks the locus in the genome of the microbial host cell, and wherein the additional plasmid comprises a different selection marker gene than the selection marker gene introduced in a previous round of selection, and wherein the additional plasmid comprises at least one or both of the additional gRNA and the additional repair fragment, thereby iteratively editing the microbial host cell genome. The one or more additional rounds can be at least, at most or exactly 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1000 rounds of introducing a genetic edit to the microbial host cell. In one embodiment, counterselection is not performed after at least one round of editing. In another embodiment, counterselection is not performed after every round of editing. In another embodiment, counterselection is not performed after any round of editing. In yet another embodiment, counterselection is performed only after alternating rounds of editing. In still another embodiment, counterselection is performed only after a final round of editing. The counterselection can be antibiotic, chemical or temperature-based. The counterselection can be via expression of an antibiotic, chemical or temperature-sensitive counter-selectable marker gene by the microbial host cell. The selection marker gene can be an antibiotic or auxotrophic selection marker gene. In one embodiment, the RNA-guided DNA endonuclease of step (a) cleaves a sequence at the first locus in the genome of the microbial host cell. The RNA-guided DNA endonuclease of step (d) cleaves a sequence at the locus targeted in each of the one or more additional rounds in the genome of the microbial host cell. The locus targeted in each of the one or more additional rounds can be the first locus or another or different locus from the first locus. The locus targeted in each of the one or more additional rounds can be the same locus as the locus from another round of the iterative method. The locus targeted in each of the one or more additional rounds can be another or a different locus as the locus from another round of the iterative method. In one embodiment, the editing method comprises performing a single round of introducing a genetic edit to the microbial host cell of several individual microbial host cells and then pooling each of the several or subsets of the several individual microbial host cells to form a main culture and then iteratively editing individual microbial host cells separated out from the main culture. Further to this embodiment, individual microbial host cells can be pooled after each round of editing to form a main culture after each round and then separate microbial host cell cultures can be divided from the main culture after each round of editing and subjected to further rounds of editing. This can be referred to as pooled parent iterative editing and can follow the general process outlined in FIG. 10A. It should be noted that pooled parent iterative editing can be multiplexed in nature such that each repair fragment introduced to an individual host cell culture can comprise multiple genetics edits.

In one embodiment, the first plasmid comprises the first gRNA and the first repair fragment and each of the additional plasmids comprises an additional gRNA and an additional repair fragment. In one embodiment, the first gRNA is provided as a linear fragment. In one embodiment, each additional gRNA is provided as a linear fragment. In one embodiment, the first gRNA and each additional gRNA is provided as a linear fragment. In one embodiment, the first gRNA comprises a CRISPR RNA (crRNA) and a trans-activating crRNA (tracrRNA). In one embodiment, each additional gRNA comprises a CRISPR RNA (crRNA) and a trans-activating crRNA (tracrRNA). In one embodiment, both the first gRNA and each additional gRNA comprises a CRISPR RNA (crRNA) and a trans-activating crRNA (tracrRNA). In one embodiment, the first gRNA is a single gRNA (sgRNA). In one embodiment, each additional gRNA is a single gRNA (sgRNA). In one embodiment, both the first gRNA and each additional gRNA is a single gRNA (sgRNA). The gRNAs introduced in the additional round(s) of editing can target a different locus or loci from a previous round of editing. The RNA-guided DNA endonuclease can cleave a sequence in the genome of the microbial host cell at each locus targeted by a gRNA in each round of the aforementioned editing method.

Each of the repair fragments or genetic edits present therein introduced in successive rounds of the editing method can comprise sequence complementary or homologous to sequence in, at or adjacent to a targeted locus cleaved by the RNA-guided DNA endonuclease. The sequence complementary or homologous to a targeted locus can be present on both a 5' and 3' end of each of the repair fragments or sequence for genetic edit(s) present therein and can be referred to as homology arms. In one embodiment, the first repair fragment is provided as a linear fragment. In one embodiment, each additional repair fragment is provided as a linear fragment. In one embodiment, both the first repair fragment and each additional repair fragment are provided as a linear fragment. In one embodiment, the first repair fragment is provided as ssDNA or dsDNA. In one embodiment, each additional repair fragment is provided as ssDNA or dsDNA. In one embodiment, both the first repair fragment and each additional repair fragment is provided as ssDNA or dsDNA. The linear fragment can contain one or more end modifications. The end modifications can be applied to the 5' and/or 3' ends of the linear fragment. The end modifications can be selected from a group consisting of, but not limited to: phosphorylated ends, phosphothiorate linked bases, hairpins, inverted bases, base modifications, 2' O-methyl bases, locked nucleic bases, phosphorothioated 2' O-methyl bases, and phosphorothioated locked nucleic bases. Each repair fragment (i.e., first and/or additional repair fragment(s)) can comprise sequence for the same genetic edit as one or more of the genetic edits present on a previous repair fragment. Each repair fragment (i.e., first and/or additional repair fragment(s)) can comprise sequence for a different genetic edit as one or more of the genetic edits present on a previous repair fragment. In one embodiment, a plurality of different first repair fragments are introduced. Each repair fragment in the plurality of different first repair fragments can comprise a sequence for a genetic edit in or adjacent to different loci. In one embodiment, a plurality of different additional repair fragments are introduced. The plurality of additional repair fragments can comprise a sequence for a genetic edit in or adjacent to different loci. In one embodiment, the genetic edit introduced at each different locus in each round of the method is the same genetic edit. In one embodiment, the genetic edit introduced at each different locus in each round of the method is a different genetic edit. The genetic edit can be selected from the group consisting of an insertion, a deletion, a single nucleotide polymorphism, a genome shuffling, a large scale deletion, a genomic edit, a plasmid edit, and multiple edits, or any combination thereof.

In one embodiment, the method further comprises a step (e) that comprises introducing a final plasmid, a final gRNA and a final repair fragment in a terminal round of repeating steps (a)-(c). The final gRNA can comprise a sequence complementary or homologous to a final locus in the genome of the microbial host cell. The final locus can be a different locus from any locus targeted by a gRNA previously introduced into the microbial host cell. The final repair fragment can comprise homology arms separated by a sequence for a genetic edit in the final locus. The homology arms can comprise sequence that is complementary or homologous to sequence that flanks the final locus. The final gRNA and/or the final repair fragment can be associated with a sequence for a different selection marker gene than the selection marker gene introduced in a previous round of selection. The final plasmid can comprise at least one or both of the final gRNA and the final repair fragment. In one embodiment, the final gRNA is provided as a linear fragment. In one embodiment, the final gRNA comprises a CRISPR RNA (crRNA) and a trans-activating crRNA (tracrRNA). In one embodiment, the final gRNA is a single gRNA (sgRNA).

In one embodiment, the method further comprises a step (f) that comprises introducing a gRNA comprising a guide sequence complementary or homologous to a sequence present on or associated with the final repair fragment to facilitate removal of the final repair fragment following the terminal round via CRISPR. In one embodiment, the gRNA comprising a guide sequence complementary or homologous to a sequence present on or associated with the final repair fragment is provided as a linear fragment. In one embodiment, the gRNA comprising a guide sequence complementary or homologous to a sequence present on or associated with the final repair fragment comprises a CRISPR RNA (crRNA) and a trans-activating crRNA (tracrRNA). In one embodiment, the gRNA comprising a guide sequence complementary or homologous to a sequence present on or associated with the final repair fragment is a single gRNA (sgRNA).

In one embodiment, the aforementioned editing method is multiplex in nature, meaning that multiple genetic edits can be introduced into the genome of a single microbe per editing round. Further to this embodiment, the repair fragment introduced in each round or transformation of the aforementioned iterative editing method comprises sequence for 2 or more genetic edits and each of the 2 or more genetic edits is paired with a gRNA. In another embodiment, gRNAs are introduced that target at least 2 or more different loci, such that each gRNA is paired with either the same or a different repair fragment. In one embodiment, the repair fragments and/or paired gRNAs for multiplex editing is/are present as a linear fragment. The linear fragment can contain one or more end modifications. The end modifications can be applied to the 5' and/or 3' ends of the linear fragment. The end modifications can be selected from a group consisting of, but not limited to: phosphorylated ends, phosphothiorate linked bases, hairpins, inverted bases, base modifications, 2' O-methyl bases, locked nucleic bases, phosphorothioated 2' O-methyl bases, and phosphorothioated locked nucleic bases. In one embodiment, the repair fragments and/or paired gRNAs for multiplex editing is/are present on a plasmid. In one embodiment, the repair fragments and paired gRNAs for multiplex editing are each present on the same plasmid. In one embodiment, the repair fragments and paired gRNAs for multiplex editing are each present on a different plasmid such that each paired gRNA of the paired gRNAs is present on the same or different plasmid than each other paired gRNA of the paired gRNAs. The repair fragment introduced in each round or transformation of the aforementioned iterative editing method can comprise sequence for at least, at most or exactly 2, 3, 4, 5, 6, 7, 8, 9, 10, 15, 20, 25, 30, 35, 40, 45, 50, 55, 60, 65, 70, 75, 80, 85, 90, 95, or 100 genetic edits and each genetic edit can be paired with a gRNA. In one embodiment, the gRNAs introduced in the aforementioned editing method provided herein comprise a sequence complementary or homologous to a target locus or loci and each repair fragment comprises a sequence for at least, at most or exactly 2, 3, 4, 5, 6, 7, 8, 9, 10, 15, 20, 25, 30, 35, 40, 45, 50, 55, 60, 65, 70, 75, 80, 85, 90, 95, or 100 genetic edits in or adjacent to the target locus or loci. In one embodiment, the gRNAs introduced in the aforementioned editing method provided herein comprise a sequence complementary or homologous to a different locus or loci than any locus or loci targeted in a previous round of editing and each repair fragment comprises a sequence for at least, at most or exactly 2, 3, 4, 5, 6, 7, 8, 9, 10, 15, 20, 25, 30, 35, 40, 45, 50, 55, 60, 65, 70, 75, 80, 85, 90, 95, or 100 genetic edits in or adjacent to the different target locus or loci. The gRNAs introduced in each round or transformation of the aforementioned iterative editing method can target at least, at most or exactly 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1000 different loci and each gRNA can be paired with a repair fragment. In one embodiment, the gRNAs introduced in the aforementioned editing method provided herein comprise a sequence complementary or homologous to a same locus or loci than any locus or loci targeted in a previous round of editing and each repair fragment comprises a sequence for at least, at most or exactly 2, 3, 4, 5, 6, 7, 8, 9, 10, 15, 20, 25, 30, 35, 40, 45, 50, 55, 60, 65, 70, 75, 80, 85, 90, 95, or 100 different genetic edits in or adjacent to the target locus or loci than a genetic edit introduced in a previous round of editing. Each of the genetic edits present on a repair fragment can be selected from the group consisting of an insertion, a deletion, a single nucleotide polymorphism, a genome shuffling, a large scale deletion, a genomic edit, a plasmid edit, or multiple edits. Each of the gRNAs can comprise a CRISPR RNA (crRNA) and a trans-activating crRNA (tracrRNA). In one embodiment, each of the gRNAs are comprised of a single gRNA (sgRNA).

In one embodiment, the aforementioned iterative editing method is pooled in nature, meaning that components for generating multiple edits in a population of microbes are mixed or pooled per a round of editing. Further to this embodiment, each round or transformation of the aforementioned iterative editing method can comprise adding 2 or more gRNA/repair fragment pairs. In some cases, each gRNA/repair fragment pair can target a different locus than each other gRNA/repair fragment pair of the 2 or more gRNA/repair fragment pairs. In other cases, each gRNA/repair fragment pair can generate a different edit than each other gRNA/repair fragment pair of the 2 or more gRNA/repair fragment pairs. Each round or transformation of the aforementioned iterative editing method can add at least, at most or exactly 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1000 gRNA/repair fragment pairs per round or transformation. As provided herein, each of the 2 or more gRNA/repair fragment pairs can be present on a plasmid. In each gRNA/repair fragment pair, one or both of the gRNA or repair fragment can be a linear fragment. The linear fragment can contain one or more end modifications. The end modifications can be applied to the 5' and/or 3' ends of the linear fragment. The end modifications can be selected from a group consisting of, but not limited to: phosphorylated ends, phosphothiorate linked bases, hairpins, inverted bases, base modifications, 2' O-methyl bases, locked nucleic bases, phosphorothioated 2' O-methyl bases, and phosphorothioated locked nucleic bases. In each gRNA/repair fragment pair, one or both of the gRNA or repair fragment can be present on a plasmid. In one embodiment, each repair fragment in the 2 or more gRNA/repair fragment pairs added in each round or transformation can comprise sequence for 2 or more genetic edits such that each of the 2 or more genetic edits is paired with a gRNA as provided herein. Different gRNA/repair fragment pairs can comprise at least, at most or exactly 2, 3, 4, 5, 6, 7, 8, 9, 10, 12, 14, 16, 18, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 different gRNAs and/or repair fragments, and can thereby generate at least, at most or exactly 2, 3, 4, 5, 6, 7, 8, 9, 10, 12, 14, 16, 18, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000 different genetically modified microbial strains in an edited population of the microbial host cells. Sequence for each of the genetic edits on a repair fragment can be selected from the group consisting of an insertion, a deletion, a single nucleotide polymorphism, a genome shuffling, a large scale deletion, a genomic edit, a plasmid edit, or multiple edits. Each of the gRNAs can comprise a CRISPR RNA (crRNA) and a trans-activating crRNA (tracrRNA). In one embodiment, each of the gRNAs are comprised of a single gRNA (sgRNA).

In one embodiment, the RNA-guided DNA endonuclease utilized in any method provided herein is encoded on a plasmid. In one embodiment, the RNA-guided DNA endonuclease is encoded on an integron. In one embodiment, the RNA-guided DNA endonuclease is encoded in the genome. In one embodiment, the RNA-guided DNA endonuclease is translated from RNA, which can be introduced into the cell. In one embodiment, the RNA-guided DNA endonuclease is introduced into the cell as protein. The RNA guided DNA endonuclease can be a Class 2 CRISPR-Cas System RNA guided endonuclease. The Class 2 CRISPR-Cas system RNA guided DNA endonuclease is a Type II, Type V or Type VI RNA guided endonuclease. In one embodiment, the CRISPR-Cas system RNA guided DNA endonuclease is selected from Cas9, Cas12a, Cas12b, Cas12c, Cas12d, Cas12e, Cas13a, Cas13b, Cas13c, Cpf1, and MAD7, or homologs, orthologs, mutants, variants or modified versions thereof.

In one embodiment, the microbial host cell for use in any of the methods provided herein can further comprise a set of proteins from one or more recombination systems. The recombination system can be selected from a lambda red recombination system, a RecET recombination system, a Red/ET recombination system, any homologs, orthologs or paralogs of proteins from a lambda red recombination system or a RecET recombination system, or any combination thereof. In one embodiment, the set of proteins are from the lambda red recombination system and comprise a beta protein, a gam protein, and an exo protein. In one embodiment, the set of proteins from the recombination system is introduced into the microbial host cell as nucleic acids, for example via one or more plasmids or integrons, comprising genes encoding the set of proteins from the recombination system prior to step (a) in any of the iterative editing methods provided herein. In another embodiment, the set of proteins from the recombination system is stably expressed by the microbial host cell due to integration of genes encoding the set of proteins from the heterologous recombination system into the microbial host cell's genome. In another embodiment, the set of proteins from the recombination system is constitutively expressed by the microbial host cell due to integration of genes encoding the set of proteins from the heterologous recombination system into the microbial host cell's genome. In one embodiment, the set of proteins from the recombination system is present in an operon operably linked to an inducible promoter. The inducible promoter can be any promoter known in the art that is inducible by the addition or depletion of a reagent or metabolite or by a change in temperature. The reagent can be selected from the group consisting of arabinose, isopropyl beta-D-1-thiogalactopyranoside (IPTG), and tetracycline. Examples of inducible promoters for use in the methods and compositions provided herein can include the IPTG-inducible lac promoter and the arabinose-inducible pBAD promoter. In one embodiment, the set of proteins from the recombination system is present in an operon operably linked to a repressible promoter. The repressible promoter can be any promoter known in the art that is inducible by the removal of a reagent. Examples of repressible promoters for use in the methods and compositions provided herein can include the trp promoter and the reagent can be tryptophan. The one or more recombination systems can be heterologous to the microbial host cell.

In one embodiment, any of the methods provided herein further comprises genotyping the microbial host cells following growth of the microbial host cells in media selective for microbial host cells expressing a specific selection marker gene. The methods provided herein for editing a microbial host cell genome (e.g., in a singleplex, multiplex, or pooled fashion) can further comprise genotyping the microbial host cells between selection steps in method employing multiple selection steps. In one embodiment, any of the methods provided herein can further comprises genotyping the microbial host cells following growth of the microbial host cells in media not selective for a specific selection marker gene introduced into the microbial host cell. In one embodiment, the methods provided herein for iteratively editing a microbial host cell genome can further comprise genotyping the microbial host cells between select steps, e.g., select rounds of editing. In one embodiment, the methods provided herein for iteratively editing a microbial host cell genome can further comprise genotyping the microbial host cells between every round of editing. In one embodiment, the methods provided herein for iteratively editing a microbial host cell genome can further comprise genotyping the microbial host cells after a final step, e.g., the final step of editing. In one embodiment, the methods provided herein for iteratively editing a microbial host cell genome can further comprise genotyping the microbial host cells only after the final round of editing, following at least, at most or exactly 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1000 rounds of editing. The genotyping can be performed to confirm the presence of the desired modification. Genotyping can be performed by colony PCR, restriction digest, Sanger sequencing, next-generation sequencing (NGS), detection of the presence/absence of a reporter gene or antibiotic, or other standard methods in the field. Genetic edits can be also confirmed by sequencing such as with any next generation sequencing method known in the art.

In another embodiment, provided herein is a method for clearing a previously present plasmid from a microbial host cell, the method comprising: (a) introducing into the microbial host cell a first plasmid comprising a first selection marker gene; and (b) growing the microbial host cells from step (a) in a media selective for microbial host cells expressing the selection marker gene and isolating microbial host cells from cultures derived therefrom, wherein the previously present and the introduced first plasmids comprise an identical origin of replication, thereby clearing the previously present plasmid from a microbial host cell, wherein counterselection is not performed to facilitate clearance of a previously present plasmid. The counterselection can be via expression of an antibiotic, chemical or temperature-sensitive counter-selectable marker gene by the microbial host cell. In one embodiment, the method further comprises step (c), comprising growing the microbial host cells isolated in step (b) in media not selective for the selection marker gene and isolating microbial host cells from cultures derived therefrom. In a still further embodiment, the method further comprises repeating steps (a)-(c) in one or more rounds. Each of the one or more rounds can comprise introducing an additional plasmid comprising a different selection marker gene than the selection marker gene introduced in a previous round of selection, wherein the previously present and additionally introduced plasmids comprise an identical origin of replication. The previously present plasmid can be a native plasmid or a heterologous plasmid. In one embodiment, counterselection is not performed after at least one round of editing. In another embodiment, counterselection is not performed after every round of editing. In another embodiment, counterselection is not performed after any round of editing. In yet another embodiment, counterselection is performed only after alternating rounds of editing. In still another embodiment, counterselection is performed only after a final round of editing. The selection marker gene can be an antibiotic or auxotrophic selection marker gene such as an antibiotic or auxotrophic selection marker gene provided herein.

In still another embodiment, provided herein is a method for iteratively clearing a previously introduced plasmid from a microbial host cell, the method comprising: (a) introducing into the microbial host cell a first plasmid comprising a first selection marker gene; (b) growing the microbial host cells from step (a) in a media selective for microbial host cells expressing the selection marker gene and isolating microbial host cells from cultures derived therefrom; (c) growing the microbial host cells isolated in step (b) in media not selective for the selection marker gene and isolating microbial host cells from cultures derived therefrom; and (d) repeating steps (a)-(c) in one or more rounds, wherein each of the one or more rounds comprises introducing an additional plasmid comprising a different selection marker gene than the selection marker gene introduced in a previous round of selection, and wherein the first and the additional plasmids comprise an identical origin of replication to each other first or additional plasmid previously introduced into the microbial host cell, thereby iteratively clearing the previously introduced first or additional plasmid from a microbial host cell; wherein counterselection is not performed to facilitate clearance of a previously present plasmid. The counterselection can be via expression of an antibiotic, chemical or temperature-sensitive counter-selectable marker gene by the microbial host cell. In one embodiment, counterselection is not performed after at least one round of editing. In another embodiment, counterselection is not performed after every round of editing. In another embodiment, counterselection is not performed after any round of editing. In yet another embodiment, counterselection is performed only after alternating rounds of editing. In still another embodiment, counterselection is performed only after a final round of editing. The selection marker gene can be an antibiotic or auxotrophic selection marker gene such as an antibiotic or auxotrophic selection marker gene provided herein.

In one embodiment, the methods provided herein for clearing a plasmid from a microbial host cell further comprise genotyping the microbial host cells between each step. In one embodiment, the methods provided herein for clearing a plasmid from a microbial host cell genome can further comprise genotyping the microbial host cells between select steps. In one embodiment, the methods provided herein for clearing a plasmid from a microbial host cell genome can further comprise genotyping the microbial host cells after a final step. The genotyping can be performed to confirm the presence of the desired modification. Colony PCR can be used to screen in most cases, and restriction enzyme digest can be used to screen for the genetic edits. Genetic edits can be also confirmed by sequencing such as with any next generation sequencing method known in the art.

In one embodiment, the introducing steps of any method provided herein comprises transforming the microbial host. Transformation of the microbial host cell can be performed using any methods known in the art and/or provided herein for transforming or introducing nucleic acids into a microbial host cell. In some cases, some or all of the nucleic acids that are introduced into a microbial host cell may be introduced as part of one or more plasmids. In other cases, some or all of the nucleic acids that are introduced into a microbial host cell may be introduced as linear fragments, for example, comprising single stranded or double stranded DNA and/or RNA. Any nucleic acid present as a linear fragment, whether the linear fragment is single- or double-stranded for use in any of the methods, compositions or kits provided herein can contain one or more end modifications. The end modifications can be applied to the 5' and/or 3' ends of the linear fragment. The end modifications can be selected from a group consisting of, but not limited to: phosphorylated ends, phosphothiorate linked bases, hairpins, inverted bases, base modifications, 2' O-methyl bases, locked nucleic bases, phosphorothioated 2' O-methyl bases, and phosphorothioated locked nucleic bases.

In one embodiment, the microbial host cell utilized in any of the methods provided herein is a eukaryotic cell. The eukaryotic microbial host cell can be any eukaryotic microbial host cell provided herein. In one embodiment, the eukaryotic microbial host cell is a yeast cell or filamentous fungal cell. The yeast cell can be any yeast cell known in the art and/or provided herein. The filamentous fungal cell can be any filamentous fungal cell known in the art and/or provided herein.

In another embodiment, the microbial host cell utilized in any of the methods provided herein is a prokaryotic cell. The prokaryotic microbial host cell can be any prokaryotic microbial host cell provided herein. In one embodiment, the prokaryotic microbial host cell is a strain of *Escherichia coli* (*E. coli*). The strain of *E. coli* can be any strain known in the art and/or provided herein. For example, the *E. coli* strain can be selected from Enterotoxigenic *E. coli* (ETEC), Enteropathogenic *E. coli* (EPEC), Enteroinvasive *E. coli* (EIEC), Enterohemorrhagic *E. coli* (EHEC), Uropathogenic *E. coli* (UPEC), Verotoxin-producing *E. coli*, *E. coli* O157: H7, *E. coli* 0104:H4, *Escherichia coli* 0121, *Escherichia coli* 0104:H21, *Escherichia coli* K1, *Escherichia coli* NC101. In one embodiment, the prokaryotic microbial host cell is a species of *Bacillus* or strain thereof. The species of *Bacillus* can be any species known in the art and/or provided herein. The strain of *Bacillus* can be any strain known in the art and/or provided herein. In one embodiment, the prokaryotic microbial host cell is a species of *Corynebacterium* or strain thereof. The species of *Corynebacterium* can be any species known in the art and/or provided herein. The strain of *Corynebacterium* can be any strain known in the art and/or provided herein.

As described throughout this disclosure, the plasmids utilized in the methods provided herein can comprise selectable or selection marker genes. The selectable marker genes for use herein can be auxotrophic markers, prototrophic markers, dominant markers, recessive markers, antibiotic resistance markers, catabolic markers, enzymatic markers, fluorescent markers, luminescent markers or combinations thereof. In one embodiment, the selectable or selection marker genes are antibiotic or auxotrophic selection marker genes. The antibiotic selection markers genes can be any antibiotic selection marker genes known in the art. The antibiotic selection marker genes used in any of the plasmids utilized in the methods provided herein can be chosen based on the microbial host cell. For example, for prokaryotic host cells, the antibiotic selection marker gene can be any genes known in the art that confers resistance against ampicillin, kanamycin, tetracycline, chloramphenicol, zeocin, spectinomycin/streptomycin. For eukaryotic host cells, the antibiotic selection marker gene can be any genes known in the art that confers resistance against belomycin, phleomycin geneticin, neomycin, hygromycin, puromycin, blasticidin, zeocin. The auxotrophic selection markers genes can be any auxotrophic selection marker genes known in the art for a particular microbial host cell. The auxotrophic selection marker genes used in any of the plasmids utilized in the methods provided herein for prokaryotic cells can be selected from known amino acid auxotrophic markers. The auxotrophic selection marker genes used in any of the plasmids utilized in the methods provided herein for eukaryotic cells can be selected from yeast URA3, LYS2, LEU2, TRP1, HIS3, MET15 and ADE2 or homologs or orthologs thereof.

As described throughout this disclosure, the plasmids utilized in the methods provided herein can further comprise counter-selectable or counterselection marker genes. The counter-selectable marker genes can be genes often also referred to as "death genes" which express toxic gene products that kill producer cells. The counter-selectable marker genes for use in the methods and compositions provided herein can be any 'death genes' known in the art. In one embodiment, the counter-selectable or counterselection marker genes are antibiotic, chemical, or temperature-sensitiveselection marker genes. The counter-selectable marker genes used in any of the plasmids utilized in the methods provided herein can be chosen based on the microbial host cell. For example, for prokaryotic host cells (e.g., *E. coli* or *C. glutamicum*), the counter-selectable marker gene can be selected from sacB, rpsL(strA), tetAR, pheS, thyA, gata-1, or ccdB, the function of which is described in (Reyrat et al. 1998 "Counterselectable Markers: Untapped Tools for Bacterial Genetics and Pathogenesis." Infect Immun. 66(9): 4011-4017). For eukaryotic host cells, the counter-selectable marker genes can be selected from yeast LYS2, TRP1, MET15, URA3, URA4+ and thymidine kinase or homologs or orthologs thereof.

As described throughout this disclosure, the plasmids utilized in any round(s) of transformation and selection in the methods provided herein can each comprise an identical origin of replication. The origin of replication shared by each of the plasmids utilized in any round(s) of introducing genetic edits in the methods provided herein can be any origin of replication known in the art. The origin of replication used in any of the plasmids utilized in the methods provided herein can be chosen based on the microbial host cell. In one embodiment, the microbial host cell is a prokaryotic host cell and the origin of replication shared amongst the plasmids introduced during any round(s) of editing is any origin of replication known in the art for the particular prokaryotic host cell organism. In one embodiment, the microbial host cell is a strain of *E. coli* and the origin of replication shared amongst the plasmids introduced during any round(s) of editing is oriR, colE1, p15A, pUC, pSC101 or R6K. In one embodiment, the microbial host cell is a strain of *Bacillus* and the origin of replication shared amongst the plasmids introduced during successive rounds of editing is pE194, pBAA1 or pUB 110. In some embodiments, the R6K replication origin is conditional on the presence of the pir protein. That is, in some embodiments, the presently disclosed vectors comprising the R6K replication origin will only be amplified in host cells comprising the pir gene. In one embodiment, the microbial host cell is a strain of *Corynebacterium* and the origin of replication shared amongst the plasmids introduced during successive rounds of editing is oriR, CASE1 or CG1.

Also provided herein are compositions for use in the methods provided herein. In one embodiment, a composition for use in the methods provided herein comprises a pool of repair fragments. In one embodiment, the pool comprises a plurality of a single repair fragments. In one embodiment, the pool comprises a plurality of repair fragments such that at least one repair fragment in the pool comprises sequence for a genetic edit that is different than each other genetic edit present in each other repair fragment of the plurality of repair fragments. The plurality of repair fragments present in the pool can be at least, at most or exactly 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 different repair fragments. In one embodiment, at least one repair fragment in the plurality of repair fragments can target a locus in a nucleic acid (e.g., genome, plasmid, etc.) within a microbial host cell that is different from the locus targeted by each other repair fragment in the pool. In one embodiment, each repair fragment in the plurality of repair fragments can target a locus in a nucleic acid (e.g., genome, plasmid, etc.) within a microbial host cell that is different from the locus targeted by each other repair fragment in the pool. In one embodiment, each repair fragment in a pool present in composition provided herein comprises sequence for one genetic edit. In one embodiment, each repair fragment in a pool present in a composition provided herein comprises sequence for multiple genetic edits. Each repair fragment can comprise sequence for at least, at most or exactly 1, 2, 3, 4, 5, 6, 7, 8, 9, 10, 15, 20, 25, 30, 35, 40, 45, 50, 55, 60, 65, 70, 75, 80, 85, 90, 95, or 100 genetic edits. Each genetic edit present on a repair fragment can be selected from the group consisting of an insertion, a deletion, a single nucleotide polymorphism, a genome shuffling, a large scale deletion, a genomic edit, a plasmid edit, or multiple edits. The genetic edits can be a promoter, a degron, a terminator, a protein solubility tag or a degradation tag.

Each repair fragment in a pool present in a composition provided herein can be present as a linear fragment of nucleic acid. The linear fragment of nucleic acid can be single stranded or double stranded. The linear fragment can contain one or more end modifications. The end modifications can be applied to the 5' and/or 3' ends of the linear fragment. The end modifications can be selected from a group consisting of, but not limited to: phosphorylated ends, phosphothiorate linked bases, hairpins, inverted bases, base modifications, 2' O-methyl bases, locked nucleic bases, phosphorothioated 2' O-methyl bases, and phosphorothioated locked nucleic bases.

In one embodiment, each repair fragment in a pool present in a composition provided herein can be present within a plasmid or integron. In one embodiment, each repair fragment in a pool present in a composition provided herein can be present within a different plasmid or integron from each other repair fragment in the pool. In one embodiment, each plasmid comprising a repair fragment further comprises one or more origins of replication. The one or more origins of replication in each plasmid can be identical. In one embodiment, the plasmid comprises a first origin of replication that facilitates maintenance of the plasmid in a microbial host cell (e.g., *E. coli*) used during the cloning of the plasmid and a second origin of replication that facilitates maintenance of the plasmid in a microbial host cell (e.g., *C. glutamicum*) utilized in one of the genetic editing methods provided herein.

In one embodiment, each repair fragment or the plasmid comprising a repair fragment can further comprise sequence comprising a selection marker and/or a counter-selection marker. The selection marker genes and/or counter-selection marker genes for use herein can be auxotrophic markers, prototrophic markers, dominant markers, recessive markers, antibiotic resistance markers, catabolic markers, enzymatic markers, fluorescent markers, luminescent markers or combinations thereof. In one embodiment, the selection marker genes and/or counter-selection marker genes are antibiotic or auxotrophic selection marker genes. The antibiotic selection markers genes can be any antibiotic selection marker genes known in the art and/or provided herein. The antibiotic selection marker genes used in any of the plasmids utilized in the methods provided herein can be chosen based on the microbial host cell. In one embodiment, each repair fragment or the plasmid comprising a repair fragment in a composition as provided herein comprises the same selection marker gene as each other repair fragment or each other plasmid comprising a repair fragment.

Each of the repair fragments or the one or more genetic edits present within a repair fragment can comprise sequence complementary or homologous to a locus present in a nucleic acid (e.g., genome, plasmid, etc.) within a microbial host cell. The sequence complementary or homologous to the locus present in the nucleic acid (e.g., genome, plasmid, etc.) can be located upstream or 5' of a repair fragment or genetic edit and/or downstream or 3' of a repair fragment or a genetic edit. The sequence complementary or homologous to the locus present in the nucleic acid (e.g., genome, plasmid, etc.) that is located upstream or 5' of a repair fragment or a genetic edit can be referred to as a left homology arm, while the sequence complementary or homologous to the locus present in the nucleic acid (e.g., genome, plasmid, etc.) that is downstream or 3' of a repair fragment or a genetic edit can be referred to as a right homology arm.

In one embodiment, a composition for use in the methods provided herein comprises a pool of editing plasmids. The pool of editing plasmids can comprise at least, at most or exactly 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 different editing plasmids. Each of the editing plasmids in the pool can comprise one or more repair fragments. The one or more repair fragments present in each editing plasmid can comprise sequence for at least, at most or exactly 1, 2, 3, 4, 5, 6, 7, 8, 9, 10, 15, 20, 25, 30, 35, 40, 45, 50, 55, 60, 65, 70, 75, 80, 85, 90, 95, or 100 genetic edits. Each genetic edit present on a repair fragment can be selected from the group consisting of an insertion, a deletion, a single nucleotide polymorphism, a genome shuffling, a large scale deletion, a genomic edit, a plasmid edit, or multiple edits. The genetic edits can be a promoter, a degron, a terminator, sequence for a protein solubility tag or sequence for a degradation tag.

In one embodiment, each editing plasmid in a pool of editing plasmids in a composition as provided herein comprises a selection or selectable marker gene. In one embodiment, each editing plasmid in a pool of editing plasmids in a composition as provided herein comprises the same selection or selectable marker gene. In one embodiment, each editing plasmid in a pool of editing plasmids in a composition as provided herein comprises a counter-selection marker gene. The selection marker genes and/or counter-selection marker genes within an editing plasmid can be auxotrophic markers, prototrophic markers, dominant markers, recessive markers, antibiotic resistance markers, catabolic markers, enzymatic markers, fluorescent markers, luminescent markers or combinations thereof. In one embodiment, the selection marker genes and/or counter-selection marker genes are antibiotic or auxotrophic selection marker genes. The antibiotic selection markers genes can be any antibiotic selection marker genes known in the art and/or provided herein. The antibiotic selection marker genes used in any of the plasmids utilized in the methods provided herein can be chosen based on the microbial host cell.

In one embodiment, each editing plasmid in the pool further comprises one or more origins of replication. The one or more origins of replication in each editing plasmid can be identical. In one embodiment, the plasmid comprises a first origin of replication that facilitates maintenance of the plasmid in a microbial host cell (e.g., *E. coli*) used during the cloning of the plasmid and a second origin of replication that facilitates maintenance of the plasmid in a microbial host cell (e.g., *C. glutamicum*) utilized in one of the genetic editing methods provided herein.

In one embodiment, each repair fragments or the one or more genetic edits present within each repair fragment in an editing plasmid can comprise sequence complementary or homologous to a locus present in a nucleic acid (e.g., genome, plasmid, etc.) within a microbial host cell. The sequence complementary or homologous to the locus present in the nucleic acid (e.g., genome, plasmid, etc.) can be located upstream or 5' of a genetic edit and/or downstream or 3' of a genetic edit present on the repair fragment. The sequence complementary or homologous to the locus present in the nucleic acid (e.g., genome, plasmid, etc.) that is located upstream or 5' of a genetic edit can be referred to as a left homology arm, while the sequence complementary or homologous to the locus present in the nucleic acid (e.g., genome, plasmid, etc.) that is downstream or 3' of a genetic edit can be referred to as a right homology arm.

In one embodiment, each repair fragment or the one or more genetic edits present within each repair fragment in an editing plasmid can comprise a left and right homology arm that targets a locus in a nucleic acid (e.g., genome, plasmid, etc.) within a microbial host cell that is different from the locus targeted by each other repair fragment or the one or more genetic edits present within each other repair fragment in each other editing plasmid in the pool. In one embodiment, each repair fragment or the one or more genetic edits present within each repair fragment in an editing plasmid can comprise a left and right homology arm that targets a locus in a nucleic acid (e.g., genome, plasmid, etc.) within a microbial host cell that is the same as the loci targeted by each other or at least one repair fragment or the one or more genetic edits present within each other repair fragment in each other editing plasmid in the pool.

Any composition provided herein can further comprise a guide RNA (gRNA) paired with each genetic edit comprised in a repair fragment. Each gRNA present in any composition provided herein can comprise a CRISPR RNA (crRNA) and a trans-activating crRNA (tracrRNA). In one embodiment, each gRNA present in any composition provided herein is comprised of a single gRNA (sgRNA). The gRNA paired with a genetic edit present on a repair fragment as provided herein can target the locus in a nucleic acid (e.g., genome, plasmid, etc.) for which the genetic edit or repair fragment comprising said genetic edit comprises complementary or homologous sequence thereto and can facilitate cleavage of said locus. The gRNA paired with a genetic edit present on a repair fragment as provided herein can be present on the same plasmid (e.g., editing plasmid) or different plasmid (e.g., editing plasmid) than said genetic edit. When present on a different or separate plasmid, the plasmid comprising the gRNA can further comprise the same selection marker gene and/or counter-selection marker gene as the plasmid comprising the paired genetic edit or the repair fragment comprising the paired genetic edit. When present on a different or separate plasmid, the plasmid comprising the gRNA can further comprise the same origin(s) of replication as the plasmid comprising the paired genetic edit or the repair fragment comprising the paired genetic edit. The gRNA paired with a genetic edit present on a repair fragment as provided herein can be present on the same linear fragment (single-stranded or double-stranded) or different linear fragment (single-stranded or double-stranded) than said genetic edit. In one embodiment, a plasmid (e.g., editing plasmid) in a composition provided herein comprises one gRNA or a plurality of different gRNAs such that each gRNA is paired with a genetic edit present on a repair fragment also present in the composition. The plurality of different gRNAs can be at least, at most or exactly 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1000 different gRNAs. The genetic edit paired with each gRNA on said plasmid (e.g., editing plasmid) can also be present on said plasmid (e.g., editing plasmid). In one embodiment, a linear fragment (single-stranded or double-stranded) present in a composition provided herein comprises one gRNA or a plurality of different gRNAs such that each gRNA is paired with a genetic edit present on a repair fragment also present in the composition. The plurality of different gRNAs can be at least, at most or exactly 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, or 1000 different gRNAs. The genetic edit paired with each gRNA on said linear fragment (single-stranded or double-stranded) can also be present on said linear fragment (single-stranded or double-stranded).

In one embodiment, a composition as provided herein can further comprise a microbial host cell that comprises a site-specific endonuclease. The site-specific restriction enzyme can be any site-specific restriction enzyme known in the art. The site-specific restriction enzyme can be selected from the group consisting of an RNA-guided DNA endonuclease, a meganuclease, a transcription activator-like effector nucleases (TALEN), and a zinc-finger nuclease (ZFN). In one embodiment, the site-specific restriction enzyme is introduced into a microbial host cell or base strain thereof on a plasmid or integron. In one embodiment, the site-specific restriction enzyme is encoded on a plasmid and is introduced into the microbial host cell or base strain thereof. The site-specific restriction enzyme can be encoded on one or more editing plasmids as provided herein. In one embodiment, the site-specific restriction enzyme gene(s), one or more gRNAs, and one or more repair fragments can be present on one or more editing plasmids as provided herein. In one embodiment, the site-specific restriction enzyme is encoded on an integron and is introduced into the microbial host cell or base strain thereof. In one embodiment, the site-specific restriction enzyme is encoded in the genome. In one embodiment, the site-specific restriction enzyme is translated from RNA. In one embodiment, the site-specific restriction enzyme is introduced into the cell as protein.

In one embodiment, the site-specific restriction enzyme is an RNA-guided DNA endonuclease. The RNA guided DNA endonuclease can be a Class 2 CRISPR-Cas System RNA guided endonuclease. The Class 2 CRISPR-Cas system RNA guided DNA endonuclease is a Type II, Type V or Type VI RNA guided endonuclease. In one embodiment, the CRISPR-Cas system RNA guided DNA endonuclease is selected from Cas9, Cas12a, Cas12b, Cas12c, Cas12d, Cas12e, Cas13a, Cas13b, Cas13c, Cpf1, and MAD7 or homologs, orthologs, mutants, variants or modified versions thereof. In one embodiment, the RNA-guided DNA endonuclease is introduced into a microbial host cell or base strain thereof on a plasmid or integron. In one embodiment, the RNA-guided DNA endonuclease is encoded on an integron and is introduced into the microbial host cell or base strain thereof. In one embodiment, the RNA-guided DNA endonuclease is encoded on a plasmid and is introduced into the microbial host cell or base strain thereof. The RNA-guided DNA endonuclease can be encoded on one or more editing plasmids as provided herein. In one embodiment, the RNA-guided DNA endonuclease gene(s), one or more gRNAs, and one or more repair fragments can be present on one or more editing plasmids as provided herein.

In one embodiment, the microbial host cell for use in any of the compositions provided can further comprise a set of proteins from one or more recombination systems. The recombination system can be selected from a lambda red recombination system, a RecET recombination system, a Red/ET recombination system, any homologs, orthologs or paralogs of proteins from a lambda red recombination system or a RecET recombination system, or any combination thereof. In one embodiment, the set of proteins are from the lambda red recombination system and comprise a beta protein, a gam protein, and an exo protein. In one embodiment, the set of proteins from the recombination system is introduced into the microbial host cell on a plasmid or integron comprising genes encoding the set of proteins from the recombination system prior to step (a) in any of the methods provided herein. In another embodiment, the set of proteins from the recombination system is stably and/or constitutively expressed by the microbial host cell due to integration of genes encoding the set of proteins from the heterologous recombination system into the microbial host cell's genome. In one embodiment, the set of proteins from the recombination system is present in an operon operably linked to an inducible promoter. The inducible promoter can be any promoter known in the art that is inducible by the addition or of a reagent or by a change in temperature. The reagent can be selected from the group consisting of arabinose, isopropyl beta-D-1-thiogalactopyranoside (IPTG), and tetracycline. Examples of inducible promoters for use in the methods and compositions provided herein can include the IPTG-inducible lac promoter and the arabinose-inducible pBAD promoter. In one embodiment, the set of proteins from the recombination system is present in an operon operably linked to a repressible promoter. The repressible promoter can be any promoter known in the art that is inducible by the removal of a reagent. Examples of repressible promoters for use in the methods and compositions provided herein can include the trp promoter and the reagent can be tryptophan. The one or more recombination systems can be heterologous to the microbial host cell.

Applications

The compositions and editing methods provided herein can have a wide variety of applications, permitting, for example, the design of pathways within microbial host cells for the synthesis of desired products of interest or optimization of one or more sequences whose gene products play a role in the synthesis or expression of a desired product. The compositions and editing methods provided herein can also be used to generate optimized sequences of a gene or expression thereof or to combine one or more functional domains or motifs of protein encoded by a gene. The gene can be part of a biochemical or metabolic pathway. The biochemical or metabolic pathway can produce a desired product of interest.

The desired product of interest can be any molecule that can be assembled in a cell culture, eukaryotic or prokaryotic expression system or in a transgenic animal or plant. The iterative editing methods provided herein and compositions for use therein can be used to generate microbial host cells or libraries thereof that have altered genes and/or metabolic pathways. The iterative editing methods provided herein and compositions for use therein can be used to generate microbial host cells or libraries thereof that produce a product of interest and/or possesses desired characteristics with respect to a product of interest. The desired characteristics can be high production levels of desired products of interest, enhanced functionality of the product of interest, or decreased functionality (if that is advantageous). An additional step in any of the methods provided herein can entail screening the resultant microbial host cell or libraries thereof for the presence of desired characteristics or product(s) of interest. Such screening may be done by high throughput methods, which may be robotic/automated as provided herein.

Thus, the editing methods provided herein may be employed in a wide variety of contexts to produce or engineer microbial host cells to produce desired products of interest. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a host cell, such as a microbial enzyme, including catalase, amylase, protease, pectinase, glucose isomerase, cellulase, hemicellulase, lipase, lactase, streptokinase, and many others. The intracellular component may also include recombinant proteins, such as insulin, hepatitis B vaccine, interferon, granulocyte colony-stimulating factor, streptokinase and others. The product of interest may also refer to a protein of interest.

Recombination Systems

In one aspect provided herein, the methods provided herein for iteratively editing a genetic element (e.g., genome, cosmid, or plasmid) of a microbial host cell can entail the use of a homologous recombination system in a microbial host cell. The homologous recombination system can be native to the host cell or introduced to the cell host. Genes for the homologous recombination system can be introduced on a plasmid, introduced on a linear DNA fragment, introduced as and translated from RNA or set of RNAs or introduced as a protein or set of proteins.

In one embodiment, the use of homologous recombination (e.g., native homologous recombination) in a method for iteratively editing the genome of a microbial host cell can utilize a pool of plasmids in each round of a multi-round method. Each plasmid in the pool can comprise sequence homologous (e.g. left and right homology arms) to a region in a nucleic acid (e.g., genome, plasmid, etc.) such that the left and right homology arms are separated by a designed genetic edit (e.g. promoter or other sequence insertion, substitution, SNP, terminator, degron, sequence for a tag, sequence for a degradation signal or deletion). Other features of each of the plasmids in the pool can include a selectable marker gene (e.g. auxotrophic or antibiotic selection marker gene as provided herein), a counter selectable marker gene or genes (e.g. SacB or PheS, that confer toxicity in the presence of sucrose and 4-chloro-phenylalanine, respectively), and an origin of replication (e.g., R6K). Each plasmid from the pool of plasmids utilized in each round of the iterative editing method can possess the same origin of replication. Each plasmid from the pool of plasmids utilized in one round of the iterative editing method can possess the same origin of replication as each plasmid from the pool of plasmids utilized in each other round of the iterative editing method Loop-in/Loop-Out Once each plasmid comprising the homology arms and sequence for a genetic edit is generated, they can be mixed or pooled in a defined ratio (e.g., equimolar) and introduced into the microbial host cell using any of the methods provided herein (e.g., transformation via electroporation, conjugation, etc.). In one embodiment, each round of the multi-round iterative method comprises two or more pools of plasmids. In embodiments where each round comprises two or more pools of plasmids, the pools can be mixed in a defined (e.g., equimolar) ratios.

Following transformation, the resulting transformants can be allowed to recover. Recovery conditions (e.g., time and temperature) can be selected to minimize or lessen the probability of generating bias in the pooled library (e.g. some edited strains may using the editing method may be more or less frequent and/or grow faster or slower than other edited or non-edited strains).

Following recovery, the resulting transformants in each round of a multi-round iterative editing method can be plated on a medium to select for transformants expressing the selectable marker gene utilized in the specific round. The recombination of a plasmid comprising homology arms with a targeted locus in a nucleic acid (e.g., genome, plasmid, etc.) can occur at one of the two homology sites targeted by the homology arms present on the plasmid and that flank the designed genetic edit.

The resulting transformants that have grown as colonies on the selective medium can then be scraped from the selective medium, diluted, and plated on a second type of selective medium (e.g. counter-selectable medium). This step can allow for the induction and selection of cells (and then colonies) whose nucleic acid (e.g., genome, plasmid, etc.) that possesses the targeted loci went through a second recombination event at either the left or right homology arm. If the second recombination event occurred at the same homology arm as the first recombination event, the starting strain can be recreated. If the second recombination event occurred at the second recombination site, the resulting transformant can comprise the desired genetic edit. Thus, the population of colonies growing on the counterselection medium comprises both unedited strains and a mixture of edited strains, each containing one of the edits included in the plasmid pool introduced in the specific round of editing.

As provided herein, removal of the pool of plasmids introduced in a specific round of a multi-round iterative editing method can be facilitated by growing the transformants in media that is not selective for the selection marker gene expressing by transformants in the specific round.

As provided herein confirmation and/or identification of desired genetic edit(s) in a transformant or strain generated by an iterative editing method utilizing homologous recombination as provided herein can be achieved by genotyping said transformant or strain following selection and/or counterselection. Genotyping can be performed using PCR and/or next-generation sequencing as provided herein.

In some embodiments, the present disclosure teaches methods of looping out selected regions of DNA from the host organisms. The looping out method can be as described in Nakashima et al. 2014 "Bacterial Cellular Engineering by Genome Editing and Gene Silencing." Int. J. Mol. Sci. 15(2), 2773-2793. Looping out deletion techniques are known in the art, and are described in (Tear et al. 2014 "Excision of Unstable Artificial Gene-Specific inverted Repeats Mediates Scar-Free Gene Deletions in *Escherichia coli*." Appl. Biochem. Biotech. 175:1858-1867). The looping out methods used in the methods provided herein can be performed using single-crossover homologous recombination. In one embodiment, looping out of selected regions can entail using single-crossover homologous recombination.

In one embodiment, a composition, method or a kit provided herein comprises or utilizes repair fragments that comprise homology arms (e.g., left/right homology arms) and sequence for a genetic edit located therebetween such that said repair fragments are each located on a plasmid that can serve as loop out vectors. In one embodiment, single-crossover homologous recombination is used between a loop-out vector comprising a repair fragment comprising homology arms and sequence for a genetic edit located therebetween and the host cell genome in order to loop-in said vector. The sequence of the genetic edit within the loop-out vector can be designed with a sequence, which is a direct repeat of an existing or introduced nearby host sequence, such that the direct repeats flank the region of DNA slated for looping and deletion. Once inserted, cells containing the loop out plasmid or vector can be counter selected for deletion of the selection region.

In one aspect provided herein, the methods provided herein for iteratively editing a genetic element (e.g., genome, cosmid, or plasmid) of a microbial host cell can entail the use of sets of proteins from one or more recombination systems. Said recombination systems can be endogenous to the microbial host cell or can be introduced heterologously. The sets of proteins of the one or more heterologous recombination systems can be introduced as nucleic acids (e.g., as plasmid, linear DNA or RNA, or integron) and be integrated into the genome of the host cell or be stably expressed from an extrachromosomal element. The sets of proteins of the one or more heterologous recombination systems can be introduced as RNA and be translated by the host cell. The sets of proteins of the one or more heterologous recombination systems can be introduced as proteins into the host cell. The sets of proteins of the one or more recombination systems can be from a lambda red recombination system, a RecET recombination system, a Red/ET recombination system, any homologs, orthologs or paralogs of proteins from a lambda red recombination system, a RecET recombination system, or Red/ET recombination system or any combination thereof. The recombination methods and/or sets of proteins from the RecET recombination system can be any of those as described in Zhang Y., Buchholz F., Muyrers J. P. P. and Stewart A. F. "A new logic for DNA engineering using recombination in *E. coli*." Nature Genetics 20 (1998) 123-128; Muyrers, J. P. P., Zhang, Y., Testa, G., Stewart, A. F. "Rapid modification of bacterial artificial chromosomes by ET-recombination." Nucleic Acids Res. 27 (1999) 1555-1557; Zhang Y., Muyrers J. P. P., Testa G. and Stewart A. F. "DNA cloning by homologous recombination in *E. coli*." Nature Biotechnology 18 (2000) 1314-1317 and Muyrers J P et al., "Techniques: Recombinogenic engineering—new options for cloning and manipulating DNA" Trends Biochem Sci. 2001 May; 26(5):325-31, which are herein incorporated by reference. The sets of proteins from the Red/ET recombination system can be any of those as described in Rivero-Müller, Adolfo et al. "Assisted large fragment insertion by Red/ET-recombination (ALFIRE)—an alternative and enhanced method for large fragment recombineering" Nucleic acids research vol. 35,10 (2007): e78, which is herein incorporated by reference.

As provided herein, the genetic edits that can be introduced singly or pools using the iterative editing methods provided herein can comprise control elements (e.g., promoters, terminators, solubility tags, degradation tags or degrons), modified forms of genes (e.g., genes with desired SNP(s)), antisense nucleic acids, and/or one or more genes that are part of a metabolic or biochemical pathway. In one embodiment, the modification entails one or more deletions, for example to inactivate a single gene or a plurality of genes. In one embodiment, the modification entails gene editing of the host cell. The gene editing can entail editing the genome of the host cell and/or a separate genetic element present in the host cell such as, for example, a plasmid or cosmid.

Lambda RED Mediated Recombination

In one aspect provided herein, the methods provided herein for editing a nucleic acid (e.g., genome, cosmid, or plasmid) of a microbial host cell can entail the use of a set of proteins from the lambda red-mediated recombination system. The use of lambda red-mediated homologous recombination in any of the methods provided herein can be as described by Datsenko and Wanner, PNAS USA 97:6640-6645 (2000), the contents of which are hereby incorporated by reference in their entirety. The set of proteins from the lambda red recombination system can comprise the exo, beta or gam proteins or any combination thereof. Gam can prevent both the endogenous RecBCD and SbcCD nucleases from digesting linear DNA introduced into a microbial host cell, while exo is a 5'→3' dsDNA-dependent exonuclease that can degrade linear dsDNA starting from the 5' end and generate 2 possible products (i.e., a partially dsDNA duplex with single-stranded 3' overhangs or a ssDNA whose entire complementary strand was degraded) and beta can protect the ssDNA created by Exo and promote its annealing to a complementary ssDNA target in the cell. Beta expression can be required for lambda red based recombination with an ssDNA oligo substrate as described at blog.addgene.org/lambda-red-a-homologous-recombination-based-technique-for-genetic-engineering, the contents of which are herein incorporated by reference.

In one embodiment, the editing methods provided herein are implemented in a microbial host cell that already stably expresses lambda red recombination genes such as the DY380 strain described at blog.addgene.org/lambda-red-a-homologous-recombination-based-technique-for-genetic-engineering, the contents of which are herein incorporated by reference. Other bacterial strains that comprise components of the lambda red recombination system and can be utilized in any of the methods provided herein can be found in Thomason et al (Recombineering: Genetic Engineering in Bacteria Using Homologous Recombination. Current Protocols in Molecular Biology. 106:V:1.16:1.16.1-1.16.39) and Sharan et al (Recombineering: A Homologous Recombination-Based Method of Genetic Engineering. Nature protocols. 2009; 4(2):206-223), the contents of each of which are herein incorporated by reference.

As provided herein, the set of proteins of the lambda red recombination system can be introduced into the microbial host cell prior to implementation of any of the editing methods provided herein. Genes for each of the proteins of the lambda red recombination system can be introduced on nucleic acids (e.g., as plasmids, linear DNA or RNA, a mini-λ, a lambda red prophage or integrons) and be integrated into the genome of the host cell or expressed from an extrachromosomal element. In some cases, each of the components (i.e., exo, beta, gam or combinations thereof) of the lambda red recombination system can be introduced as an RNA and be translated by the host cell. In some cases, each of the components (i.e., exo, beta, gam or combinations thereof) of the lambda red recombination system can be introduced as a protein into the host cell.

In one embodiment, genes for the set of proteins of the lambda red recombination system are introduced on a plasmid. The set of proteins of the lambda red recombination system on the plasmid can be under the control of a promoter such as, for example, the endogenous phage pL promoter. In one embodiment, the set of proteins of the lambda red recombination system on the plasmid is under the control of an inducible promoter. The inducible promoter can be inducible by the addition or depletion of a reagent or by a change in temperature. In one embodiment, the set of proteins of the lambda red recombination system on the plasmid is under the control of an inducible promoter such as the IPTG-inducible lac promoter or the arabinose-inducible pBAD promoter. A plasmid expressing genes for the set of proteins of the lambda red recombination system can also express repressors associated with a specific promoter such as, for example, the lacI, araC or cI857 repressors associated with the IPTG-inducible lac promoter, the arabinose-inducible pBAD promoter and the endogenous phage pL promoters, respectively.

In one embodiment, genes for the set of proteins of the lambda red recombination system are introduced on a mini-λ, which a defective non-replicating, circular piece of phage DNA, that when introduced into microbial host cell, integrates into the genome as described at blog.addgene.org/lambda-red-a-homologous-recombination-based-technique-for-genetic-engineering, the contents of which are herein incorporated by reference.

In one embodiment, genes for the set of proteins of the lambda red recombination system are introduced on a lambda red prophage, which can allow for stable integration of the lambda red recombination system into a microbial host cell such as described at blog.addgene.org/lambda-red-a-homologous-recombination-based-technique-for-genetic-engineering, the contents of which are herein incorporated by reference.

In one embodiment, any of the methods provided herein for editing a microbial host genome comprising a set of proteins from the lambda red recombination system utilizes repair fragments alone or in pairs with a gRNA such that each repair fragment and/or paired gRNA is present as a linear fragment of DNA. The linear fragment of DNA can be ssDNA or dsDNA. The linear fragments comprising a repair fragment and/or gRNA can further comprise a selectable marker gene and/or a counter-selectable marker gene. The use of either a dsDNA or ssDNA linear fragment can be dependent on the size or length of the repair fragment or gRNA. For example, a dsDNA linear fragment can be utilized when a repair fragment comprises a genetic edit (e.g., insertion or deletion) that is greater than about 20 nucleotides, while ssDNA linear fragments can be utilized when a repair fragment comprises a genetic edit (e.g., insertion or deletion) that is less than about 20 nucleotides.

As provided herein, a repair fragment or genetic edit present on a repair fragment can comprise homology arms that comprise sequence complementary or homologous to a locus in a nucleic acid (e.g., genome, plasmid, etc.) present within a microbial host cell. The homology arms present on a repair fragment or flanking a genetic edit can each be between 1 and 5, between 5 and 10, between 10 and 20, between 20 and 30, between 30 and 40, between 40 and 50, between 50 and 60, between 60 and 70, between 70 and 80, between 80 and 90, between 90 and 100, between 100 and 125, between 125 and 150, between 150 and 175 or between 175 and 200 nucleotides in length, inclusive of the endpoints. The homology arms present on a repair fragment or flanking a genetic edit can each be at least, at most or exactly 1, 2, 3, 4, 5, 6, 7, 8, 9, 10, 11 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 nucleotides in length.

CRISPR Mediated Gene Editing

In one aspect provided herein, the methods provided herein for iteratively editing a nucleic acid (e.g., genome, cosmid, or plasmid) of a microbial host cell can entail the use of CRISPR. As provided herein, the RNA-guided DNA endonucleases of the CRISPR/Cas system can be introduced into the microbial host cell prior to implementation of the iterative editing method. The RNA-guided DNA endonucleases of the CRISPR/Cas system can be introduced on nucleic acids (e.g., as plasmids, linear DNA or RNA, or integrons) and be integrated into the genome of the host cell or expressed from an extrachromosomal element. The RNA-guided DNA endonucleases of the CRISPR/Cas system can be introduced as an RNA and be translated by the host cell. The RNA-guided DNA endonucleases of the CRISPR/Cas system can be introduced as a protein into the host cell.

The CRISPR/Cas system is a prokaryotic immune system that confers resistance to foreign genetic elements such as those present within plasmids and phages and that provides a form of acquired immunity. CRISPR stands for Clustered Regularly Interspaced Short Palindromic Repeat, and cas stands for CRISPR-associated system, and refers to the small cas genes associated with the CRISPR complex.

CRISPR-Cas systems are most broadly characterized as either Class 1 or Class 2 systems. The main distinguishing feature between these two systems is the nature of the Cas-effector module. Class 1 systems require assembly of multiple Cas proteins in a complex (referred to as a "Cascade complex") to mediate interference, while Class 2 systems use a large single Cas enzyme to mediate interference. Each of the Class 1 and Class 2 systems are further divided into multiple CRISPR-Cas types based on the presence of a specific Cas protein. For example, the Class 1 system is divided into the following three types: Type I systems, which contain the Cas3 protein; Type III systems, which contain the Cas10 protein; and the putative Type IV systems, which contain the Csf1 protein, a Cas8-like protein. Class 2 systems are generally less common than Class 1 systems and are further divided into the following three types: Type II systems, which contain the Cas9 protein; Type V systems, which contain Cas12a protein (previously known as Cpf1, and referred to as Cpf1 herein), Cas12b (previously known as C2c1), Cas12c (previously known as C2c3), Cas12d (previously known as CasY), and Cas12e (previously known as CasX); and Type VI systems, which contain Cas13a (previously known as C2c2), Cas13b, and Cas13c. Pyzocha et al., ACS Chemical Biology, Vol. 13 (2), pgs. 347-356. In one embodiment, the CRISPR-Cas system for use in the methods provided herein is a Class 2 system. In one embodiment, the CRISPR-Cas system for use in the methods provided herein is a Type II, Type V or Type VI Class 2 system. In one embodiment, the CRISPR-Cas system for use in the methods provided herein comprises a component selected from Cas9, Cas12a, Cas12b, Cas12c, Cas12d, Cas12e, Cas13a, Cas13b, Cas13c or homologs, orthologs or paralogs thereof. In one embodiment, the CRISPR-Cas system for use in the methods provided herein comprises Cpf1, or homologs, orthologs or paralogs thereof. In one embodiment, the CRISPR-Cas system for use in the methods provided herein comprises MAD7, or homologs, orthologs or paralogs thereof.

CRISPR systems used in methods disclosed herein comprise a Cas effector module comprising one or more nucleic acid (e.g., RNA) guided CRISPR-associated (Cas) nucleases, referred to herein as Cas effector proteins. In some embodiments, the Cas proteins can comprise one or multiple nuclease domains. A Cas effector protein can target single stranded or double stranded nucleic acid molecules (e.g. DNA or RNA nucleic acids) and can generate double strand or single strand breaks. In some embodiments, the Cas effector proteins are wild-type or naturally occurring Cas proteins. In some embodiments, the Cas effector proteins are mutant Cas proteins, wherein one or more mutations, insertions, or deletions are made in a WT or naturally occurring Cas protein (e.g., a parental Cas protein) to produce a Cas protein with one or more altered characteristics compared to the parental Cas protein.

In some instances, the Cas protein is a wild-type (WT) nuclease. Non-limiting examples of suitable Cas proteins for use in the present disclosure include C2c1, C2c2, C2c3, Cas1, Cas1B, Cas2, Cas3, Cas4, Cas5, Cas6, Cas7, Cas8, Cas9 (also known as Csn1 and Csx12), Cas10, Cpf1, Csy1, Csy2, Csy3, Cse1, Cse2, Csc1, Csc2, Csa5, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx100, Csx16, CsaX, Csx3, Csx1, Csx15, Csf1, Csf2, Csf3, Csf4, MAD1-20, SmCsm1, homologs thereof, orthologues thereof, variants thereof, mutants thereof, or modified versions thereof. Suitable nucleic acid guided nucleases (e.g., Cas9) can be from an organism from a genus, which includes but is not limited to: *Thiomicrospira, Succinivibrio, Candidatus, Porphyromonas, Acidomonococcus, Prevotella, Smithella, Moraxella, Synergistes, Francisella, Leptospira, Catenibacterium, Kandleria, Clostridium, Dorea, Coprococcus, Enterococcus, Fructobacillus, Weissella, Pediococcus, Corynebacter, Sutterella, Legionella, Treponema, Roseburia, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Alicyclobacillus, Brevibacilus, Bacillus, Bacteroidetes, Brevibacilus, Carnobacterium, Clostridiaridium, Clostridium, Desulfonatronum, Desulfovibrio, Helcococcus, Leptotrichia, Listeria, Methanomethyophilus, Methylobacterium, Opitutaceae, Paludibacter, Rhodobacter, Sphaerochaeta, Tuberibacillus,* and *Campylobacter*. Species of organism of such a genus can be as otherwise herein discussed.

Suitable nucleic acid guided nucleases (e.g., Cas9) can be from an organism from a phylum, which includes but is not limited to Firmicute, Actinobacteria, Bacteroidetes, Proteobacteria, Spirochates, and Tenericutes. Suitable nucleic acid guided nucleases can be from an organism from a class, which includes but is not limited to Erysipelotrichia, Clostridia, Bacilli, Actinobacteria, Bacteroidetes, Flavobacteria, Alphaproteobacteria, Betaproteobacteria, Gammaproteobacteria, Deltaproteobacteria, Epsilonproteobacteria, Spirochaetes, and Mollicutes. Suitable nucleic acid guided nucleases can be from an organism from an order, which includes but is not limited to Clostridiales, Lactobacillales, Actinomycetales, Bacteroidales, Flavobacteriales, Rhizobiales, Rhodospirillales, Burkholderiales, Neisseriales, Legionellales, Nautiliales, Campylobacterales, Spirochaetales, Mycoplasmatales, and Thiotrichales. Suitable nucleic acid guided nucleases can be from an organism from within a family, which includes but is not limited to: Lachnospiraceae, Enterococcaceae, Leuconostocaceae, Lactobacillaceae, Streptococcaceae, Peptostreptococcaceae, Staphylococcaceae, Eubacteriaceae, Corynebacterineae, Bacteroidaceae, *Flavobacterium,* Cryomoorphaceae, Rhodobiaceae, Rhodospirillaceae, Acetobacteraceae, Sutterellaceae, Neisseriaceae, Legionellaceae, Nautiliaceae, Campylobacteraceae, Spirochaetaceae, Mycoplasmataceae, and Francisellaceae.

Other nucleic acid guided nucleases (e.g., Cas9) suitable for use in the methods, systems, and compositions of the present disclosure include those derived from an organism such as, but not limited to: *Thiomicrospira* sp. XS5, *Eubacterium rectale, Succinivibrio dextrinosolvens, Candidatus methanoplasma termitum, Candidatus methanomethylophilus alvus, Porphyromonas crevioricanis, Flavobacterium branchiophilum, Acidomonococcus* sp., Lachnospiraceae bacterium COE1, *Prevotella brevis* ATCC 19188, *Smithella* sp. SCADC, *Moraxella bovoculi, Synergistes jonesii, Bacteroidetes* oral taxon 274, *Francisella tularensis, Leptospira inadai serovar* Lyme str. 10, *Acidomonococcus* sp. crystal structure (5B43) *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis, Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2 4417, *Smithella* sp. SCADC, *Microgenomates, Acidaminococcus* sp. BV3L6, Lachnospiraceae bacterium MA2020, *Candidatus methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens, Porphyromonas macacae, Catenibacterium* sp. CAG:290, *Kandleria vitulina*, Clostridiales bacterium KA00274, Lachnospiraceae bacterium 3-2, *Dorea longicatena, Coprococcus catus* GD/7, *Enterococcus columbae* DSM 7374, *Fructobacillus* sp. EFB-N1, *Weissella halotolerans, Pediococcus acidilactici, Lactobacillus curvatus, Streptococcus pyogenes, Lactobacillus versmoldensis*, and *Filifactor alocis* ATCC 35896. See, U.S. Pat. Nos. 8,697,359; 8,771,945; 8,795,965; 8,865,406; 8,871,445; 8,889,356; 8,895,308; 8,906,616; 8,932,814; 8,945,839; 8,993,233; 8,999,641; 9,822,372; 9,840,713; U.S. patent application Ser. No. 13/842,859 (US 2014/0068797 A1); U.S. Pat. Nos. 9,260,723; 9,023,649; 9,834,791; 9,637,739; U.S. patent application Ser. No. 14/683,443 (US 2015/0240261 A1); U.S. patent application Ser. No. 14/743,764 (US 2015/0291961 A1); U.S. Pat. Nos. 9,790,490; 9,688,972; 9,580,701; 9,745,562; 9,816,081; 9,677,090; 9,738,687; U.S. application Ser. No. 15/632,222 (US 2017/0369879 A1); U.S. application Ser. No. 15/631, 989; U.S. application Ser. No. 15/632,001; and U.S. Pat. No. 9,896,696, each of which is herein incorporated by reference.

In some embodiments, a Cas effector protein comprises one or more of the following activities:

a nickase activity, i.e., the ability to cleave a single strand of a nucleic acid molecule;

a double stranded nuclease activity, i.e., the ability to cleave both strands of a double stranded nucleic acid and create a double stranded break;

an endonuclease activity;

an exonuclease activity; and/or a helicase activity, i.e., the ability to unwind the helical structure of a double stranded nucleic acid.

In aspects of the disclosure the term "guide nucleic acid" refers to a polynucleotide comprising 1) a guide sequence capable of hybridizing to a target sequence (referred to herein as a "targeting segment") and 2) a scaffold sequence capable of interacting with (either alone or in combination with a tracrRNA molecule) a nucleic acid guided nuclease as described herein (referred to herein as a "scaffold segment"). A guide nucleic acid can be DNA. A guide nucleic acid can be RNA. A guide nucleic acid can comprise both DNA and RNA. A guide nucleic acid can comprise modified non-naturally occurring nucleotides. In cases where the guide nucleic acid comprises RNA, the RNA guide nucleic acid can be encoded by a DNA sequence on a polynucleotide molecule such as a plasmid, linear construct generated using the methods and compositions provided herein.

In some embodiments, the guide nucleic acids described herein are RNA guide nucleic acids ("guide RNAs" or "gRNAs") and comprise a targeting segment and a scaffold segment. In some embodiments, the scaffold segment of a gRNA is comprised in one RNA molecule and the targeting segment is comprised in another separate RNA molecule. Such embodiments are referred to herein as "double-molecule gRNAs" or "two-molecule gRNA" or "dual gRNAs." In some embodiments, the gRNA is a single RNA molecule and is referred to herein as a "single-guide RNA" or an "sgRNA." The term "guide RNA" or "gRNA" is inclusive, referring both to two-molecule guide RNAs and sgRNAs.

The DNA-targeting segment of a gRNA comprises a nucleotide sequence that is complementary or homologous to a sequence in a target nucleic acid sequence. The target nucleic acid sequence can be a locus in a genetic element such as a genome or plasmid. As such, the targeting segment of a gRNA interacts with a target nucleic acid in a sequence-specific manner via hybridization (i.e., base pairing), and the nucleotide sequence of the targeting segment determines the location within the target DNA that the gRNA will bind. The degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 75, or more nucleotides in length. In some embodiments, a guide sequence is less than about 75, 50, 45, 40, 35, 30, 25, 20 nucleotides in length. In aspects, the guide sequence is 10-30 nucleotides long. The guide sequence can be 15-20 nucleotides in length. The guide sequence can be 15 nucleotides in length. The guide sequence can be 16 nucleotides in length. The guide sequence can be 17 nucleotides in length. The guide sequence can be 18 nucleotides in length. The guide sequence can be 19 nucleotides in length. The guide sequence can be 20 nucleotides in length.

The scaffold segment of a guide RNA interacts with a one or more Cas effector proteins to form a ribonucleoprotein complex (referred to herein as a CRISPR-RNP or a RNP-complex). The guide RNA directs the bound polypeptide to a specific nucleotide sequence within a target nucleic acid sequence via the above-described targeting segment. The scaffold segment of a guide RNA comprises two stretches of nucleotides that are complementary to one another and which form a double stranded RNA duplex. Sufficient sequence within the scaffold sequence to promote formation of a targetable nuclease complex may include a degree of complementarity along the length of two sequence regions within the scaffold sequence, such as one or two sequence regions involved in forming a secondary structure. In some cases, the one or two sequence regions are comprised or encoded on the same polynucleotide. In some cases, the one or two sequence regions are comprised or encoded on separate polynucleotides. Optimal alignment may be determined by any suitable alignment algorithm, and may further account for secondary structures, such as self-complementarity within either the one or two sequence regions. In some embodiments, the degree of complementarity between the one or two sequence regions along the length of the shorter of the two when optimally aligned is about or more than about 25%, 30%, 40%, 50%, 60%, 70%, 80%, 90%, 95%, 97.5%, 99%, or higher. In some embodiments, at least one of the two sequence regions is about or more than about 5, 6, 7, 8, 9, 10, 11, 12, 13, 14, 15, 16, 17, 18, 19, 20, 25, 30, 40, 50, or more nucleotides in length.

A scaffold sequence of a subject gRNA can comprise a secondary structure. A secondary structure can comprise a pseudoknot region or stem-loop structure. In some examples, the compatibility of a guide nucleic acid and nucleic acid guided nuclease is at least partially determined by sequence within or adjacent to the secondary structure region of the guide RNA. In some cases, binding kinetics of a guide nucleic acid to a nucleic acid guided nuclease is determined in part by secondary structures within the scaffold sequence. In some cases, binding kinetics of a guide nucleic acid to a nucleic acid guided nuclease is determined in part by nucleic acid sequence with the scaffold sequence.

A compatible scaffold sequence for a gRNA-Cas effector protein combination can be found by scanning sequences adjacent to a native Cas nuclease loci. In other words, native Cas nucleases can be encoded on a genome within proximity to a corresponding compatible guide nucleic acid or scaffold sequence.

Nucleic acid guided nucleases can be compatible with guide nucleic acids that are not found within the nucleases endogenous host. Such orthogonal guide nucleic acids can be determined by empirical testing. Orthogonal guide nucleic acids can come from different bacterial species or be synthetic or otherwise engineered to be non-naturally occurring. Orthogonal guide nucleic acids that are compatible with a common nucleic acid-guided nuclease can comprise one or more common features. Common features can include sequence outside a pseudoknot region.

Common features can include a pseudoknot region. Common features can include a primary sequence or secondary structure.

A guide nucleic acid can be engineered to target a desired target sequence by altering the guide sequence such that the guide sequence is complementary or homologous to the target sequence, thereby allowing hybridization between the guide sequence and the target sequence. A guide nucleic acid with an engineered guide sequence can be referred to as an engineered guide nucleic acid. Engineered guide nucleic acids are often non-naturally occurring and are not found in nature.

In one embodiment, the repair fragments comprising one or more genetic edits as provided herein that are introduced in each round the iterative editing methods provided herein serve as donor DNA and each genetic edit on each repair fragment is paired with a gRNA. Each gRNA can comprise sequence targeting a specific sequence at a locus in a genetic element (e.g., chromosome or plasmid) within the host cell. The donor DNA sequence can be used in combination with its paired guide RNA (gRNA) in a CRISPR method of gene editing using homology directed repair (HDR). The CRISPR complex can result in the strand breaks within the target gene(s) that can be repaired by using homology directed repair (HDR). HDR mediated repair can be facilitated by co-transforming the host cell with a donor DNA sequence generated using the methods and compositions provided herein. The donor DNA sequence can comprise a desired genetic perturbation (e.g., deletion, insertion (e.g., promoter, terminator, solubility or degradation tag), and/or single nucleotide polymorphism) as well as targeting sequences or homology arms that comprise sequence complementary or homologous to the sequence or locus targeted by the gRNA. In this embodiment, the CRISPR complex cleaves the target gene specified by the one or more gRNAs. The donor DNA sequence can then be used as a template for the homologous recombination machinery to incorporate the desired genetic perturbation into the host cell. The donor DNA can be single-stranded, double-stranded or a double-stranded plasmid. The donor DNA can lack a PAM sequence or comprise a scrambled, altered or non-functional PAM in order to prevent re-cleavage. In some cases, the donor DNA can contain a functional or non-altered PAM site. The mutated or edited sequence in the donor DNA (also flanked by the regions of homology) prevents re-cleavage by the CRISPR-complex after the mutation(s) has/have been incorporated into the genome. In some embodiments, homologous recombination is facilitated through the use or expression of sets of proteins from one or more recombination systems either endogenous to the host cell or introduced heterologously.

Host Cells

The compositions and methods provided herein for the iterative editing of genetic elements (e.g., genome or plasmid) of a host cell to generate or produce a desired trait or phenotype (e.g., production of a product of interest as provided herein) in said host cell can be applicable to any organism where desired traits or phenotypes can be identified in a population of genetic mutants. The organism can be a microorganism or higher eukaryotic organism.

Thus, as used herein, the term "microorganism" should be taken broadly. It includes, but is not limited to, the two prokaryotic domains, Bacteria and Archaea, as well as certain eukaryotic fungi and protists. However, in certain aspects, "higher" eukaryotic organisms such as insects, plants, and animals can be utilized in the methods taught herein.

Suitable host cells include, but are not limited to: bacterial cells, algal cells, plant cells, fungal cells, insect cells, and mammalian cells. In one illustrative embodiment, suitable host cells include an *Escherichia coli* (*E. coli*) strain or a *Bacillus* strain.

Other suitable host organisms of the present disclosure include microorganisms of the genus *Corynebacterium*. In some embodiments, preferred *Corynebacterium* strains/species include: *C. efficiens*, with the deposited type strain being DSM44549, *C. glutamicum*, with the deposited type strain being ATCC13032, and *C. ammoniagenes*, with the deposited type strain being ATCC6871. In some embodiments, the preferred host of the present disclosure is *C. glutamicum*.

Suitable host strains of the genus *Corynebacterium*, in particular of the species *Corynebacterium glutamicum*, are in particular the known wild-type strains: *Corynebacterium glutamicum* ATCC13032, *Corynebacterium acetoglutamicum* ATCC15806, *Corynebacterium acetoacidophilum* ATCC13870, *Corynebacterium melassecola* ATCC17965, *Corynebacterium thermoaminogenes* FERM BP-1539, *Brevibacterium flavum* ATCC14067, *Brevibacterium lactofermentum* ATCC13869, and *Brevibacterium divaricatum* ATCC14020; and L-amino acid-producing mutants, or strains, prepared therefrom, such as, for example, the L-lysine-producing strains: *Corynebacterium glutamicum* FERM-P 1709, *Brevibacterium flavum* FERM-P 1708, *Brevibacterium lactofermentum* FERM-P 1712, *Corynebacterium glutamicum* FERM-P 6463, *Corynebacterium glutamicum* FERM-P 6464, *Corynebacterium glutamicum* DM58-1, *Corynebacterium glutamicum* DG52-5, *Corynebacterium glutamicum* DSM5714, and *Corynebacterium glutamicum* DSM12866.

The term "*Micrococcus glutamicus*" has also been in use for *C. glutamicum*. Some representatives of the species *C. efficiens* have also been referred to as *C. thermoaminogenes* in the prior art, such as the strain FERM BP-1539, for example.

In some embodiments, the microbial host cell of the present disclosure is a eukaryotic cell. Suitable eukaryotic host cells include, but are not limited to: fungal cells, algal cells, insect cells, animal cells, and plant cells. Suitable fungal host cells include, but are not limited to: *Ascomycota, Basidiomycota, Deuteromycota, Zygomycota, Fungi imperfecti*. Certain preferred fungal host cells include yeast cells and filamentous fungal cells. Suitable filamentous fungi host cells include, for example, any filamentous forms of the subdivision *Eumycotina* and *Oomycotai*. (see, e.g., Hawksworth et al., In Ainsworth and Bisby's Dictionary of The Fungi, 8$^{th}$ edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungi host cells are morphologically distinct from yeast.

In certain illustrative, but non-limiting embodiments, the filamentous fungal host cell may be a cell of a species of: *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella*, or teleomorphs, or anamorphs, and synonyms or taxonomic equivalents thereof. In one embodiment, the filamentous fungus is selected from the group consisting of *A. nidulans, A. oryzae, A. sojae*, and *Aspergilli* of the *A. niger* Group. In a preferred embodiment, the filamentous fungus is *Aspergillus niger*.

In one embodiment, the filamentous fungus is a production strain selected from *Aspergillus foetidus* ACM 3996 (=FRR 3558), *Magnaporthe grisea* Guy-11 or *Phanerochaete chrysosporium* RP78. In a separate embodiment, the filamentous fungus is an *A. niger* production strain known in the art. Examples of *A. niger* production strains for use in the methods provided herein can include *A. niger* ATCC 11414, ATCC 1015, ACM 4992 (=ATCC 9142), ACM 4993 (=ATCC 10577), ACM 4994 (=ATCC 12846), ATCC26550, ATCC 11414, N402, CBS 513.88 or NRRL3 (ATCC 9029, CBS 120.49).

Suitable yeast host cells can include, but are not limited to: *Candida, Hansenula, Saccharomyces, Schizosaccharomyces, Pichia, Kluyveromyces*, and *Yarrowia*. In some embodiments, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia Jinlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

In certain embodiments, the microbial host cell is an algal such as, *Chlamydomonas* (e.g., *C. reinhardtii*) and *Phormidium* (P. sp. ATCC29409).

In other embodiments, the microbial host cell is a prokaryotic cell. Suitable prokaryotic cells include gram positive, gram negative, and gram-variable bacterial cells. The microbial host cell may be a species or strain of, but not limited to: *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia*, and *Zymomonas*.

In some embodiments, the microbial host strain is a bacterial industrial strain. Numerous bacterial industrial strains are known and suitable in the methods and compositions described herein.

In some embodiments, the bacterial host cell is of the *Agrobacterium* species (e.g., *A. radiobacter, A. rhizogenes, A. rubi*), the *Arthrobacter* species (e.g., *A. aurescens, A. citreus, A. globformis, A. hydrocarboglutamicus, A. mysorens, A. nicotianae, A. paraffineus, A. protophonniae, A. roseoparaffinus, A. sulfureus, A. ureafaciens*), the *Bacillus* species (e.g., *B. thuringiensis, B. anthracis, B. megaterium, B. subtilis, B. lentus, B. circulars, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. In some embodiments, the host cell will be an industrial *Clostridium* species (e.g., *C. acetobutylicum, C. tetani* E88, *C. lituseburense, C. saccharobutylicum, C. perfringens, C. beijerinckii*). In some embodiments, the host cell will be an industrial *Corynebacterium* species (e.g., *C. glutamicum, C. acetoacidophilum*). In some embodiments, the host cell will be an industrial *Escherichia* species (e.g., *E. coli*). In some embodiments, the host cell will be an industrial *Erwinia* species (e.g., *E. uredovora, E. carotovora, E. ananas, E. herbicola, E. punctata, E. terreus*). In some embodiments, the host cell will be an industrial *Pantoea* species (e.g., *P. citrea, P. agglomerans*). In some embodiments, the host cell will be an industrial *Pseudomonas* species, (e.g., *P. putida, P. aeruginosa, P. mevalonii*). In some embodiments, the host cell will be an industrial *Streptococcus* species (e.g., *S. equisimiles, S. pyogenes, S. uberis*). In some embodiments, the host cell will be an industrial *Streptomyces* species (e.g., *S. ambofaciens, S. achromogenes, S. avermitilis, S. coelicolor, S. aureofaciens, S. aureus, S. fungicidicus, S. griseus, S. lividans*). In some embodiments, the host cell will be an industrial *Zymomonas* species (e.g., *Z. mobilis, Z. lipolytica*), and the like.

In some embodiments, the bacterial host cell is of the *E. coli* species and can comprise: Enterotoxigenic *E. coli* (ETEC), Enteropathogenic *E. coli* (EPEC), Enteroinvasive *E. coli* (EIEC), Enterohemorrhagic *E. coli* (EHEC), Uropathogenic *E. coli* (UPEC), Verotoxin-producing *E. coli*, E. coli O157:H7, E. coli 0104:H4, Escherichia coli 0121, Escherichia coli 0104:H21, Escherichia coli K1, and Escherichia coli NC101. In some embodiments, the microbial host cell for the genomic engineering methods provided herein is selected from E. coli K12, E. coli B, and E. coli C.

In some embodiments, the microbial host cell for the genomic engineering methods provided herein is selected from E. coli strains NCTC 12757, NCTC 12779, NCTC 12790, NCTC 12796, NCTC 12811, ATCC 11229, ATCC 25922, ATCC 8739, DSM 30083, BC 5849, BC 8265, BC 8267, BC 8268, BC 8270, BC 8271, BC 8272, BC 8273, BC 8276, BC 8277, BC 8278, BC 8279, BC 8312, BC 8317, BC 8319, BC 8320, BC 8321, BC 8322, BC 8326, BC 8327, BC 8331, BC 8335, BC 8338, BC 8341, BC 8344, BC 8345, BC 8346, BC 8347, BC 8348, BC 8863, and BC 8864.

In some embodiments, the microbial host cell for the genomic engineering methods provided herein is a verocytotoxigenic E. coli (VTEC), such as strains BC 4734 (O26:H11), BC 4735 (O157:H−), BC 4736, BC 4737 (n.d.), BC 4738 (O157:H7), BC 4945 (O26:H−), BC 4946 (O157:H7), BC 4947 (O111:H−), BC 4948 (O157:H), BC 4949 (O5), BC 5579 (O157:H7), BC 5580 (O157:H7), BC 5582 (O3:H), BC 5643 (O2:H5), BC 5644 (O128), BC 5645 (O55:H−), BC 5646 (O69:H−), BC 5647 (O101:H9), BC 5648 (O103:H2), BC 5850 (O22:H8), BC 5851 (O55:H−), BC 5852 (O48:H21), BC 5853 (O26:H11), BC 5854 (O157:H7), BC 5855 (O157:H−), BC 5856 (O26:H−), BC 5857 (O103:H2), BC 5858 (O26:H11), BC 7832, BC 7833 (O raw form:H−), BC 7834 (ONT:H−), BC 7835 (O103:H2), BC 7836 (O57:H−), BC 7837 (ONT:H−), BC 7838, BC 7839 (O128:H2), BC 7840 (O157:H−), BC 7841 (O23:H−), BC 7842 (O157:H−), BC 7843, BC 7844 (O157:H−), BC 7845 (O103:H2), BC 7846 (O26:H11), BC 7847 (O145:H−), BC 7848 (O157:H−), BC 7849 (O156:H47), BC 7850, BC 7851 (O157:H−), BC 7852 (O157:H−), BC 7853 (O5:H−), BC 7854 (O157:H7), BC 7855 (O157:H7), BC 7856 (O26:H−), BC 7857, BC 7858, BC 7859 (ONT:H−), BC 7860 (O129:H−), BC 7861, BC 7862 (O103:H2), BC 7863, BC 7864 (O raw form:H−), BC 7865, BC 7866 (O26:H−), BC 7867 (O raw form:H−), BC 7868, BC 7869 (ONT:H−), BC 7870 (O113:H−), BC 7871 (ONT:H−), BC 7872 (ONT:H−), BC 7873, BC 7874 (O raw form:H−), BC 7875 (O157:H−), BC 7876 (O111:H−), BC 7877 (O146:H21), BC 7878 (O145:H−), BC 7879 (O22:H8), BC 7880 (O raw form:H−), BC 7881 (O145:H−), BC 8275 (O157:H7), BC 8318 (O55:K−:H−), BC 8325 (O157:H7), and BC 8332 (ONT), BC 8333.

In some embodiments, the microbial host cell for the genomic engineering methods provided herein is an enteroinvasive E. coli (EIEC), such as strains BC 8246 (O152:K−:H−), BC 8247 (O124:K(72):H3), BC 8248 (O124), BC 8249 (O112), BC 8250 (O136:K(78):H−), BC 8251 (O124:H−), BC 8252 (O144:K−:H−), BC 8253 (O143:K:H−), BC 8254 (O143), BC 8255 (O112), BC 8256 (O28a.e), BC 8257 (O124:H−), BC 8258 (O143), BC 8259 (O167:K−:H5), BC 8260 (O128a.c.:H35), BC 8261 (O164), BC 8262 (O164:K−:H−), BC 8263 (O164), andBC 8264 (O124).

In some embodiments, the microbial host cell for the genomic engineering methods provided herein is an enterotoxigenic E. coli (ETEC), such as strains BC 5581 (O78:H11), BC 5583 (O2:K1), BC 8221 (O118), BC 8222 (O148:H−), BC 8223 (O111), BC 8224 (O110:H−), BC 8225 (O148), BC 8226 (O118), BC 8227 (O25:H42), BC 8229 (O6), BC 8231 (O153:H45), BC 8232 (O9), BC 8233 (O148), BC 8234 (O128), BC 8235 (O118), BC 8237 (O111), BC 8238 (O110:H17), BC 8240 (O148), BC 8241 (O6H16), BC 8243 (O153), BC 8244 (O15:H−), BC 8245 (O20), BC 8269 (O125a.c:H−), BC 8313 (O6:H6), BC 8315 (O153:H−), BC 8329, BC 8334 (O118:H12), and BC 8339.

In some embodiments, the microbial host cell for the genomic engineering methods provided herein is an enteropathogenic E. coli (EPEC), such as strains BC 7567 (O86), BC 7568 (O128), BC 7571 (O114), BC 7572 (O119), BC 7573 (O125), BC 7574 (O124), BC 7576 (O127a), BC 7577 (O126), BC 7578 (O142), BC 7579 (O26), BC 7580 (OK26), BC 7581 (O142), BC 7582 (O55), BC 7583 (O158), BC 7584 (O−), BC 7585 (O−), BC 7586 (O−), BC 8330, BC 8550 (O26), BC 8551 (O55), BC 8552 (O158), BC 8553 (O26), BC 8554 (O158), BC 8555 (O86), BC 8556 (O128), BC 8557 (OK26), BC 8558 (O55), BC 8560 (O158), BC 8561 (O158), BC 8562 (O114), BC 8563 (O86), BC 8564 (O128), BC 8565 (O158), BC 8566 (O158), BC 8567 (O158), BC 8568 (O111), BC 8569 (O128), BC 8570 (O114), BC 8571 (O128), BC 8572 (O128), BC 8573 (O158), BC 8574 (O158), BC 8575 (O158), BC 8576 (O158), BC 8577 (O158), BC 8578 (O158), BC 8581 (O158), BC 8583 (O128), BC 8584 (O158), BC 8585 (O128), BC 8586 (O158), BC 8588 (O26), BC 8589 (O86), BC 8590 (O127), BC 8591 (O128), BC 8592 (O114), BC 8593 (O114), BC 8594 (O114), BC 8595 (O125), BC 8596 (O158), BC 8597 (O26), BC 8598 (O26), BC 8599 (O158), BC 8605 (O158), BC 8606 (O158), BC 8607 (O158), BC 8608 (O128), BC 8609 (O55), BC 8610 (O114), BC 8615 (O158), BC 8616 (O128), BC 8617 (O26), BC 8618 (O86), BC 8619, BC 8620, BC 8621, BC 8622, BC 8623, BC 8624 (O158), and BC 8625 (O158).

In some embodiments, the microbial host cell for the genomic engineering methods provided herein is a Shigella organism, including Shaigella flexneri, Shigella dysenteriae, Shigella boydii, and Shigella sonnei.

In some embodiments, the bacterial host cell for use in the iterative editing methods provided herein is any strain or sub-species of a Bacillus species known in the art and/or selected from B. subtilis, B. wakoensis, B. amylolyticus, B. hemicellulosilyticus, B. cellulosilyticus, B. akibai, B. mannanilyticus, B. anthracis, B. cereus, B. mycoides, B. thuringiensis, B. megaterium, B. pumilus, B. licheniformis, B. circulans, B. coagulans, B. alvei, B. brevis, B. macerans, B. amyloliquefaciens and B. sphaericus.

In some embodiments, the microbial host cell for the genomic engineering methods provided herein is an alkaliphilic Bacillus strain, such as strains O-4 (=JCM 9137=DSM 2514), N-1 (=JCM 9140=DSM 2521), 17-1 (=JCM 9142=DSM 2524), 27-1 (=JCM 9144=DSM 2520), 13 (=JCM 9145=DSM 2523), K-12-5 (=JCM 9149), 202-1 (=JCM 9151), C-11 (=JCM 9152=DSM 16731), D-6 (=JCM 9154), 2b-2 (=JCM 9155), N-4T (=JCM 9156=DSM 2522), 1139T (=JCM 9157=ATCC 43226), IC (=JCM 9158), KX-6 (=JCM 9159), H−167 (=JCM 9160), 199 (=JCM 9163), C-3 (=JCM 9164), S-2 (=JCM 9166), AM-001 (=JCM 10596=DSM 16130) and 8-1 (=JCM 10598).

In various embodiments, strains that may be used in the practice of the disclosure including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Transformation of Host Cells

In some embodiments, the constructs utilized in the iterative editing methods of the present disclosure may be introduced into the microbial host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., 1986 "Basic Methods in Molecular Biology"). Other methods of transformation include for example, lithium acetate transformation and electroporation See, e.g., Gietz et al., Nucleic Acids Res. 27:69-74 (1992); Ito et al., J. Bacterol. 153:163-168 (1983); and Becker and Guarente, Methods in Enzymology 194:182-187 (1991). In some embodiments, transformed host cells are referred to as recombinant host strains.

Automation

In one embodiment, the compositions and methods provided herein are incorporated into a high-throughput (HTP) method for genetic engineering of a microbial host cell. In another embodiment, the methods provided herein can be implemented using one or more of the molecular tools that are part of the suite of HTP molecular tool sets described in PCT/US18/36360, PCT/US18/36333 or WO 2017/100377, each of which is herein incorporated by reference, for all purposes, to create genetically engineered microbial host cells with a desired trait or phenotype. Examples of libraries that can be generated using the methods provided herein to iteratively edit the genome of a microbial host cell can include, but are not limited to promoter ladders, terminator ladders, solubility tag ladders or degradation tag ladders. Examples of high-throughput genomic engineering methods for which the methods provided herein can be adapted can include, but are not limited to, promoter swapping, terminator (stop) swapping, solubility tag swapping, degradation tag swapping or SNP swapping as described in PCT/US18/36360, PCT/US18/36333 or WO 2017/100377. The high-throughput methods can be automated and/or utilize robotics and liquid handling platforms (e.g., plate robotics platform and liquid handling machines known in the art. The high-throughput methods can utilize multi-well plates such as, for example microtiter plates.

In some embodiments, the automated methods of the disclosure comprise a robotic system. The systems outlined herein are generally directed to the use of 96- or 384-well microtiter plates, but as will be appreciated by those in the art, any number of different plates or configurations may be used. In addition, any or all of the steps outlined herein may be automated; thus, for example, the systems may be completely or partially automated. The robotic systems compatible with the methods and compositions provided herein can be those described in PCT/US18/36360, PCT/US18/36333 or WO 2017/100377.

Kits

Also provided by the present disclosure are kits for practicing the methods for iterative editing of or clearing of plasmids from microbial host cells or generating libraries derived therefrom as described above. The kit can comprise a mixture containing all of the reagents (e.g., plasmids comprising repair fragments and/or gRNAs; base microbial host cells) necessary for performing said methods. In one embodiment, a subject kit may contain: (i) a pool of first plasmids comprising a first repair fragment comprising a genetic edit and a selection marker gene, (ii) one or more additional pools of plasmids such that each additional pool of plasmids comprises an additional repair fragment comprising a sequence for an additional genetic edit and a different selection marker gene than the selection marker gene introduced in a previous plasmid, and (iii) optionally, a microbial host cell.

In one embodiment, a subject kit may contain: (i) a pool of first repair fragments comprising sequence for a genetic edit and a selection marker gene, (ii) a first guide RNA (gRNA) paired with the genetic edit present on the first repair fragment, (iii) one or more additional repair fragments such that each additional repair fragments comprises sequence for a genetic edit and a different selection marker gene than the selection marker gene introduced in a previous repair fragment, (iv) an additional gRNA for each additional repair fragment, and (v) optionally, a microbial host cell. In one embodiment, each repair fragment and its paired gRNA is present on the same plasmid. In one embodiment, each repair fragment and its paired gRNA are present on separate plasmids. In one embodiment, each repair fragment and its paired gRNA is present on the same linear fragment of nucleic acid. In one embodiment, each repair fragment and its paired gRNA are present on separate linear fragments of nucleic acid.

In some cases, the kit further includes reagents for genotyping (e.g., reagents for colony PCR and/or restriction fragment analysis) and/or phenotype testing edited microbial host cells.

In one embodiment, the kits provided herein further comprise nucleic acids (e.g., as plasmids, linear DNA or RNA, or integrons) encoding sets of proteins for a heterologous recombination system for introducing the heterologous recombination system into the microbial host cell. In one embodiment, the kits provided herein further comprise sets of proteins for a heterologous recombination system for introducing the heterologous recombination system into the microbial host cell. The heterologous recombination system can be selected from a lambda red recombination system, a RecET recombination system, a Red/ET recombination system, any homologs, orthologs or paralogs of proteins from a lambda red recombination system, Red/ET recombination system or a RecET recombination system, or any combination thereof.

In a separate embodiment, the kits provided herein further comprise nucleic acids (e.g., as plasmids, linear DNA or RNA, or integrons) encoding a site-specific restriction enzyme for introducing the site-specific restriction enzyme into a microbial host cell. In one embodiment, the kits provided herein further comprise a site-specific restriction enzyme for introducing the site-specific restriction enzyme into a microbial host cell. The site-specific restriction enzyme can be selected from the group consisting of an RNA-guided DNA endonuclease, a meganuclease, a transcription activator-like effector nucleases (TALEN), and a zinc-finger nuclease (ZFN). In one embodiment, site-specific restriction endonuclease is an RNA-guided DNA endonuclease cleaves a sequence at the first locus in the genome of the microbial host cell. The RNA-guided DNA endonuclease can be selected from Cas9, Cas12a, Cas12b, Cas12c, Cas12d, Cas12e, Cas13a, Cas13b, Cas13c, Cpf1, or homologs, orthologs or paralogs thereof.

The components of the kit may be combined in one container, or each component may be in its own container. For example, the components of the kit may be combined in a single reaction tube or in one or more different reaction tubes.

In addition to above-mentioned components, the subject kit further includes instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded.

EXAMPLES

The present invention is further illustrated by reference to the following Examples. However, it should be noted that these Examples, like the embodiments described above, are illustrative and are not to be construed as restricting the scope of the invention in any way.

Figure 6:
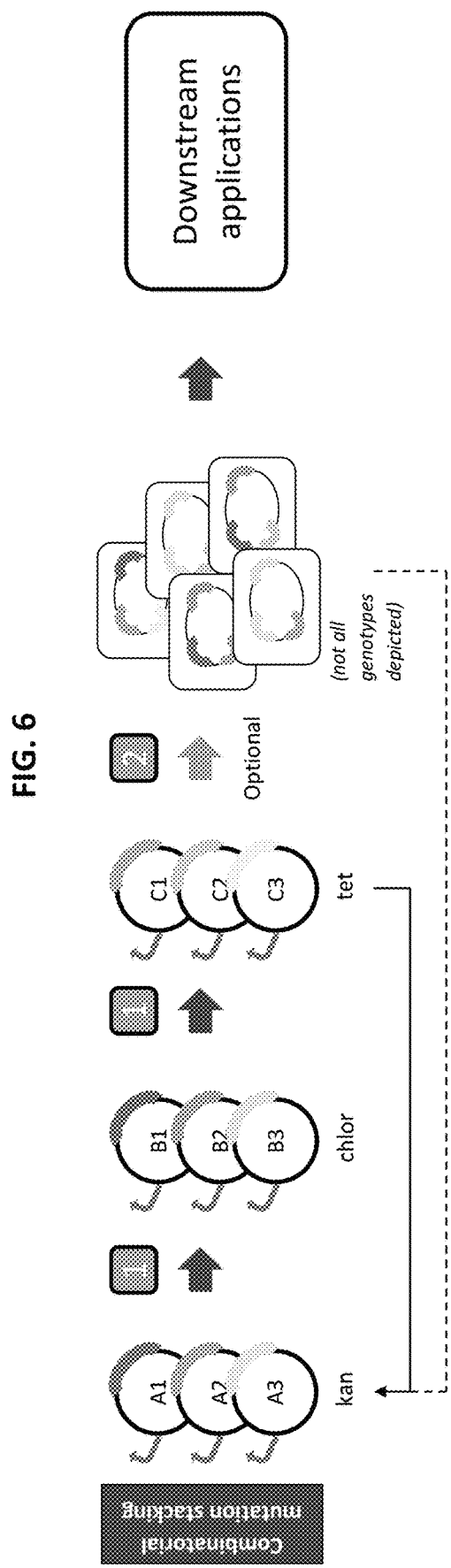
FIG. 6 depicts a workflow schematic for an embodiment of iterative and pooled iterative CRISPR genomic editing as provided herein and detailed in Example 4.

Example 1—Proof of Principle of Method for Iterative Editing of a Microbial Host Cell Genome Via CRISPR that does not Require Use of Counterselection Markers for Each Round of Editing Objective This example describes the use of a CRISPR mediated method for stacking multiple genomic edits in the genome of a microbial host cell without requiring the use of counterselectable markers in each round of editing. The general workflow of the method employed in this example is shown in FIG. 1 and entailed introducing a genetic edit at one of 3 separate genomic loci in each of 3 successive rounds of genomic editing in a microbial host strain (i.e., an E. coli strain) comprising CRISPR/Cas9 and lambda red recombination machinery. The genetic edits for each of the 3 separate genomic loci were each present on a separate construct that also comprised a selectable marker gene (i.e., neomycin phosphotransferase II (KanR), chloramphenicol acetyl transferase (ChlorR), or tetracycline efflux transporter (TetR)) and each of the constructs was introduced into the microbial host strain singly. In the first round, a KanR plasmid was transformed into the microbial host cell and transformants were selected for via growth on kanamycin-containing media (Kan). Antibiotic-resistant transformants were then separately picked from the plate (a subset was be genotyped), cultured overnight in media that did not select for the KanR plasmid and prepped for the second round of transformation. In the second round of transformation, ChlorR plasmids were transformed into the transformants selected from the first round and selected for via growth on chloramphenicol-containing media (CMP). The same cycle occurred for the third round of TetR plasmids in transformants selected from the second round. After transformation of the TetR plasmids, a round of counterselection may be optionally applied to actively clear out any remaining plasmids in the population of cells (e.g., "2" in FIGS. 1 and 6). As shown in FIGS. 1 and 6, counterselection was either passive or active. Passive counterselection ('1' in FIGS. 1 and 6) between rounds 1 and 2 and rounds 2 and 3 was mediated by releasing transformants from antibiotic selection (i.e., growth on non-selective media). In the absence of antibiotic selection pressure, plasmids compete for replication machinery (i.e., proteins) resulting in loss from the cell. Active counterselection ('2' in FIGS. 1 and 6) after round 3 may be mediated through use of a marker such as sacB or pheS present in the sgRNA/repair fragment plasmids.

Materials and Methods

A Cas9/lambda-red plasmid comprising a Cas9 gene operably linked to the native Cas9 promoter and a set of proteins from the lambda red recombination system (i.e., beta, gam and exo) in an operon operably linked to an arabinose inducible promoter was constructed using cloning methods known in the art. The Cas9/lambda-red plasmid was then transformed into an E. coli W3110 strain.

In order to carry-out and test the efficacy of the iterative CRISPR editing workflow shown in FIG. 1, 3 sets of sgRNA/repair fragment plasmids were constructed. The first set of sgRNA/repair fragment plasmids (i.e., KanR plasmids) had an sgRNA cassette under the control of the pR promoter that targeted the cadA gene in the E. coli strain, a deletion cassette for introducing a 893 bp deletion in the cadA gene, a neomycin phosphotransferase II gene for conferring kanamycin resistance to successfully transformed E. coli host cells and an origin of replication for maintenance in the E. coli host cell. The second set of sgRNA/repair fragment plasmids (i.e., ChlorR plasmids) had an sgRNA cassette under the control of the pR promoter that targeted the maeA gene in the E. coli strain, a deletion cassette for introducing a 1375 bp deletion in the maeA gene, a chloramphenicol acetyl transferase gene for conferring chloramphenicol resistance to successfully transformed E. coli host cells and the same origin of replication for maintenance in the E. coli host cell as the first set of sgRNA/repair fragment plasmids. The third set of sgRNA/repair fragment plasmids (i.e., tetR plasmids) had an sgRNA cassette under the control of the pR promoter that targeted the maeB gene in the E. coli strain, a deletion cassette for introducing a 1543 bp deletion in the maeB gene, a tetracycline efflux transporter gene for conferring tetracycline resistance to successfully transformed E. coli host cells and the same origin of replication for maintenance in the E. coli host cell as the first and second sets of sgRNA/repair fragment plasmids. All sets of sgRNA/repair fragment plasmids also had a sacB gene to enable counterselection on sucrose containing growth media.

Following preparation of each of the 3 sets of sgRNA/repair fragment plasmids, the KanR plasmids were transformed into the base E. coli W3110 strain containing the Cas9/lambda red plasmid which had a beta-lactamase gene for conferring resistance to carbenicillin and the resulting round 1 transformants were selected via growth on kanamycin and carbenicillin containing growth plates. Growth on each of the selective media plates was for a period until individual colonies became pickable, which was typically overnight. Several Kan and Clin resistant colonies were then picked for genotyping of the desired edit, patched on selective media to determine presence of KanR, ClinR, or TetR plasmids, and grown overnight in media containing carbenicillin to select only for the Cas9/lambda red plasmid (see FIG. 2). Competent cells were made from the overnight culture derived from the round 1 transformants and the resulting competent round 1 transformants containing Cas9/lambda red plasmid and KanR plasmids were transformed with the ChlorR plasmids and round 2 transformants were selected for via growth on chloramphenicol and carbenicillin containing plates. Several Chlor and Clin resistant colonies were then picked for genotyping of the desired edit, patched on selective media to determine presence of KanR, ClinR, or TetR plasmids, and grown overnight in media containing carbenicillin to select only for the Cas9/lambda red plasmid (see FIG. 2). Competent cells were made from the overnight cultures derived from the round 2 transformants and the resulting competent round 2 transformants containing Cas9/lambda red plasmid and ChlorR plasmids (a subset may also contain KanR plasmids) were transformed with the TetR plasmids. Round 3 transformants were selected for via growth on tetracycline and carbenicillin containing plates. Several TetR and ClinR resistant colonies were picked and genotyped for the edits from rounds 1, 2, and 3 (see FIG. 4) and patched on selective media to determine presence of KanR, ClinR, or TetR plasmids (see FIG. 2). It should be noted that if a modified *E. coli* strain comprising each of the genetic edits introduced during the protocol and lacking all of the previously introduced sgRNA/repair fragment plasmids, the colonies can be grown overnight in media containing an appropriate amount of counterselection agent (e.g., 5% sucrose; see FIGS. 1 and 6).

Results

One of the goals of this example was to test whether or not a first selectable marker containing plasmid would be cleared or removed from a microbial host cell harboring said first selectable marker containing plasmid via introduction of and selection for a second selectable marker containing plasmids. Loss of the first selectable marker containing plasmid by introduction of and selection for the second selectable marker containing plasmid in this so-called 'passive' counterselection process was hypothesized to occur due to the lack of selection for the first selectable marker containing plasmid as well as competition for DNA replication machinery. As shown in FIG. 2, loss of previously introduced selectable marker containing plasmids from host cells did indeed occur. In particular, FIG. 2 showed an example of plasmid clearance via transformation with new plasmids containing different antibiotic selection markers with identical origins of replication. This is shown in particular in the photograph of petri dishes in the bottom row on the right hand side of FIG. 2, where cells strongly expressed the tetR plasmids, but clearly lost both the ChlorR plasmids and KanR plasmids introduced in the earlier transformations.

Figure 3:
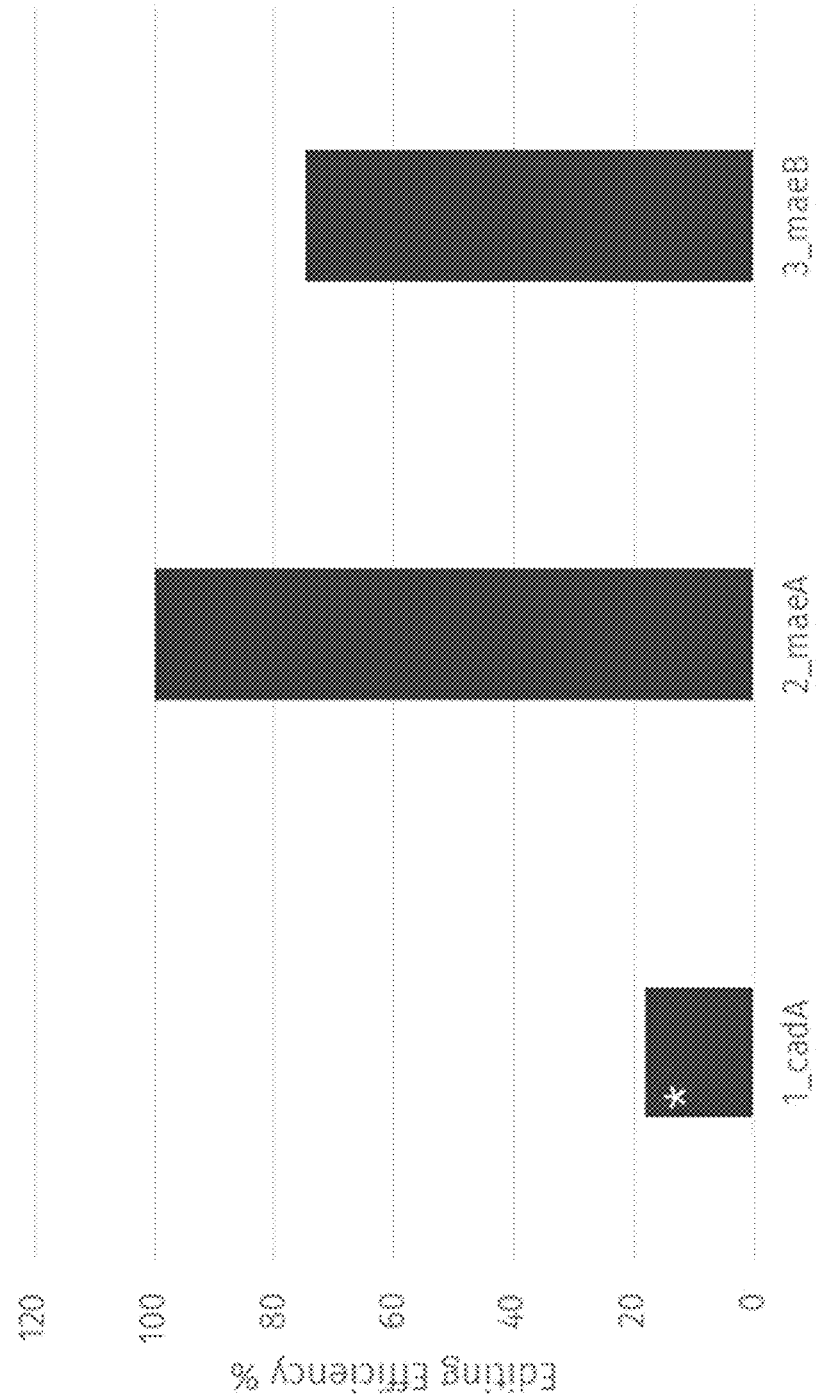
FIG. 3 illustrates editing efficiencies of iterative editing transformations. Transformation 1 (i.e., 1_cadA) resulted in 18% editing efficiency in W3110 (46 replicates screened). Transformation 2 (2 maeA) resulted in 100% editing efficiency in W3110 (6 replicates screened). Transformation 3 (3 maeB) resulted in 75% editing efficiency in W3110 (16 replicates screened). *cadA deletion is thought to be potentially toxic, leading to lower editing efficiency (this was observed in multiple experiments in various conditions).
Figure 4:
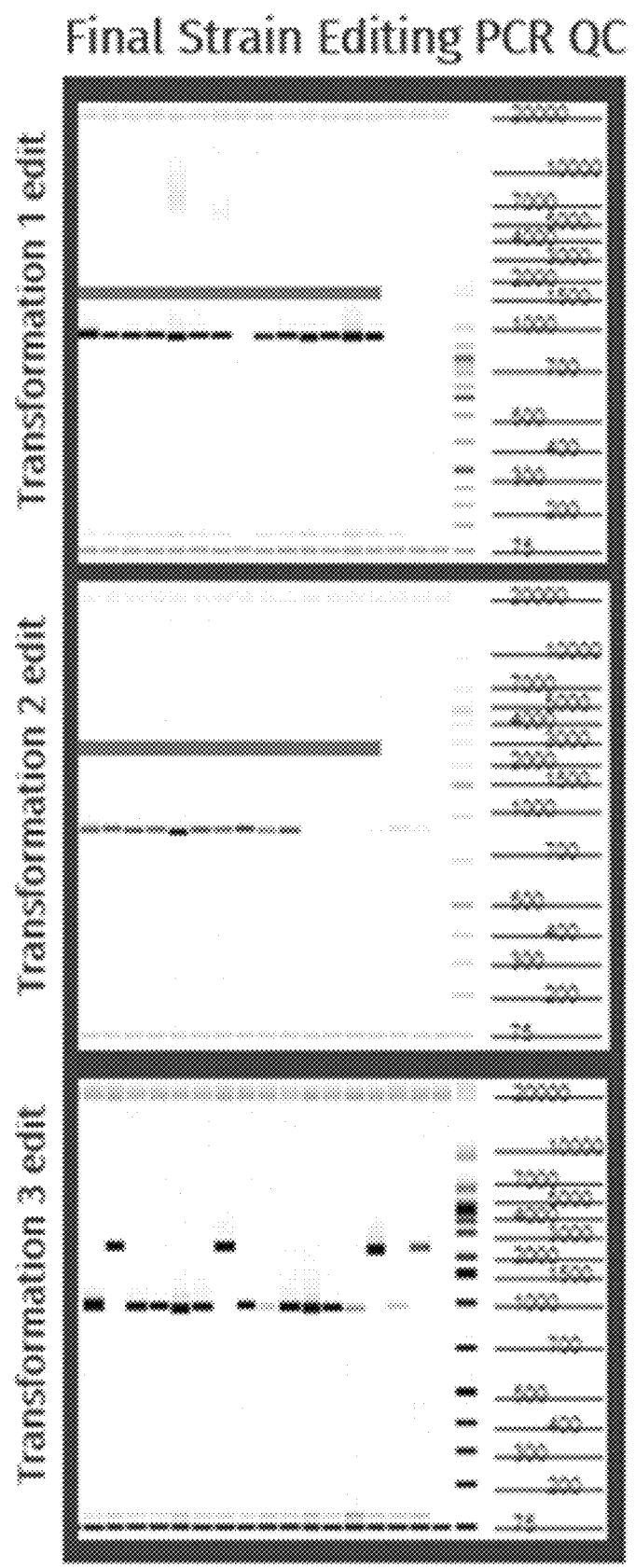
FIG. 4 illustrates colony PCR reactions screening for *E. coli* colonies after round 3 of iterative stacking. Wild type band size superimposed in gray for transformation edits 1 and 2. Top panel—cadA: WT=1826 bp, cadA deletion=933 bp, Middle panel—maeA: WT=2256 bp, maeA deletion=881 bp, Bottom panel—maeB: WT=2590 bp, maeB deletion=1047 bp.

While the plasmids introduced into the microbial host strain were progressively lost with each new transformation and selection (see FIG. 2), the genetic edits (deletions in the cadA, maeA and maeB genes) introduced into the host cell on each plasmid were clearly efficacious as seen by the images of the gels run on colony PCR reactions from *E. coli* colonies after the 3 rounds of transformation in FIG. 4. In particular, FIG. 4 showed the presence of the cadA, maeA and maeB deletions in individual colonies following the 3 successive rounds of transformations with the sets of sgRNA repair fragment plasmids described herein. It should be noted that the editing efficiency did vary between successive rounds of transformations as shown in FIG. 3; however, the variable editing efficiency may be function of the loci targeted and/or the genetic edit introduced thereto. For example, the cadA deletion may be toxic, which could account for the lower editing efficiency of this round of transformations.

Overall, the results presented herein clearly demonstrated that iterative stacking of genetic edits in microbial host cells can be performed without requiring active expression and utilization of a counter-selectable marker in each round of editing, as provided throughout this disclosure.

Example 2—Proof of Principle of Method for Clearing a Plasmid Previously Introduced into a Microbial Host Strain Objective This example describes removal of a first plasmid present within a microbial strain with the objective being to obtain a final strain in which said first plasmid is no longer present, thereby effectively curing said microbial strain of said first plasmid.

Materials and Methods

As shown in FIG. 5A-5D, to obtain a final strain in which the first plasmid is no longer present in the microbial strain, a second plasmid that contains the same origin of replication as the first plasmid, an antibiotic selection marker, and an optional counterselectable marker is transformed into the strain (FIG. 5A). Transformants that have taken up the second plasmid are selected for by plating on selective media (FIG. 5B). Growth of the resulting strain under selection to maintain the second plasmid results in the loss of the previously present, first plasmid (FIG. 5C). This second plasmid can then be lost by relief from antibiotic selection and/or active counterselection of the optional counterselectable marker on the plasmid, resulting in a final strain that is free from the first, second, or any additional plasmids (FIG. 5D). It should be noted that the first plasmid can be a plasmid previously introduced into the microbial strain, such as, for example, during a gene editing method as provided herein and/or known in the art, or can be a plasmid native to the microbial strain.

Example 3—Proof of Principle of Method for Iterative Editing in a Multiplexed Fashion Objective This example describes the use of a CRISPR mediated method for extending the iterative editing method described in Example 1 such that more than 1 edit is imparted on a microbial host cell or transformant derived therefrom in each round of a series of successive rounds of gene editing with the goal of stacking multiple genomic edits in the genome of a microbial host cell without requiring the use of counter-selectable markers in each round of gene editing. In this example, the approach is similar to what is described in Example 1 and elsewhere throughout this disclosure, with the exception that each introduced plasmid contains >1 guide RNA(gRNA)/repair fragment pairs.

Materials and Methods

The microbial cell used in this Example is the same *E. coli* W3110 strain generated and used in Example 1.

Three different sets of editing plasmids are prepared for iterative multiplex editing in *E. coli*. The same plasmid backbone is used per set. Editing is performed through three rounds with the goal of introducing two different edits into a host cell's genome per each round of editing, wherein the edits introduced per each round are different than the edits introduced in a previous round of editing. Each editing plasmid contains two different sgRNA/repair fragment pairs. All editing plasmids contain the same replication ori, and each different set of editing plasmids contain a different antibiotic marker (in this example, plasmid set 1=KanR, plasmid; set 2=ChlorR, plasmid; set 3=TetR). Thus, each of the KanR, ChlorR, and TetR plasmids contain different multiple sgRNA/repair fragment pairs.

For the first round of editing, the KanR plasmid (set 1) is transformed into the *E. coli* W3110 base strain containing the ClinR Cas9/lambda red plasmid as described above in Example 1. Transformants are selected for by plating on media selective for kanamycin and carbenicillin. Several Kan and Clin resistant colonies are picked for genotyping and grown overnight in media containing carbenicillin to select only for the Cas9/lambda red plasmid. Competent cells are made from the overnight cultures derived from the round 1 transformants, and the resulting competent round 1 transformants containing Cas9/lambda red plasmid and KanR plasmids are transformed with the ChlorR plasmids (set 2). Round 2 transformants are selected for via growth on chloramphenicol and carbenicillin containing plates. Several ChlorR and Clin resistant colonies are picked for genotyping (genotyping of both ChloR edits as well as KanR edits) and grown overnight in media containing carbenicillin to select only for the Cas9/lambda red plasmid. Competent cells are made from the overnight cultures derived from the round 2 transformants, and the resulting competent round 2 transformants containing Cas9/lambda red plasmid and ChlorR plasmids (a subset may also contain KanR plasmids) are transformed with the TetR plasmids (set 3). Round 3 transformants are selected for via growth on tetracycline and carbenicillin containing plates. Several tetracycline resistant colonies are picked for genotyping (genotyping of TetR, ChloR, and KanR edits) and grown overnight in media containing carbenicillin to select only for the Cas9/lambda red plasmid. A round of counterselection may be optionally applied to actively clear out any remaining plasmids in the population of cells (e.g., "2" in FIGS. 1 and 6). For example, in some cases, rather than growing the cells in media containing only carbenicillin after the last round of editing, the cells are grown overnight in media also containing an appropriate amount of counterselection agent (e.g., 5% sucrose) to generate a strain lacking all of the introduced plasmids containing the sgRNA/repair fragment pairs. The resulting population of cells comprises individual cells having multiple different genetic edits typically, 6 different edits per cell in this example; the different edits corresponding to some or all of the different sgRNA/repair fragment pairs present per a plasmid set, per each round of editing.

Example 4—Proof of Principle of Method for Iterative Editing in a Pooled Fashion Objective This example describes the use of a CRISPR mediated method for extending the iterative editing method described in Examples 1 and 3 in order to create a collection of combinations of edits (i.e., biodiversity). In order to accomplish this, the iterative editing methods described in Examples 1 and 2 may be extended in such a way where each transformation or round of transformations is comprised of the introduction of more than 1 or greater than 1 editing plasmid.

Materials and Methods

The pooled iterative editing method described in this Example can also be performed in the same *E. coli* W3110 strain generated and used in Example 1.

To implement the pooled iterative editing method of this Example, iterative editing as described above in Examples 1 and 3 is performed in such a manner that pools of editing plasmids are used for each set during the editing rounds, such that each editing plasmid per set comprises one sgRNA/repair fragment pair targeting the same locus (basic iterative editing as described in Example 1) or two or more different sgRNA/repair fragment pairs targeting multiple loci (multiplex iterative editing as described in Example 3). An embodiment of this Example is shown in FIG. 6 ("Combinatorial mutation stacking") in comparison with a non-pooled embodiment described herein ("Single mutation stacking"). After each transformation, colonies are collected from the plate and combined—competent cells are then prepared from this collection of colonies. In the second round of editing, a separate pool of edit plasmids is transformed (containing a selection marker different from round 1) and transformants are selected. Transformants from round 2 are collected from the plate and combined, competent cells are then prepared and used for transformation of a $3^{rd}$ pool of edits. After the completion of n rounds of pooled transformation, the individual colonies can be genotyped and tested for a phenotype of interest. After completing transformations, a round of counterselection may be optionally applied to actively clear out any remaining plasmids in the population of cells (e.g., "2" in FIGS. 1 and 6). The resulting population of cells will comprise sub-populations having different single or multiple different genetic edits per cell, the different edits corresponding to some of the different sgRNA/repair fragment pairs present per plasmid set, per any round of editing.

Example 5—Proof of Principle of Method for Homologous Recombination (HR)-Mediated Pooled Strain Build in *E. coli*

Objective

This example details the use of native homologous recombination to create a collection of edited microorganisms. In this example, each plasmid contains sequence homology to a region in the genome (e.g. left and right homology arms). The left and right homology arms are separated by a designed edit (e.g. promoter or other sequence insertion, substitution, or deletion). Other features of the plasmid include a positive selectable marker (e.g. Kanamycin resistance cassette), a counter selectable marker or markers (e.g. SacB or PheS, that confer toxicity in the presence of sucrose and 4-chloro-phenylalanine, respectively), and an R6K origin of replication.

Materials and Methods

Construction of strains using the pooled strain build generally consists of two parts. First, generation of an edited strain library by making pools of plasmids capable of making one of many possible edits and transforming them into the recipient microorganism at a single time. Second, identification of which locus or loci, if any, are edited.

Generation of the Edited Strain Library

Six (6) different pools of 10 plasmids/pool were prepared such that each plasmid was present in equimolar quantities. Each plasmid contained a promoter sequence to add that was flanked by 1-kb homology arms. These pools of plasmids were electroporated into an *E. coli* strain, recovered in rich growth medium for 1-3 hr at 37 C, and single colonies containing a single recombination event were selected using standard *E. coli* culturing methods. It should be noted that the time for recovery after transformation (i.e., 1-3 hr at 37 C) was used to ensure recovery of transformants from the electroporation while minimizing the probability of generating bias in the pooled library (e.g. some edited strains may be more or less frequent and/or grow faster or slower than other edited or non-edited strains). Further, the resulting transformants were plated on a medium to select for transformants where the recombination of the plasmid with the chromosome occurred at one of the 2 homology sites present in the plasmid and that flank the designed edit.

Colonies containing the single recombination event were pooled together by scraping the agar medium and resuspending the combined colony biomass in liquid medium. Approximately 100 colonies were pooled together during scraping to maintain diversity in the colonies resulting from each pool of 10 plasmids. These colonies were resuspended in Lysogeny broth medium containing 25% glycerol and 50 ug/mL kanamycin, frozen at −80 C for 60 min, thawed at room temperature, and incubated at 37 C with agitation for 30 min. The cells suspensions were then diluted and multiple dilutions were plated on medium containing sucrose and 4-chlorophenylalanine (counter-selectable medium) to induce and select for the occurrence of the second recombination event, mediated by the counterselection genes sacB and pheS. The plates were incubated at 30 C for 24-36 hrs. This allowed for the induction and selection of cells (and then colonies) whose chromosome went through a second recombination event at either the left or right homology arm. If the second recombination event occurred at the same homology arm as the first recombination event, the starting strain is recreated. If the second recombination event was at the second recombination site, the resulting strain contained the intended edit. Thus, the population of colonies growing on the counter selection medium comprises both unedited strains and a mixture of edited strains, each containing one of the edits included in the initial plasmid pool.

Identification of the Edited Locus

Colonies resulting from the second recombination event, containing either the designed edit in the genome or the original parent genotype, were picked and grown in liquid medium overnight at 37 C. The edited locus was identified by PCR and/or next-generation sequencing (NGS) techniques as known in the art.

Figure 12:
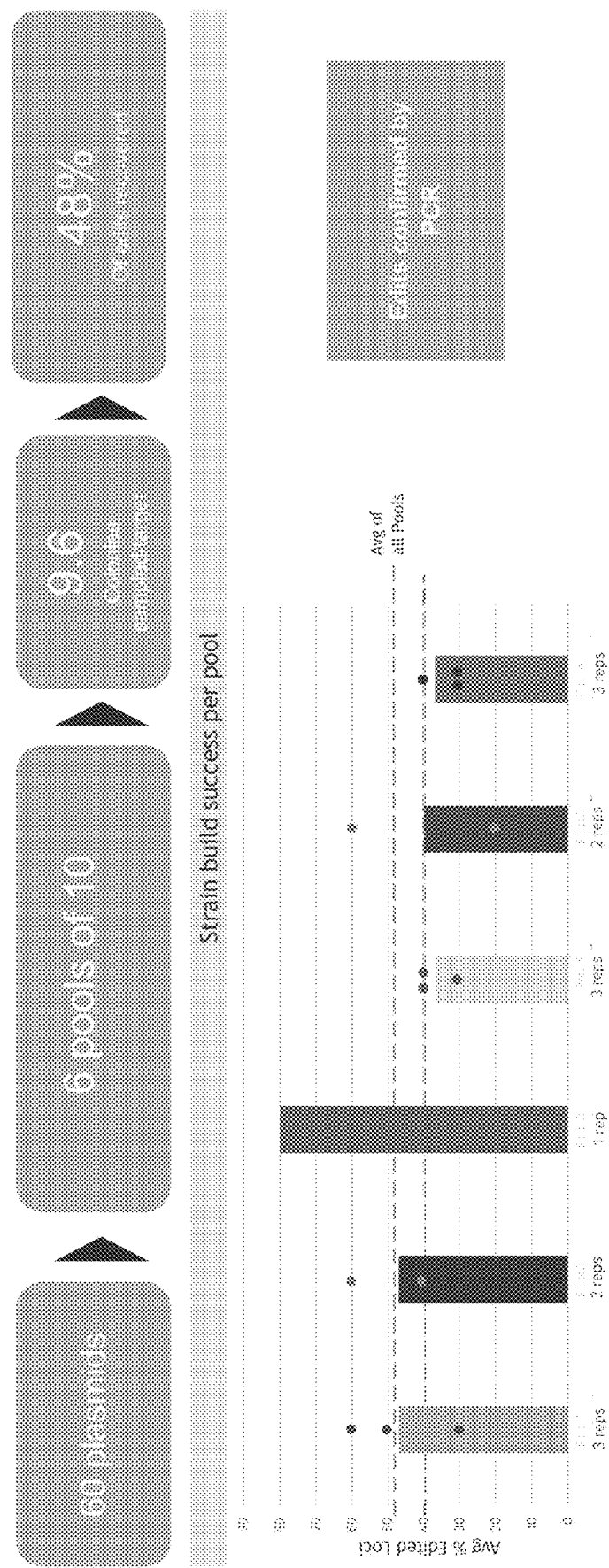
FIG. 12 depicts the results of PCR screening and next generation sequencing (NGS) of *E. coli* subjected to a homologous recombination (HR)-mediated pooled strain build as described in Example 5.

Of the original 10 plasmids introduced into the cells, an average of 40%-50% unique edits built via the 10 plasmids could be recovered per pooled plasmid transformation, after screening 96 of the colonies that grew on the sucrose and 4-chlorophenylalanine medium (see FIG. 12).

Example 6—Use of Pooled Genome Editing in S. cerevisiae Using CRISPR/Cas9 Mediated Homology-Directed Repair Objective This example details the use of native homologous recombination to create a collection of edited S. cerevisiae strains. In this example, each payload to be inserted into S. cerevisiae host cells contains sequence homologous to a region in the genome (e.g. left and right homology arms). The left and right homology arms are separated by a designed edit (e.g. deletion).

Materials and Methods

Construction of strains using the pooled S. cerevisiae strain build generally consisted of two parts. First, generation of an edited strain library by making a pool of plasmids capable of making one of three (3) possible edits at a genomic locus and transforming them into the recipient S. cerevisiae host cell at a single time. Second, identification of which edits occurred at the specific locus. Overall, the process entailed transforming a host S. cerevisiae strain using Cas9 mediated homologous recombination in a process in which one of three (3) distinct payloads were inserted into each locus targeted (see FIG. 7A).

Cas9 was expressed from an antibiotic-selectable CEN.ARS plasmid encoding an antibiotic (i.e., Nourseothricin) resistance marker gene present in a host S. cerevisiae strain. An sgRNA expression construct containing a spacer targeting one of six (6) genomic loci (i.e., ARI1 gene, TRP1 gene, ADH6 gene, ECM13 gene, MCH5 gene or PRB1 gene) was provided in each of six (6) separate transformations (i.e., one transformation per locus) as a linear DNA molecule with homology arms for integration via homologous recombination into the Cas9 expression plasmid present in the host cell. Three (3) edit payloads were generated as linear fragments of DNA for each locus using PCR to add 45 bp homology arms targeting the payload to the desired locus and deleting the sequence targeted by the corresponding sgRNA and replacing with a specific edit payload. The three (3) edit payloads were: (1) red fluorescent protein (RFP) operably linked to a constitutive promoter in a 5' to 3' orientation (designated as RFP_F), (2) RFP operably linked to a constitutive promoter in a 3' to 5' orientation (designated as RFP_R), or (3) RFP operably linked to a constitutive promoter in a 5' to 3' orientation and green fluorescent protein (GFP) operably linked to a different constitutive promoter in a 5' to 3' orientation (designated as RFP_GFP). For each of the six (6) targeted genomic loci, the linearized Cas9 expression plasmid, linear sgRNA expression cassette and an equimolar pool of the three (3) payload amplicons were transformed into S. cerevisiae via chemical transformation process and transformants were selected on media containing Nourseothricin. The chemical transformation process entailed using the lithium acetate/single-stranded carrier DNA/polyethylene glycol method as described in Gietz, et al., Transformation of yeast by lithium acetate/single-stranded carrier DNA/polyethylene glycol method. Methods in Enzymology, 350(2001), 87-96.

Following each transformation colonies were cultured and genotyped using PCR and/or next-generation sequencing (NGS) techniques as known in the art.

Results and Conclusions

Figure 7A:
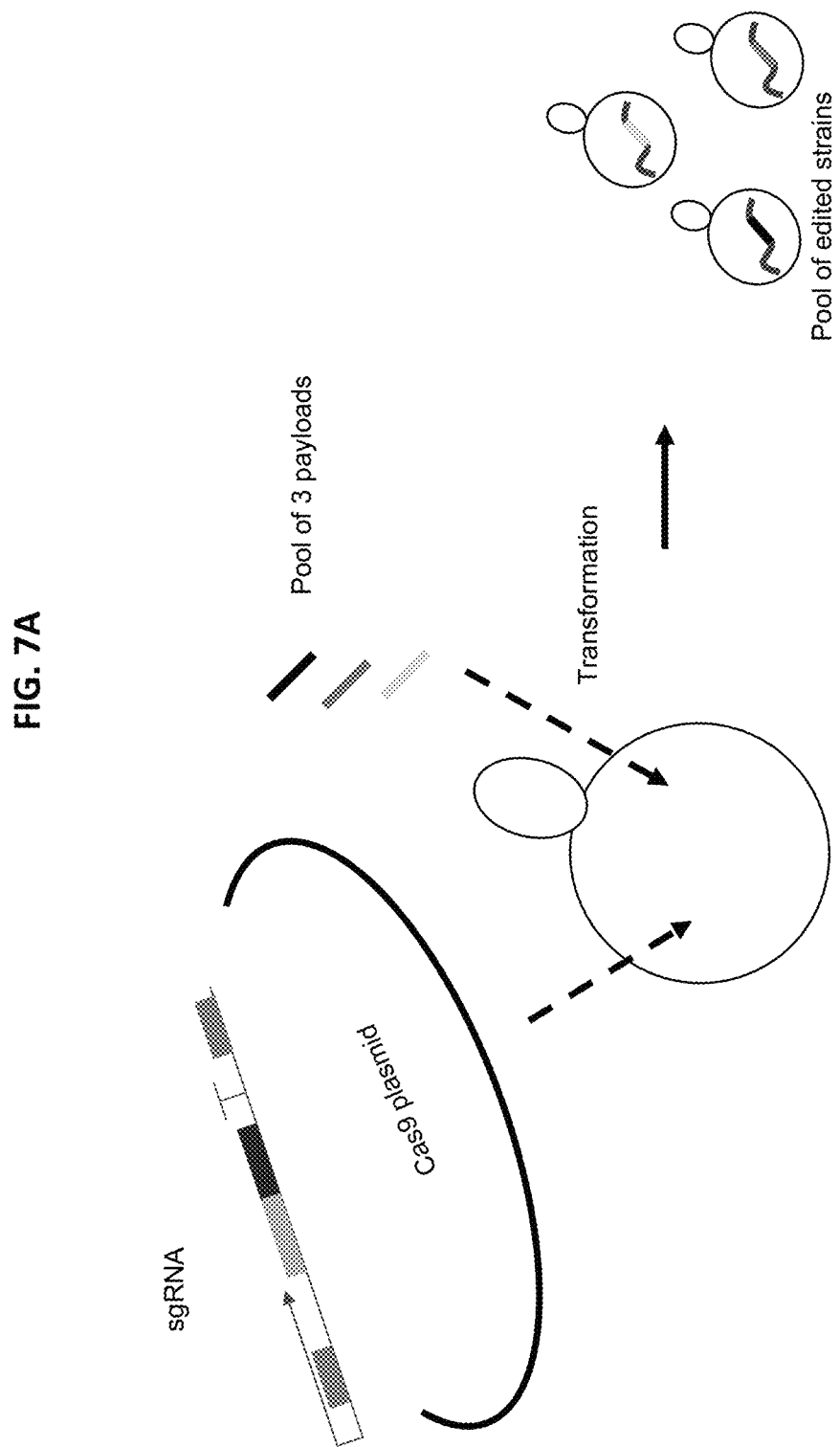
FIG. 7A-7B illustrates pooled genome editing in *S. cerevisiae* using CRISPR/Cas9 homology-directed repair.
Figure 7B:
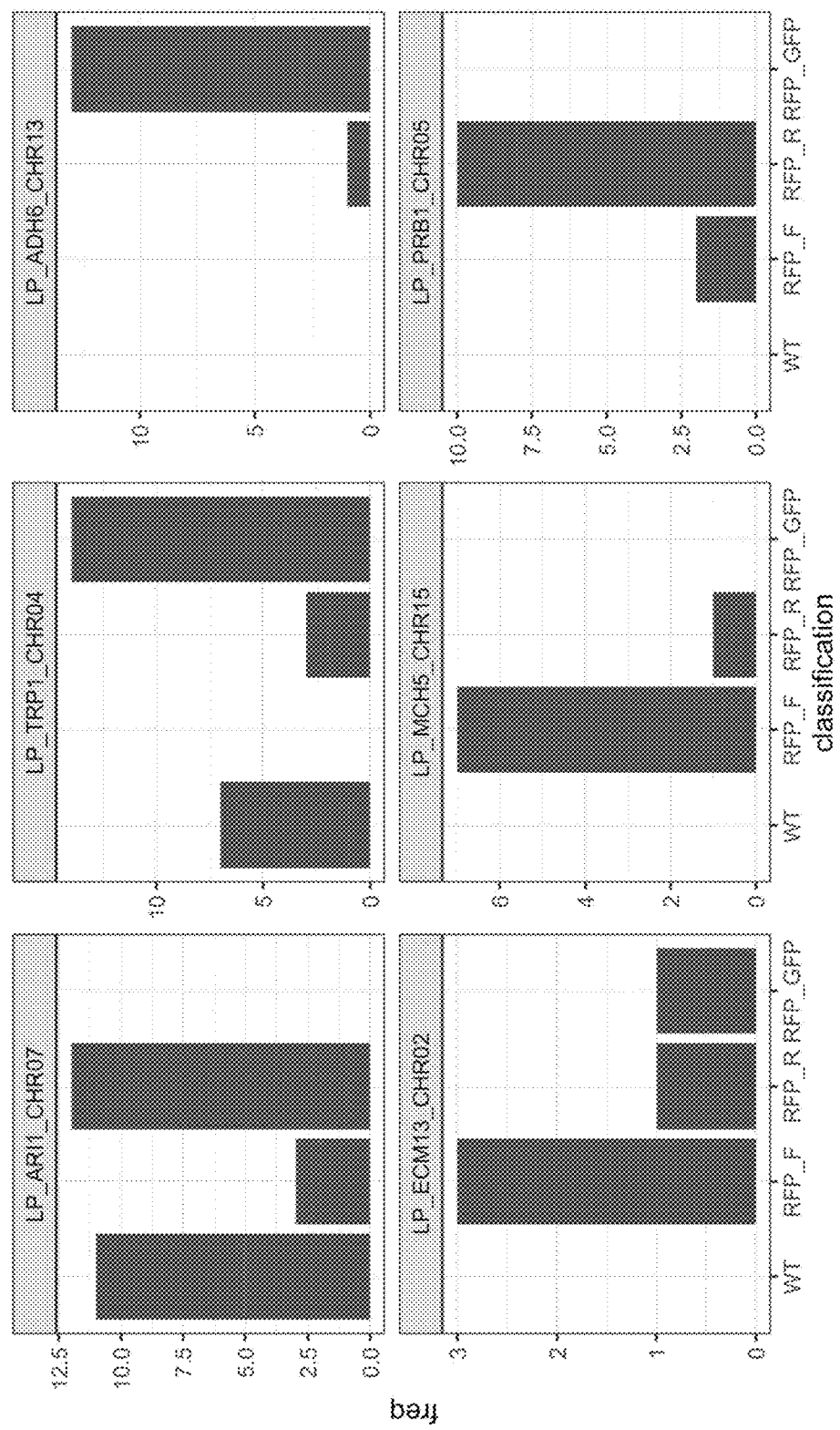

As shown in FIG. 7B, among the colonies tested following each transformation, all three payloads were detected. This process demonstrated that pools of payloads may be used in CRISPR/Cas9 mediated genome editing in S. cerevisiae to efficiently and inexpensively generate new S. cerevisiae strains.

Example 7—Use of Iterative Genome Editing in S. cerevisiae Using CRISPR/Cas9 Mediated Homology-Directed Repair Objective This example details the use of native homologous recombination to iteratively edit the genome of a S. cerevisiae host cell to create a collection of edited S. cerevisiae strains. In this example, each edit payload to be inserted into S. cerevisiae host cells in each successive round of transformation introducing a new edit payload contains sequence homology to a region in the genome (e.g. left and right homology arms). The left and right homology arms are separated by a designed edit (e.g. deletion).

Materials and Methods

Figure 8A:
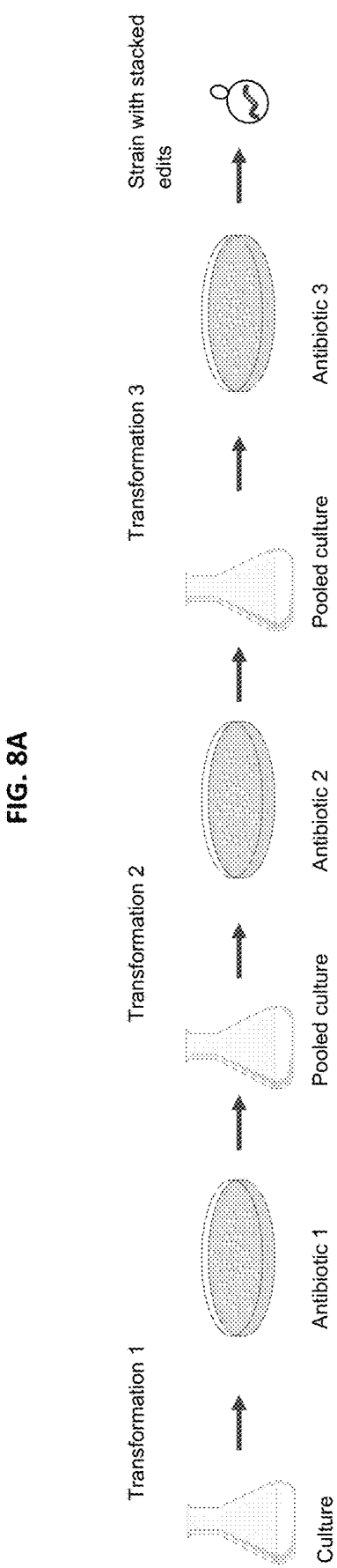
FIG. 8A-8C illustrates iterative genome editing in *S. cerevisiae* using CRISPR/Cas9 homology-directed repair.

Construction of strains using the pooled S. cerevisiae strain build generally consisted of two parts. First, generation of an edited strain library by making a pool of plasmids capable of making one of three (3) possible edits at a genomic locus and transforming them into the recipient S. cerevisiae host cell at a single time and then repeating this process for two additional rounds of editing, with each additional round targeting a different locus with one of three (3) possible genetic edits for the genomic locus targeted in the specific additional round. Second, identification of which edits occurred at the specific loci. Overall, the process entailed transforming a host S. cerevisiae strain using Cas9 mediated homologous recombination in a process in which one of three (3) distinct payloads were inserted into each locus targeted as shown in FIG. 7A, but repeating the process for two additional rounds as shown in FIG. 8A.

For each round of three (3) rounds of transformation, Cas9 was expressed from one of three (3) antibiotic-selectable CEN.ARS plasmids present in a host S. cerevisiae strain. Each round of transformation used a CEN.ARS plasmid encoding one of three different antibiotic selectable marker genes such that each round used a CEN.ARS plasmid with a different antibiotic selectable marker (i.e., Nourseothricin (antibiotic 1), geneticin (G418) (antibiotic 2) or hygromycin (antibiotic 3) in FIG. 8A) from each other round of transformation. In each round of transformation, an sgRNA expression construct containing a spacer targeting a genomic loci that was different from a genomic locus targeted in each other round of transformation provided as a linear DNA molecule with homology arms for integration via homologous recombination into the Cas9 expression plasmid present in the host cell. One (1) edit payload of three (3) possible edits was generated as a linear fragment for the locus targeted in a specific round of transformation using PCR to add 45 bp homology arms targeting the payload to the desired locus for the specific round of transformation and deleting the sequence targeted by the corresponding sgRNA and replacing with the specific edit payload. Each round of transformation introduced a separate one (1) of the three (3) possible payloads. The three (3) possible edit payloads were: (1) red fluorescent protein (RFP) operably linked to a constitutive promoter in a 5' to 3' orientation (designated as RFP_F), (2) RFP operably linked to a constitutive promoter in a 3' to 5' orientation (designated as RFP_R), or (3) RFP operably linked to a constitutive promoter in a 5' to 3' orientation and green fluorescent protein (GFP) operably linked to a different constitutive promoter in a 5' to 3' orientation (designated as RFP_GFP).

Figure 8C:
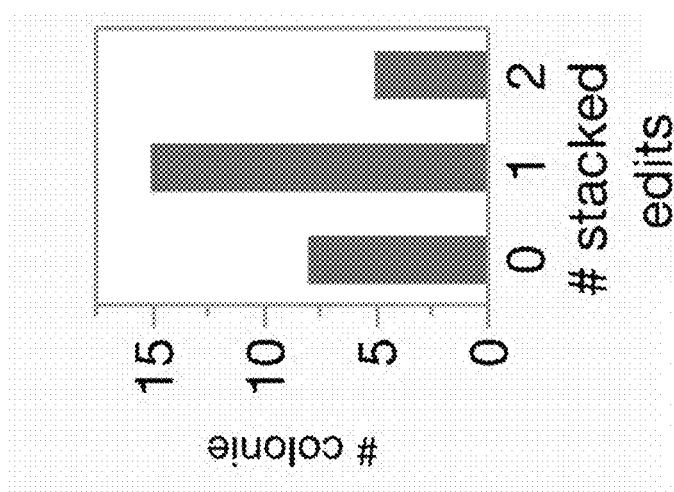
Figure 8B:
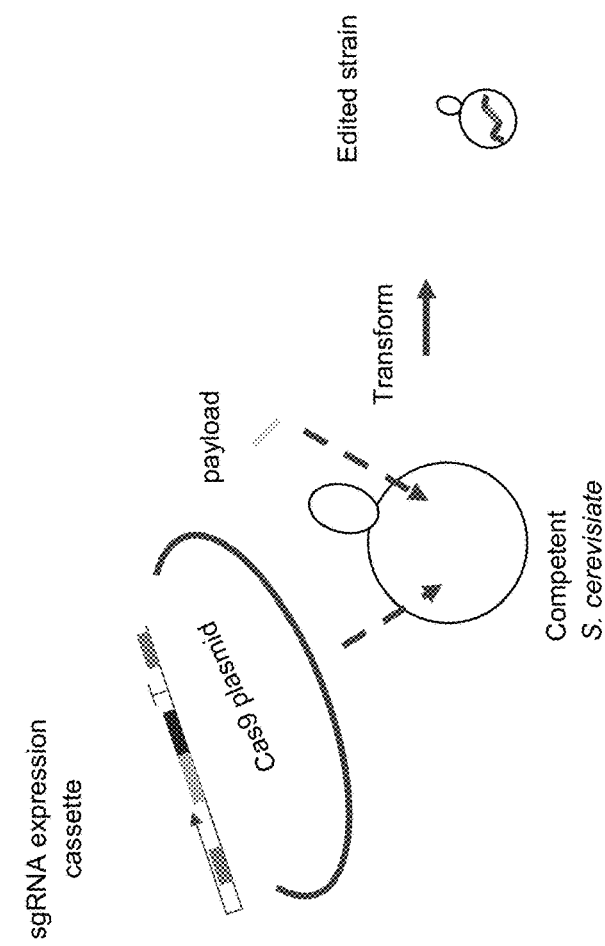

As shown in FIG. 8B, for each round of transformation, the linearized Cas9 expression plasmid, linear sgRNA expression cassette and specific edit payload were transformed into S. cerevisiae via the chemical transformation process utilized in Example 6 and transformants were selected on media containing the relevant antibiotic for the specific round of transformation (i.e., antibiotic 1, 2 or 3). The first transformation was performed using Nourseothricin sulfate (antibiotic 1) selection, the second using geneticin G418 (antibiotic 2) selection, and the third using hygromycin (antibiotic 3) selection. Following the initial round of transformation and selection with the first antibiotic (antibiotic 1), the colonies were cultured in liquid for 2 hours, made competent, then transformed with a second round of editing using a second set of sgRNA cassette/edit payloads. Transformants from the second round of editing were selected on solid media using the second antibiotic (antibiotic 2), then cultured in liquid, made competent and transformed a third time with a third set of sgRNA/edit payloads and selected using the third antibiotic (antibiotic 3). Following the third round of editing, colonies were cultured and genotyped using PCR and/or next-generation sequencing (NGS) techniques as known in the art.

Results and Conclusions

As shown in FIG. 8C, genotyping of two genomic edits introduced by rapidly iterated transformations following a traditional transformation showed that 17.8% of 28 colonies genotyped contained both iterated edits. This process demonstrated that payloads introduced in an iterative process may be used in CRISPR/Cas9 mediated genome editing in S. cerevisiae to efficiently and inexpensively generate new S. cerevisiae strains.

Example 8—Proof of Principle of Pooled Plasmid Iterative Stacking (PPIS)

Objective

This example details the use of pooled plasmid iterative stacking (PPIS) for generating many genotypes from a single pooled transformation per round of editing. Rather than transforming plasmids individually, in this Example a pool of 4 plasmids were transformed into a host cell, the plasmids were cleared and then pooled and used to inoculate a main culture. The main culture was then subjected to a repeat of the process using a pool of 4 plasmids (see FIG. 9A).

Materials and Methods

Figure 9A:
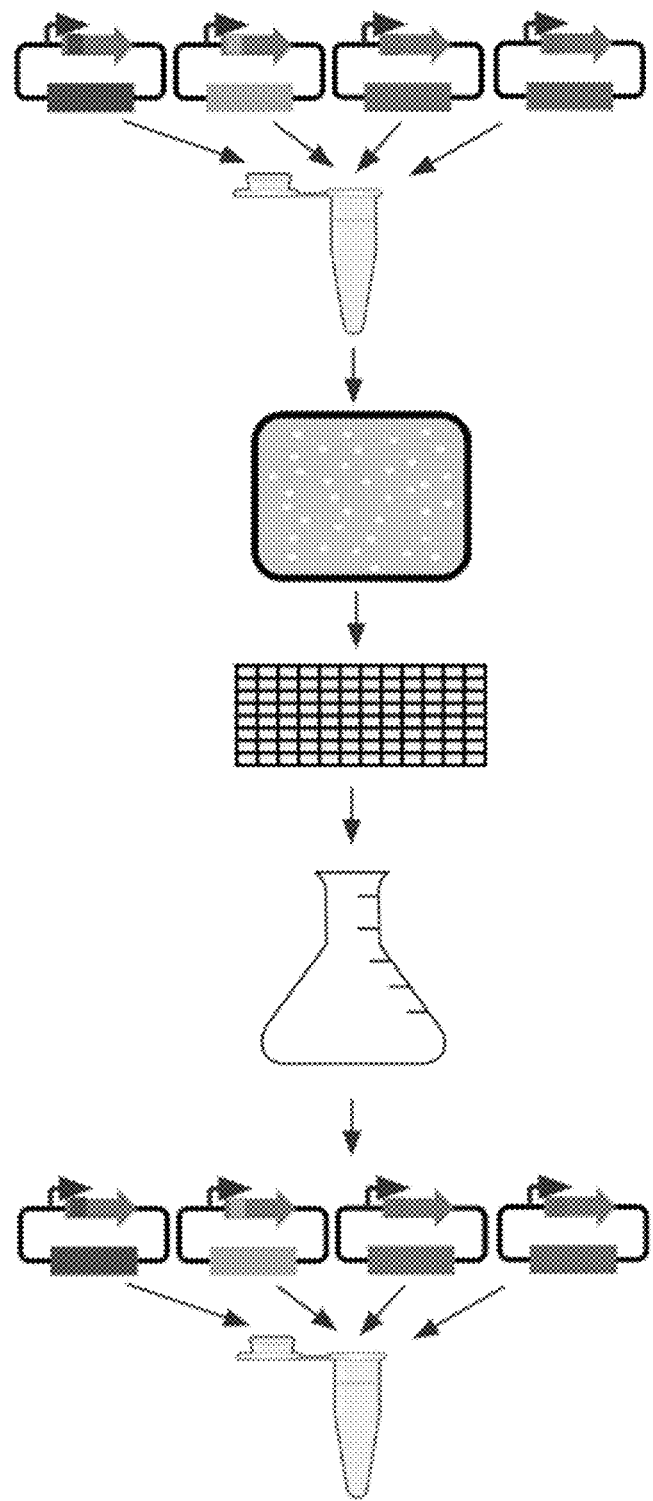

Overall, for pooled plasmid iterative stacking (PPIS), multiple plasmids containing edit payloads (pEDIT plasmids) were mixed and used to transform a culture comprising E. coli host cells in multiple rounds of editing (see FIG. 9A). Prior to transformation of the E. coli host cells, a pCUT2.2 plasmid was introduced into said host cells. The pCUT2.2 plasmid is a replicating plasmid containing Cas9, recombineering machinery, carbenicillin resistance cassette, and temperature sensitive origin of replication. Following introduction of the pCUT 2.2 plasmid into the E. coli host cells, a pool of 4 plasmids each containing edit payloads were mixed and introduced into the E. coli host cells containing the pCUT2.2 plasmids in each of four (4) separate, successive rounds of transformation. The pool of 4 plasmids introduced in each successive round of transformation contained pEDIT plasmids with each pEDIT plasmid comprising an edit payload with homology arms and a corresponding sgRNA targeting a specific locus in the E. coli host cell. Following each round of transformation, the pEDIT plasmids introduced in the specific round of transformation were cleared from the transformants for that round (i.e., using active counterselection or alternatively passive counterselection (i.e., growth on non-selective media), the cleared transformants were then pooled and subsequently used as inoculum for a main culture that was then subjected to the next successive round of editing. After the final round of editing, pCUT2.2 was cleared using its temperature sensitive ori.

More specifically, the PPIS process was conducted using the following methods:

(1) Cultures for Competent Cell Preparation.

Seed: Inoculated base editing strain in 5 mL of LBClin100. Shook at 30° C., 160 rpm overnight.

Main: Measured OD600 of seed culture and inoculated 100 mL LBClin100 at a starting OD600 of ~0.04 (depends on base editing strain doubling time). Shook at 18° C., 160 rpm for ~16 h. (The goal was for the cultures to be at an OD600 of ~0.3 the next morning before inducing the recombineering machinery).

The next morning, when the OD600 was at ~0.3, main cultures were induced with 0.2% arabinose (expression of the recombineering machinery was driven by pBAD). Shook cultures at 30° C., 160 rpm until OD600 reached 0.4-0.6 (1-2 hrs).

(2) Competent Cell Preparation.

Chilled cultures on ice for 15 min. Kept cells on ice (or at 4° C.) throughout the entire comp cell prep.

Centrifuged at 4° C., 4000×g for 10 min. Resuspended cells in 50 mL cold 10% glycerol, transferred to a 50 mL conical, and spun at 4° C., 3500×g for 10 min. Decanted and washed 2 more times for a total of 3 washes. After the final wash, decanted liquid and resuspended the cell pellet in the small volume of 10% glycerol remaining at the bottom of the 50 mL conical.

Diluted comp cells 1:50 (980 uL 10% glycerol+20 uL cells) and measured OD600. Adjusted the OD600 of the comp cells with cold 10% glycerol to a final OD600 of ~50-75.

(3) Transformation

Mixed 50 uL of comp cells and 100 ng plasmid (for pooled plasmid—added a total of 100 ng, i.e. 100 ng/#of plasmids=ng per plasmid), transferred to a 1 mM cuvette, and electroporated using the *E. coli* setting. In this Example, 4 unique genetic edits were used such that one of the four genetic edits were present on a separate plasmid and, thus 4 plasmids were mixed and transformed in each round of editing.

Immediately resuspended in NEB recovery media (750 uL).

Recovered by shaking for 3 hrs at 30° C., 1000 rpm.

Plated 900 uL (1:500 dilution) on undivided LBClin100Kan50 Qtray. Dried in WhisperFlow cabinet for 1 hr. Incubated Qtray at 30° C. for 1-2 days (until colonies were pickable).

(4) pEDIT Clearance

Picked n colonies (n=4× possible genotypes) into 300 uL LBClin100Kan50 96MWP or 120 uL LBClin100Kan50 384DWP. Shook at 30° C., 160 rpm overnight.

When the LBClin100Kan50 cultures were saturated, banked (mixed equal volumes of culture and 50% glycerol) and stamped 3 uL into 300 uL LBClin100+10% sucrose 96MWP or 2 uL into 120 uL LBClin100 384DWP to clear pEDIT (active counterselection with sacB). Shook at 30° C., 160 rpm overnight.

When the LBClin100Suc10 cultures were saturated, pooled cultures with the same pool of edits and diluted to 10-5.

Plated 900 uL of diluted cultures onto an undivided LBClin100 Qtray. Dried in WhisperFlow cabinet for 1 hr. Incubated Qtray at 30° C. for 1-2 days (until colonies were pickable).

Picked 1 colony per Qtray well into 30 uL of sterile water. Resuspended colonies and stamped 3 uL into 300 uL LBClin100 and 300 uL LBClin100Kan50 96MWP or 2 uL into 120 uL LBClin100 and 120 uL LBClin100Kan50 384DWP. Shook at 300 C, 160 rpm overnight.

When LBClin100 cultures were saturated, measured OD600 of both LBClin100 and LBClin100Kan50 plates to check for cultures that did not clear pEDIT. Cultures that grew in LBClin100Kan50 did not clear pEDIT and were not carried forward for subsequent rounds of editing.

Banked cultures (mixed equal volumes of culture and 50% glycerol) that cleared pEDIT, i.e. grew in LBClin100, but not in LBClin100Kan50.

Pooled cultures that cleared pEDIT (seed). Measured OD600 of pooled seed culture and inoculated 100 mL LBClin100 at a starting OD600 of ~0.04 (depends on base editing strain doubling time).

(5) Strain QC

Performed n rounds of editing by repeating steps 1-4. In this example, 4 rounds of editing were performed.

After the final round of editing (i.e., round 4), made boil preps of pEDIT cleared cultures (did not pool wells) by stamping 5 uL culture into 20 uL TE and incubating at 98° C. for 10 min.

Stamped 7 uL sterile water into a 384-well PCR Framestar plate and added amplicon NGS primers (containing i5/i7 adapters).

Stamped 3 uL of boil prep and 10 uL of NEB OneTaq Hot Start Master Mix with GC Buffer into 384-well PCR Framestar plate containing primers. Total reaction volume was 20 uL.

Ran PCR with standard NEB OneTaq Hot Start Master Mix with GC Buffer conditions.

Handed off mapped amplicon plate to Genomics and Sequencing Core for amplicon NGS.

Performed kmer search on samples to assess whether editing occurred.

(6) pCUT2.2 Clearance

Stamped 3 uL of LBClin cultures (post pEDIT clearance) into 1 mL LB 96DWP. Shake at 42° C., 1000 rpm for 17-20 hrs.

Measured OD600, made 10-4 through 10-7 dilutions in LB, and plated 150 uL onto LB and LBClin divided Qtrays.

Incubated LB and LBClin Qtrays @ 30 C for 20-22 hrs.

Screened for pCUT2.2 clearance (solid media): Qtray wells with growth on LB but not LBClin indicated pCUT2.2 clearance.

Picked n colonies from Qtray wells with growth on LB but not LBClin into 300 uL water. Resuspended colonies and stamped 5 uL into 300 uL LB and LBClin 96MWP.

Confirmed pCUT2.2 clearance (liquid media): Wells with growth in LB, but not LBClin, indicated successful clearance of pCUT2.2.

Banked cultures (mixed 75 uL of culture into 75 uL of 50% glycerol) that cleared pCUT2.2.

Results and Conclusions

Figure 9B:
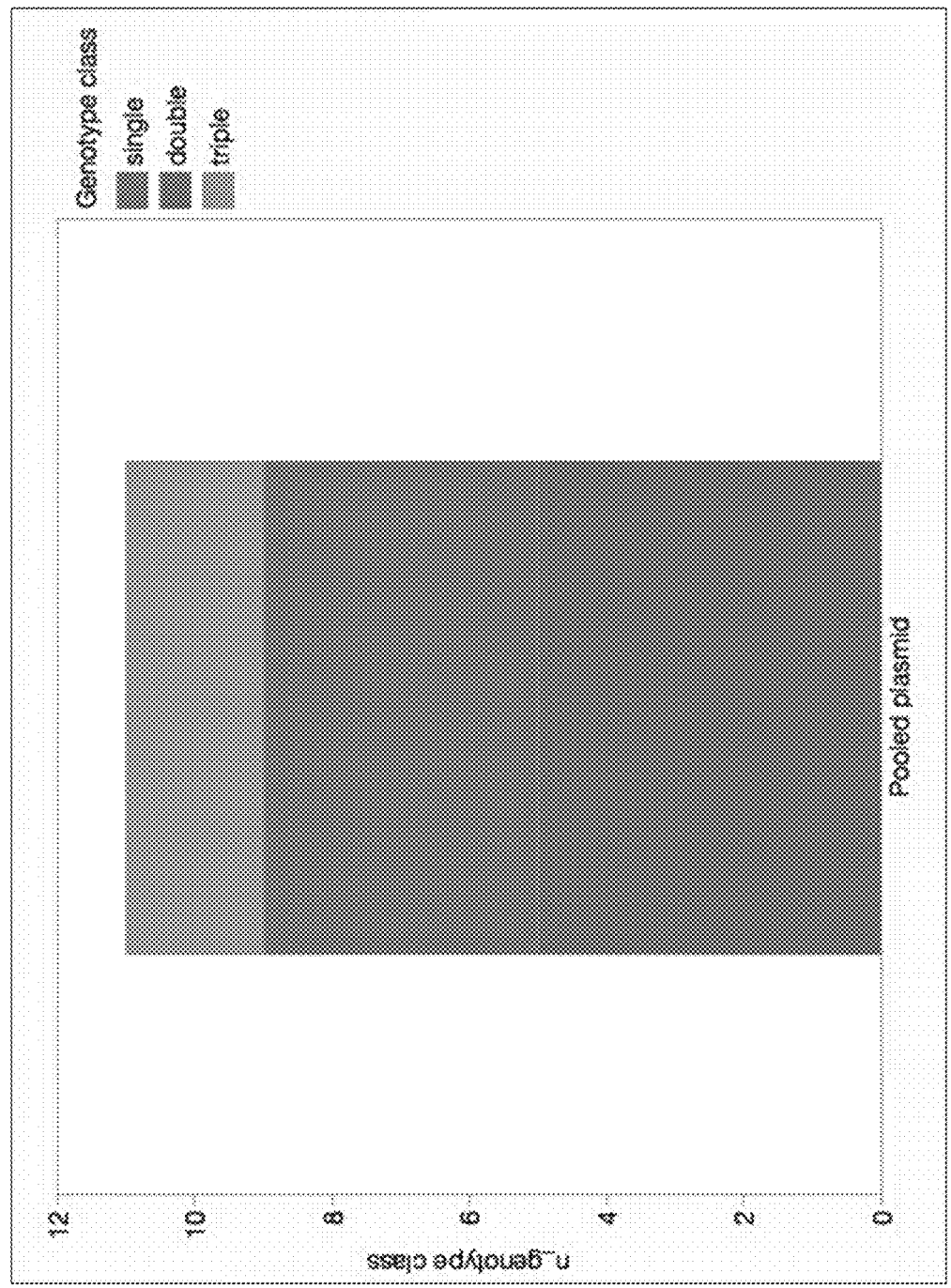
FIGS. 9B-9C show that 11 out of 125 or ~9% of possible genotypes in *E. coli* were captured following the application of 4 unique edits/round for 4 rounds using CRISPR mediated homology directed repair in a PPIS method (no editing occurred in 1 of the 4 rounds and was excluded from the #of possible genotypes).
Figure 9C:
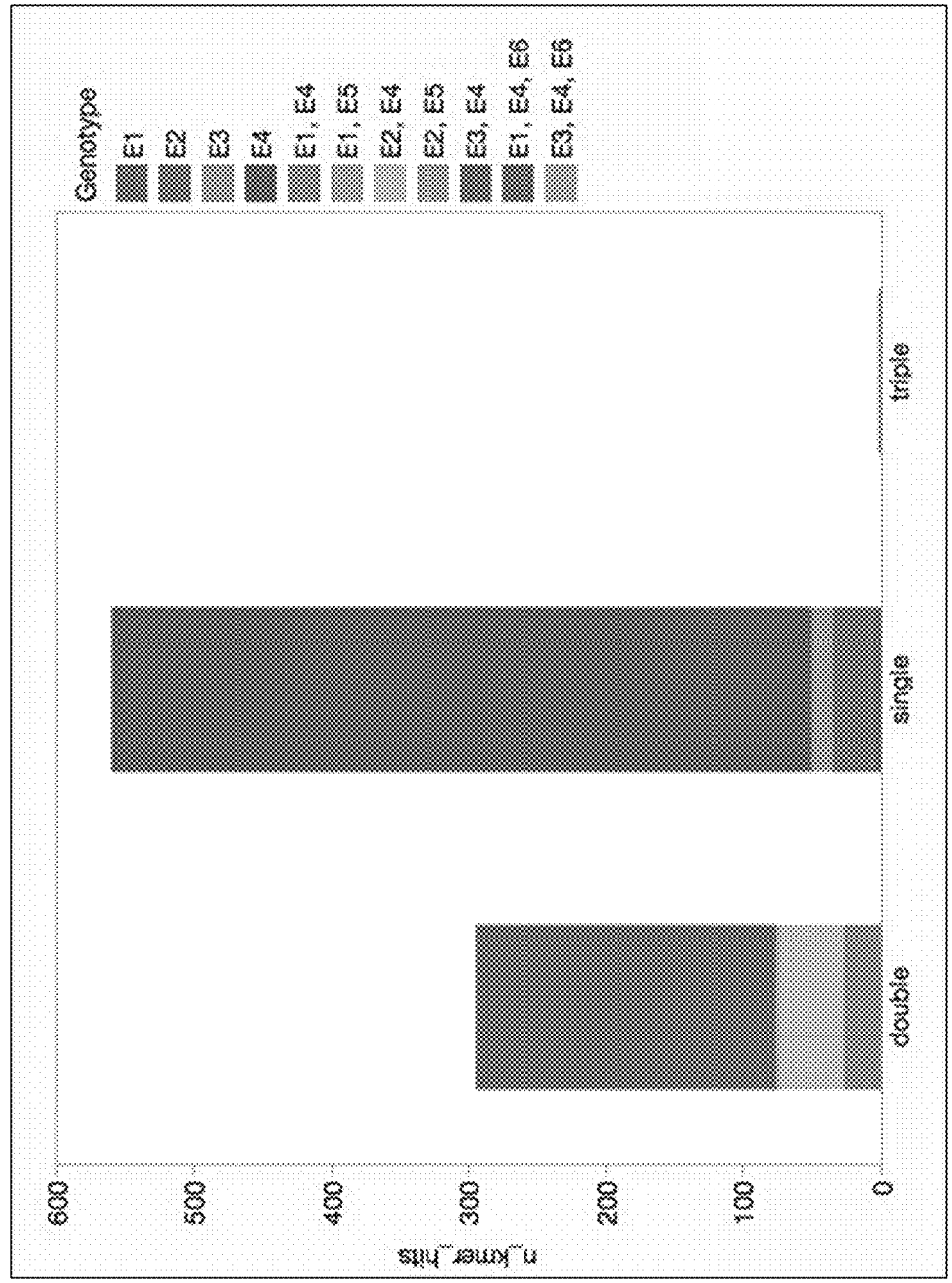

In theory, four (4) unique edits/round for four (4) rounds of PPIS using CRISPR can produce 625 possible genotypes in *E. coli*. As shown in FIG. 9B-9C, 11 out of 125 or ~9% of possible genotypes in *E. coli* were captured (no editing occurred in 1 of the 4 rounds and was excluded from the #of possible genotypes), indicating that PPIS using CRISPR can be an effective method for introducing multiple genetic edits across multiple genomic loci.

Example 9—Proof of Principle of Pooled Parent Iterative Stacking (PPAIS

Objective

This example details the use of pooled parent iterative stacking (PPAIS) for generating many genotypes and minimizing transformation/edit bias by transforming plasmids individually into separate *E. coli* host cell cultures.

Materials and Methods

Overall, for pooled parent iterative stacking (PPAIS), rather than transforming a pool of plasmids like pooled plasmid iterative stacking (PPIS) into a culture of host cells, four (4) pools of pEDIT plasmids were transformed individually into separate cultures of host cells, the pEDIT plasmids were cleared from each separate culture, all the cleared strains were pooled (seed) and used to inoculate a main culture that was then divided into separate cultures. In the next round of editing, the process was repeated by transforming four (4) pools of plasmids individually into the separate cultures produced by dividing the main culture from the previous round of editing (see FIG. 10A). Similarly to the *E. coli* host cells used in Example 8, the *E. coli* host cells comprised a pCUT2.2 plasmid that was introduced into said host cells prior to initiating rounds of editing. Like the pEDIT plasmids in Example 8, each pEDIT plasmid comprised an edit payload with homology arms and a corresponding sgRNA targeting a specific locus in the *E. coli* host cell. Also similar to Example 8, following each round of transformation, the pEDIT plasmids introduced in the specific round of transformation were cleared from the transformants for that round (i.e., using active counterselection or alternatively passive counterselection (i.e., growth on non-selective media) and after the final round of editing, pCUT2.2 was cleared using its temperature sensitive ori.

More specifically, the PPAIS process was conducted in the following manner:

(1) Cultures for Competent Cell Preparation:

Seed: Inoculated base editing strain in 5 mL of LBClin100. Shook at 30° C., 160 rpm overnight.

Main: Measured OD600 of seed culture and inoculated 100 mL LBClin100 at a starting OD600 of ~0.04 (depends on base editing strain doubling time). Shook at 18° C., 160 rpm for ~16 h. (The goal was for the cultures to be at an OD600 of ~0.3 the next morning before inducing the recombineering machinery).

The next morning, when the OD600 was at ~0.3, main cultures were induced with 0.2% arabinose (expression of the recombineering machinery was driven by pBAD). Shook cultures at 30° C., 160 rpm until OD600 reached 0.4-0.6 (1-2 hrs).

(2) Competent Cell Preparation:

Chilled cultures on ice for 15 min. Kept cells on ice (or at 4° C.) throughout the entire comp cell prep.

Centrifuged at 4° C., 4000×g for 10 min. Resuspended cells in 50 mL cold 10% glycerol, transferred to a 50 mL conical, and spun at 4° C., 3500×g for 10 min. Decanted and washed 2 more times for a total of 3 washes. After the final wash, decanted liquid and resuspended the cell pellet in the small volume of 10% glycerol remaining at the bottom of the 50 mL conical.

Diluted comp cells 1:50 (980 uL 10% glycerol+20 uL cells) and measured OD600. Adjusted the OD600 of the comp cells with cold 10% glycerol to a final OD600 of ~50-75.

(3) Transformation

Mixed 50 uL of comp cells and 100 ng plasmid, transferred to a 1 mM cuvette, and electroporated using the *E. coli* setting. In this Example, 4 unique genetic edits were used such that one of the four genetic edits were present on a separate plasmid and, each of the four (4) plasmids were transformed individually into *E. coli* host cells.

Immediately resuspended in NEB recovery media (750 uL).

Recovered by shaking for 3 hrs at 30° C., 1000 rpm.

Plated 900 uL (1:500 dilution) on undivided LBClin100Kan50 Qtray. Dried in WhisperFlow cabinet for 1 hr. Incubated Qtray at 30° C. for 1-2 days (until colonies were pickable).

(4) pEDIT Clearance

Picked n colonies (n=4× possible genotypes) into 300 uL LBClin100Kan50 96MWP or 120 uL LBClin100Kan50 384DWP. Shook at 30° C., 160 rpm overnight.

When the LBClin100Kan50 cultures were saturated, banked (mixed equal volumes of culture and 50% glycerol) and stamped 3 uL into 300 uL LBClin100+10% sucrose 96MWP or 2 uL into 120 uL LBClin100 384DWP to clear pEDIT (active counterselection with sacB). Shook at 30° C., 160 rpm overnight.

When the LBClin100Suc10 cultures were saturated, pooled cultures with the same edit and diluted to 10-5.

Plated 900 uL of diluted cultures onto an undivided LBClin100 Qtray. Dried in WhisperFlow cabinet for 1 hr. Incubated Qtray at 30° C. for 1-2 days (until colonies were pickable).

Picked 1 colony per Qtray well into 30 uL of sterile water. Resuspended colonies and stamped 3 uL into 300 uL LBClin100 and 300 uL LBClin100Kan50 96MWP or 2 uL into 120 uL LBClin100 and 120 uL LBClin100Kan50 384DWP. Shook at 30° C., 160 rpm overnight.

When LBClin100 cultures were saturated, measured OD600 of both LBClin100 and LBClin100Kan50 plates to check for cultures that did not clear pEDIT. Cultures that grew in LBClin100Kan50 did not clear pEDIT and were not carried forward for subsequent rounds of editing.

Banked cultures (mixed equal volumes of culture and 50% glycerol) that cleared pEDIT, i.e. grew in LBClin100, but not in LBClin100Kan50.

Pooled cultures that cleared pEDIT (seed). Measured OD600 of pooled seed culture and inoculated 100 mL LBClin100 at a starting OD600 of ~0.04 (depends on base editing strain doubling time).

(5) Strain QC

Performed n rounds of editing by repeating steps 1-4. In this example, 4 rounds of editing were performed.

After the final round of editing (i.e., round 4), made boil preps of pEDIT cleared cultures (did not pool wells) by stamping 5 uL culture into 20 uL TE and incubating at 98° C. for 10 min.

Stamped 7 uL sterile water into a 384-well PCR Framestar plate and added amplicon NGS primers (containing i5/i7 adapters).

Stamped 3 uL of boil prep and 10 uL of NEB OneTaq Hot Start Master Mix with GC Buffer into 384-well PCR Framestar plate containing primers. Total reaction volume was 20 uL.

Ran PCR with standard NEB OneTaq Hot Start Master Mix with GC Buffer conditions.

Handed off mapped amplicon plate to Genomics and Sequencing Core for amplicon NGS.

Performed kmer search on samples to assess whether editing occurred.

(6) pCUT2.2 Clearance

Stamped 3 uL of LBClin cultures (post pEDIT clearance) into 1 mL LB 96DWP. Shake at 42° C., 1000 rpm for 17-20 hrs.

Measured OD600, made 10-4 through 10-7 dilutions in LB, and plated 150 uL onto LB and LBClin divided Qtrays.

Incubated LB and LBClin Qtrays @ 30 C for 20-22 hrs.

Screened for pCUT2.2 clearance (solid media): Qtray wells with growth on LB but not LBClin indicated pCUT2.2 clearance.

Picked n colonies from Qtray wells with growth on LB but not LBClin into 300 uL water. Resuspended colonies and stamped 5 uL into 300 uL LB and LBClin 96MWP.

Confirmed pCUT2.2 clearance (liquid media): Wells with growth in LB, but not LBClin, indicated successful clearance of pCUT2.2.

Banked cultures (mixed 75 uL of culture into 75 uL of 50% glycerol) that cleared pCUT2.2.

Results and Conclusions

Figure 10B:
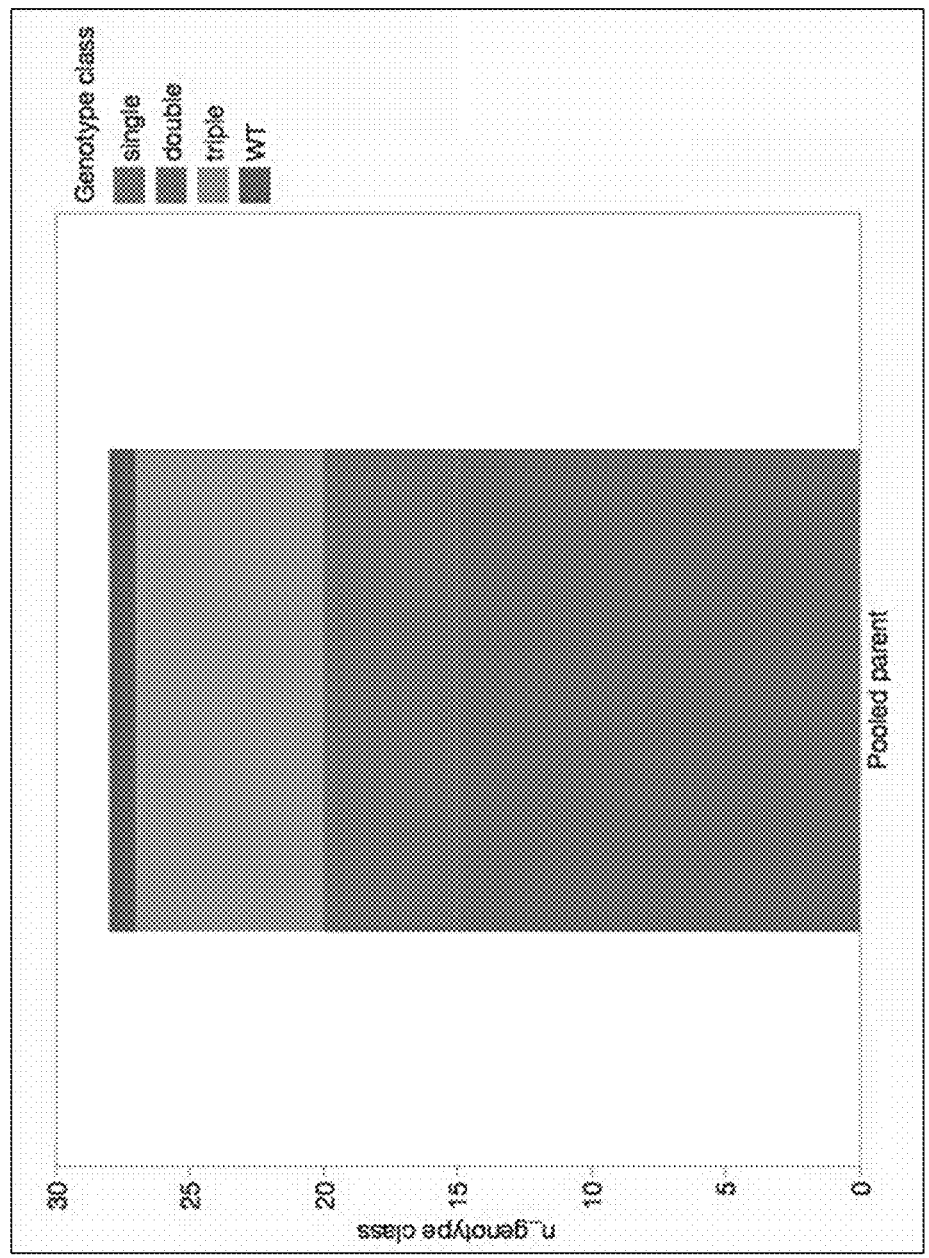
FIGS. 10B-10C show that 26 out of 125 or ~21% of possible genotypes in *E. coli* were captured following application of 4 unique edits/round for 4 rounds using CRISPR mediated homology directed repair in a PPAIS method (no editing occurred in 1 of the 4 rounds and was excluded from the #of possible genotypes).
Figure 10C:
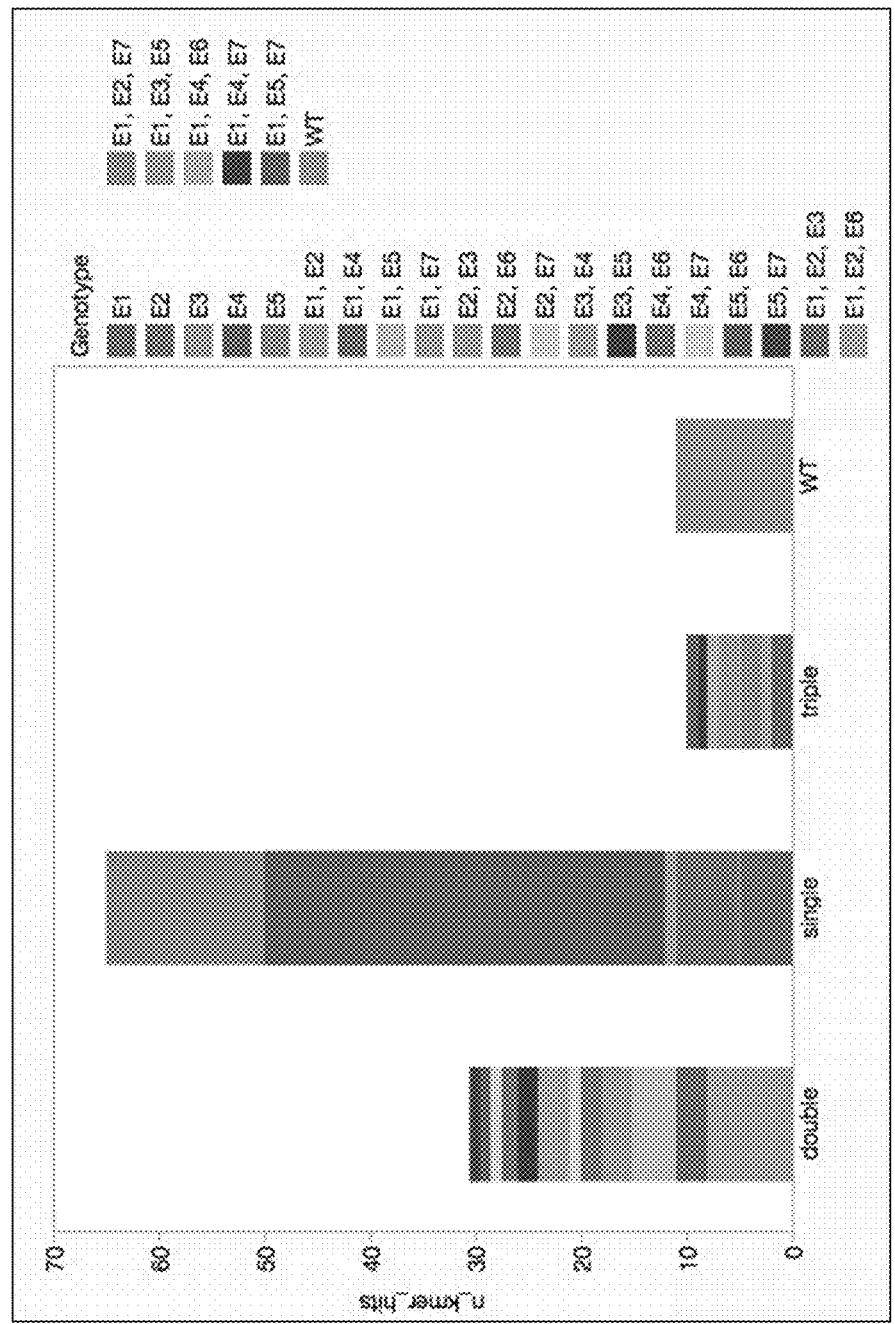

In theory, four (4) unique edits/round for four (4) rounds of PPAIS using CRISPR can produce 625 possible genotypes in *E. coli*. As shown in FIG. 10B-10C, 26 out of 125 or ~21% of possible genotypes in *E. coli* were captured (no editing occurred in 1 of the 4 rounds and was excluded from the #of possible genotypes), indicating that PPAIS using CRISPR can be an effective method for introducing multiple genetic edits across multiple genomic loci.

Example 10—Proof of Principle of Method for Single Iterative Editing with Passive Counterselection Objective This example describes the use of a CRISPR mediated method for using the iterative editing method described in Example 1 but comprises 4 rounds of transformation where the 4$^{th}$ round of transformation uses editing plasmids that have the same selectable marker as was used in the first round of transformation. The objective was to confirm that passive counterselection was effective in clearing previously introduced editing plasmids such that the same selectable markers can be recycled in later rounds of genomic editing. Overall, the use of passive counterselection rather than active counterselection can be used to reduce editing cycle time.

Materials and Methods

Figure 11A:
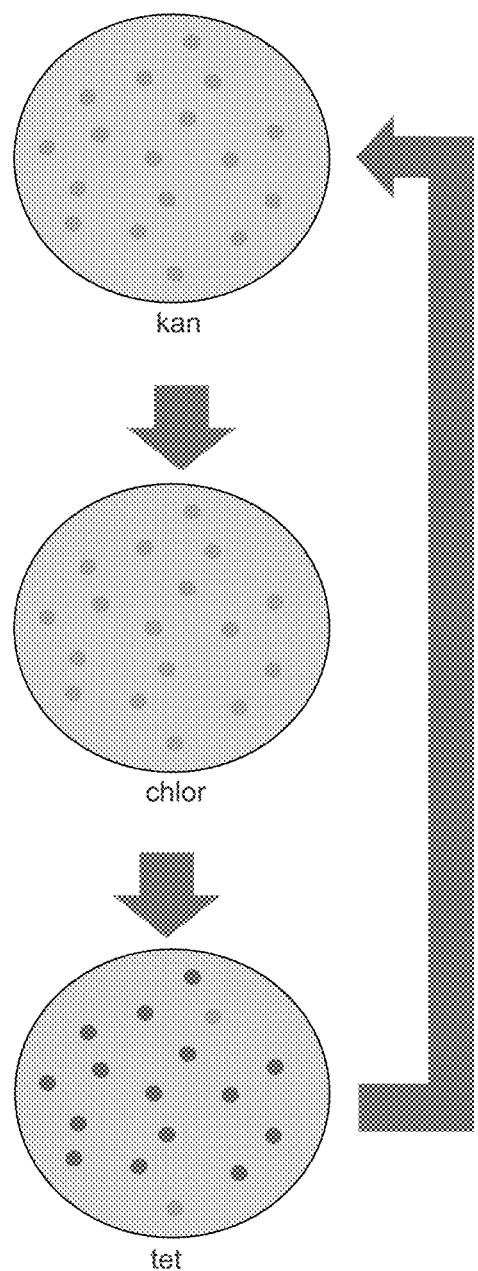
FIG. 11A illustrates the process for single iterative stacking with passive counterselection.

The iterative editing method described in this Example was performed in E. coli host cells essentially as shown in FIGS. 2 and 11A, where a set of 4 editing plasmids comprising one sgRNA/repair fragment pair targeting the same locus and a kanamycin (kan) selectable marker gene were transformed individually into E. coli host cells in the first round of transformation. The transformants were grown on kanamycin containing media; individual colonies were picked and grown in non selective media overnight, pooled (seed) and used to inoculate a main culture essentially as described in Example 9 (each pool of cultures was derived from a single pEDIT plasmid). In round 2, the main culture was transformed with a set of 4 editing plasmids comprising one sgRNA/repair fragment pair targeting the same locus (which was a different locus than the editing plasmids from the first round of transformation) and a chloramphenicol (chlor) selectable marker gene. The transformants were grown on Chlor-containing media; individual colonies were picked and grown in non-selective media overnight, pooled (seed) and used to inoculate a new main culture to be subjected to the third round of transformation. In round 3, the main culture from round 2 was transformed with a set of 4 editing plasmids comprising one sgRNA/repair fragment pair targeting the same locus (which was a different locus than the editing plasmids from the first and second round of transformation) and a tetracycline (tet) selectable marker gene. The transformants were grown on Tet-containing media; individual colonies were picked and grown in non-selective media overnight, pooled (seed) and used to inoculate a new main culture to be subjected to the fourth round of transformation. In round 4, the main culture from round 3 was transformed with a set of 4 editing plasmids comprising one sgRNA/repair fragment pair targeting the same locus (which was a different locus than the editing plasmids from the first, second and third round of transformation) and a Kan selectable marker gene. The transformants were grown on Kan-containing media; individual colonies were grown in non-selective media overnight, transferred to Sucrose-containing media to clear pEDIT, and strains which cleared pEDIT were genotyped using next-generation sequencing (NGS) techniques as known in the art.

Results and Conclusions

Figure 11B:
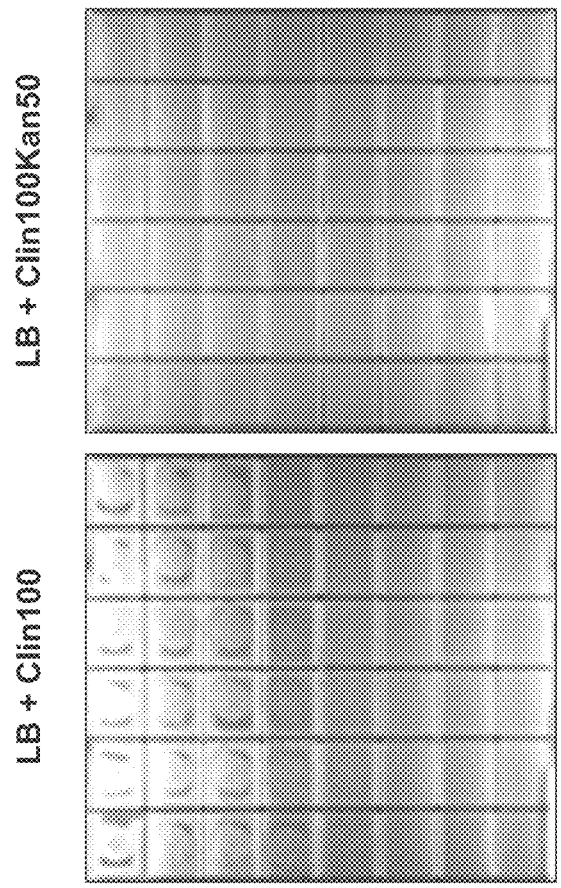
FIG. 11B shows sensitivity of strains to kanamycin following round 3 of transformation.
Figure 11C:
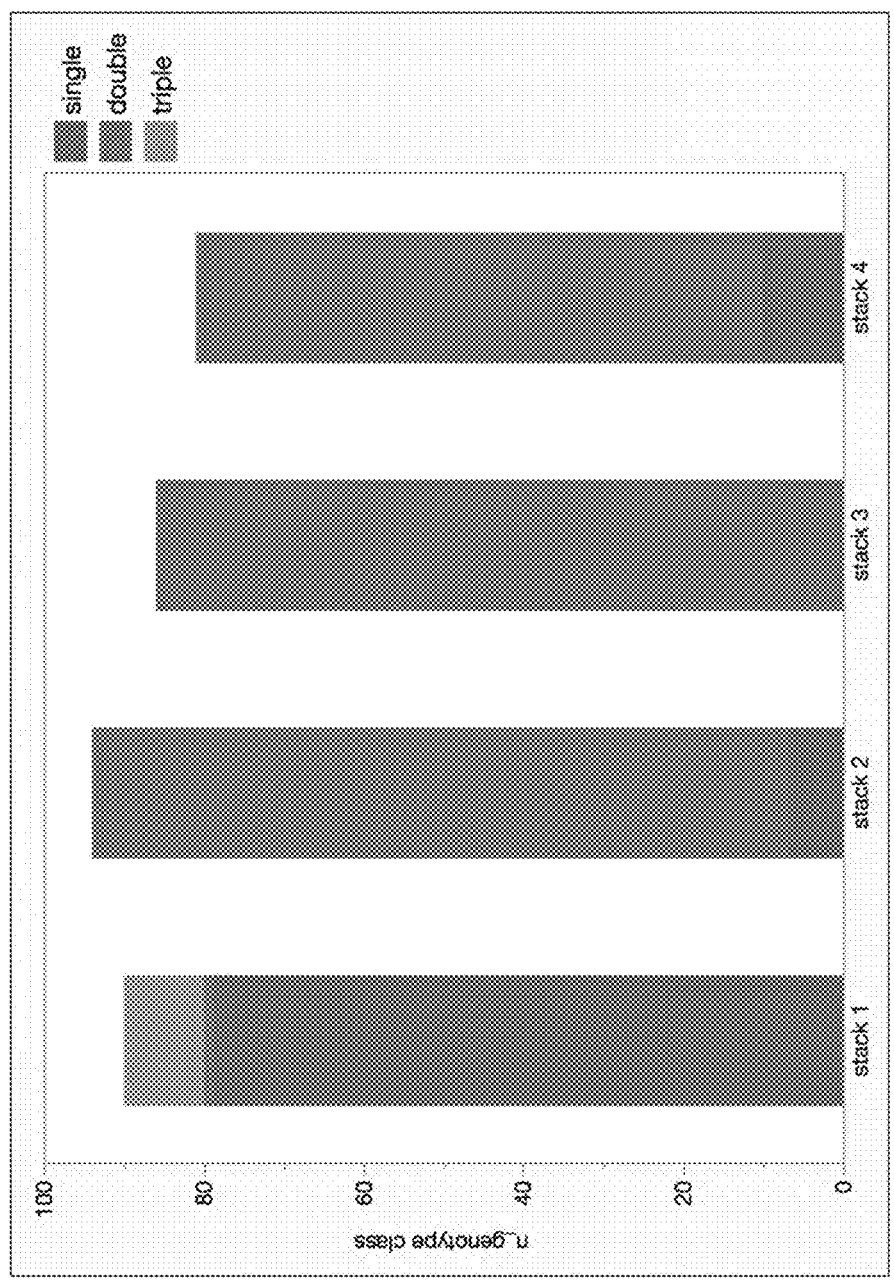
FIG. 11C-11D show that 7 out of 32 or ~22% of possible genotypes in *E. coli* were captured following application of 4 unique edits over 4 rounds using CRISPR mediated homology directed repair (no editing occurred in 1 of the 4 rounds and was excluded from the #of possible genotypes).
Figure 11D:
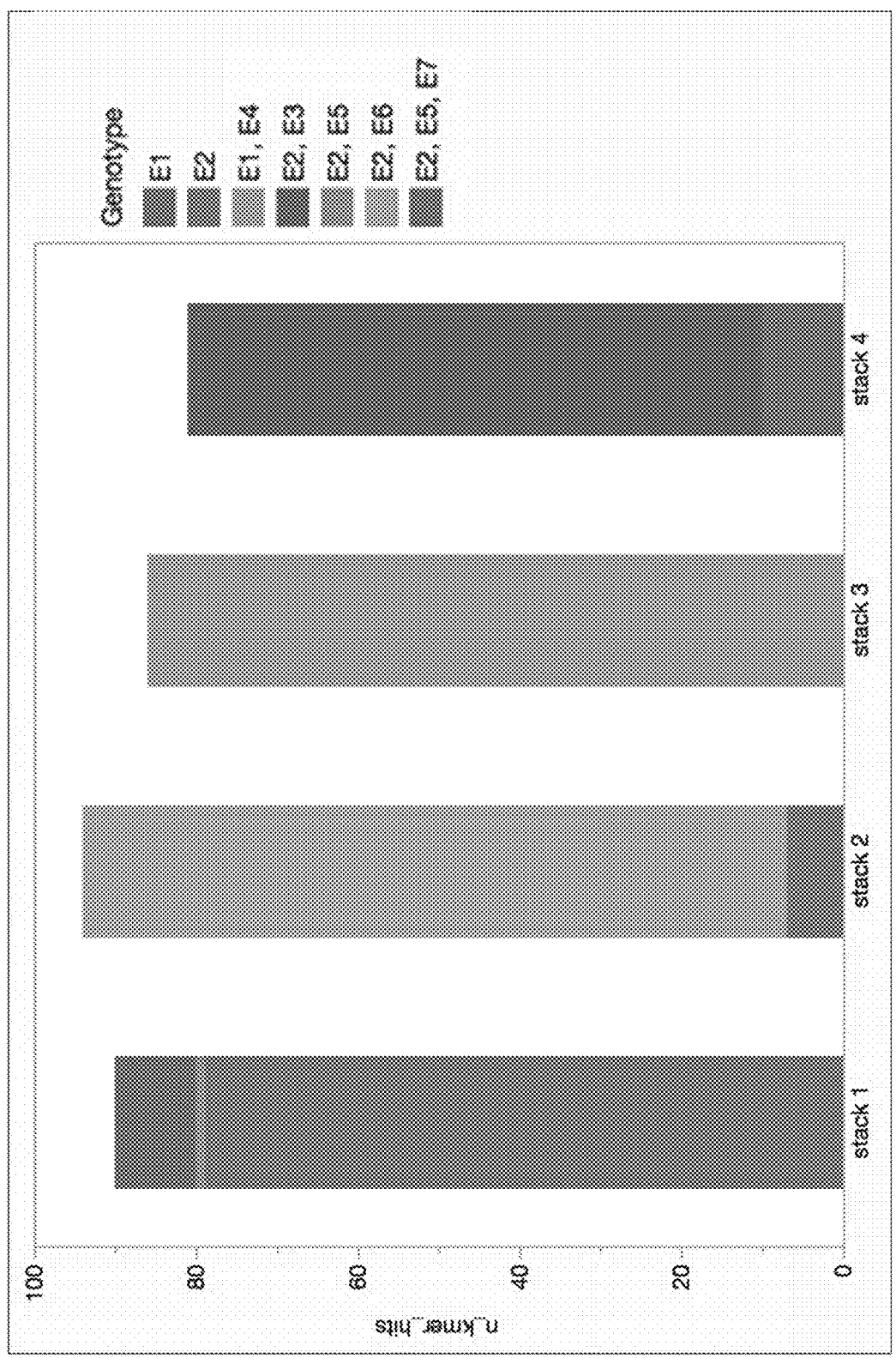

As shown in FIG. 11B, the strains produced post round 3 of transformation were sensitive to Kanamycin, indicating that the Kanamycin resistance gene containing plasmids from round 1 had been cleared. Moreover, FIG. 11C-11D, showed that the strains produced by the iterative editing method of this Example did indeed possess some or all of the desired genetic edits. FIG. 11C-11D showed that 7 out of 32 or ~22% of possible genotypes (no editing occurred in 1 of the 4 rounds and was excluded from the #of possible genotypes) that could have been introduced into E. coli via the introduction of 4 unique edits/round over 4 rounds of transformation described in this Example were captured. Accordingly, 2 rounds of passive counterselection was sufficient for applying the use of a selectable marker gene used at least 2 rounds previously. This process demonstrated that payloads introduced in an iterative process may be used in CRISPR/Cas9 mediated genome editing in E. coli to efficiently and inexpensively generate new E. coli strains.

Numbered Embodiments of the Disclosure

Other subject matter contemplated by the present disclosure is set out in the following numbered embodiments:

1) A method for iteratively editing a microbial host cell genome, the method comprising:
   a. introducing into the microbial host cell a first plasmid comprising a first repair fragment and a selection marker gene, wherein the microbial host cell comprises a site-specific restriction enzyme or a sequence encoding a site-specific restriction enzyme is introduced into the microbial host cell along with the first plasmid, wherein the site-specific restriction enzyme targets a first locus in the genome of the microbial host cell, and wherein the first repair fragment comprises homology arms separated by a sequence for a genetic edit in or adjacent to a first locus in the genome of the microbial host cell, wherein the homology arms comprise sequence homologous to sequence that flanks the first locus in the genome of the microbial host cell;
   b. growing the microbial host cells from step (a) in a media selective for microbial host cells expressing the selection marker gene and isolating microbial host cells from cultures derived therefrom;
   c. growing the microbial host cells isolated in step (b) in media not selective for the selection marker gene and isolating microbial host cells from cultures derived therefrom; and
   d. repeating steps (a)-(c) in one or more additional rounds in the microbial host cells isolated in step (c), wherein each of the one or more additional rounds comprises introducing an additional plasmid comprising an additional repair fragment, wherein the additional repair fragment comprises homology arms separated by a sequence for a genetic edit in or adjacent to a locus in the genome of the microbial host cell, wherein the homology arms comprise sequence homologous to sequence that flanks the locus in the genome of the microbial host cell, wherein the additional plasmid comprises a different selection marker gene than the selection marker gene introduced in a previous round of selection, and wherein the microbial host cell comprises a site-specific restriction enzyme or a sequence encoding a site-specific restriction enzyme is introduced into the microbial host cell along with the additional plasmid that targets the first locus or another locus in the genome of the microbial host cell, thereby iteratively editing the microbial host cell genome; wherein a counterselection is not performed after at least one round of editing.

2) A method for iteratively editing a microbial host cell genome, the method comprising:
   a. introducing into the microbial host cell a first plasmid, a first guide RNA (gRNA) and a first repair fragment, wherein the gRNA comprises a sequence complementary to a first locus in the genome of the microbial host cell, wherein the first repair fragment comprises homology arms separated by a sequence for a genetic edit in or adjacent to a first locus in the genome of the microbial host cell, wherein the homology arms comprise sequence homologous to sequence that flanks the first locus in the genome of the microbial host cell, wherein the first plasmid comprises a selection marker gene and at least one or both of the gRNA and the repair fragment, and wherein:
      i. the microbial host cell comprises an RNA-guided DNA endonuclease; or ii. an RNA-guided DNA endonuclease is introduced into the microbial host cell along with the first plasmid;

b. growing the microbial host cells from step (a) in a media selective for microbial host cells expressing the selection marker gene and isolating microbial host cells from cultures derived therefrom;

c. growing the microbial host cells isolated in step (b) in media not selective for the selection marker gene and isolating microbial host cells from cultures derived therefrom; and d. repeating steps (a)-(c) in one or more additional rounds in the microbial host cells isolated in step (c), wherein each of the one or more additional rounds comprises introducing an additional plasmid, an additional gRNA and an additional repair fragment, wherein the additional gRNA comprises sequence complementary to a locus in the genome of the microbial host cell, wherein the additional repair fragment homology arms separated by a sequence for a genetic edit in or adjacent to a locus in the genome of the microbial host cell, wherein the homology arms comprise sequence homologous to sequence that flanks the locus in the genome of the microbial host cell, wherein the additional plasmid comprises a different selection marker gene than the selection marker gene introduced in a previous round of selection, and wherein the additional plasmid comprises at least one or both of the additional gRNA and the additional repair fragment, thereby iteratively editing the microbial host cell genome; wherein a counterselection is not performed after at least one round of editing.

3) A method for iteratively editing a microbial host cell genome, the method comprising:

a. introducing into the microbial host cell a first plasmid comprising a first repair fragment and a selection marker gene, wherein the first repair fragment comprises homology arms separated by a sequence for a genetic edit in or adjacent to a first locus in the genome of the microbial host cell, wherein the homology arms comprise sequence homologous to sequence that flanks the first locus in the genome of the microbial host cell;

b. growing the microbial host cells from step (a) in a media selective for microbial host cells expressing the selection marker gene and isolating microbial host cells from cultures derived therefrom;

c. growing the microbial host cells isolated in step (b) in media not selective for the selection marker gene and isolating microbial host cells from cultures derived therefrom; and d. repeating steps (a)-(c) in one or more additional rounds in the microbial host cells isolated in step (c), wherein each of the one or more additional rounds comprises introducing an additional plasmid comprising an additional repair fragment, wherein the additional repair fragment comprises homology arms separated by sequence for a genetic edit in or adjacent to a locus in the genome of the microbial host cell, wherein the homology arms comprise sequence homologous to sequence that flanks the locus in the genome of the microbial host cell, and wherein the additional plasmid comprises a different selection marker gene than the selection marker gene introduced in a previous round of selection, thereby iteratively editing the microbial host cell genome; wherein a counterselection is not performed after at least one round of editing.

4) The method of any one of embodiments 1-3, wherein the counterselection is not performed after every round of editing.

5) The method of any one of embodiments 1-3, wherein the counterselection is not performed after any round of editing.

6) The method of any one of embodiments 1-3, wherein the counterselection is not performed after at least one round, after every round, or after any round of editing.

7) The method of any one of embodiments 1-6, wherein the counterselection is an antibiotic, chemical, or temperature-based counterselection.

8) The method of any one of embodiments 1-3, wherein the first and the additional plasmids comprise an identical origin of replication to each other or additional plasmids previously introduced into the microbial host cell.

9) The method of any one of embodiments 1-3, wherein the selection marker gene comprises an antibiotic or auxotrophic selection marker gene.

10) The method of any one of embodiments 1-3, wherein each additional repair fragment comprises sequence for the same genetic edit as one or more of the genetic edits present on a previous repair fragment.

11) The method of any one of embodiments 1-3, wherein each additional repair fragment comprises sequence for a different genetic edit as one or more of the genetic edits present on a previous repair fragment.

12) The method of any one of embodiments 1-3, wherein a plurality of different first repair fragments are introduced, wherein each repair fragment in the plurality of first repair fragments comprises a sequence for a genetic edit in or adjacent to different loci.

13) The method of any one of embodiments 1-3, wherein a plurality of different additional repair fragments are introduced, wherein the plurality of additional repair fragments comprise a sequence for a genetic edit in or adjacent to different loci.

14) The method of embodiment 1, wherein the site-specific restriction enzyme of step (a) cleaves a sequence at the first locus in the genome of the microbial host cell.

15) The method of embodiment 1, wherein the site-specific restriction enzyme of step (d) cleaves a sequence at the locus targeted in each of the one or more additional rounds in the genome of the microbial host cell.

16) The method of embodiment 1, wherein the site-specific restriction enzyme of step (a) and/or step (d) is selected from the group consisting of an RNA-guided DNA endonuclease, a meganuclease, a transcription activator-like effector nucleases (TALEN), and a zinc-finger nuclease (ZFN).

17) The method of embodiment 1, wherein the site-specific restriction enzyme of step (a) and/or step (d) is encoded on a plasmid, encoded in the genome, translated from RNA, or introduced into the cell as protein.

18) The method of embodiment 16, wherein the RNA-guided DNA endonuclease of step (a) cleaves a sequence at the first locus in the genome of the microbial host cell.

19) The method of embodiment 16, wherein the RNA-guided DNA endonuclease of step (d) cleaves a sequence at the locus targeted in each of the one or more additional rounds in the genome of the microbial host cell.

20) The method of embodiment 2, wherein the RNA-guided DNA endonuclease cleaves a sequence at the first locus from step (a) in the genome of the microbial host cell and the locus from step (d) in the genome of the microbial host cell in each of the one or more additional rounds.

21) The method of any one of embodiments 1-2, 16, or 20, wherein the RNA-guided DNA endonuclease is selected from Cas9, Cas12a, Cas12b, Cas12c, Cas12d, Cas12e, Cas13a, Cas13b, Cas13c, Cpf1, and MAD7, or homologs, orthologs or paralogs thereof.

22) The method of embodiment 2, wherein the RNA-guided DNA endonuclease is encoded on a plasmid, encoded in the genome, translated from RNA, or introduced into the cell as protein.

23) The method of embodiment 2, wherein the first plasmid comprises the first gRNA and the first repair fragment.

24) The method of embodiment 2, wherein the additional plasmid comprises the additional gRNA and the additional repair fragment.

25) The method of embodiment 2, wherein the first gRNA and/or the additional gRNA is provided as a linear fragment.

26) The method of embodiment 2, wherein the first repair fragment and/or the additional repair fragment is/are provided as a linear fragment, and, optionally, wherein the first repair fragment and/or the additional repair fragment is provided as ssDNA or dsDNA.

27) The method of embodiment 2, wherein the first gRNA and/or the additional gRNA comprise a CRISPR RNA (crRNA) and a trans-activating crRNA (tracrRNA).

28) The method of embodiment 2, wherein the first gRNA and/or the additional gRNA is a single gRNA (sgRNA).

29) The method of any one of the above embodiments, wherein the genetic edit is selected from the group consisting of an insertion, a deletion, a single nucleotide polymorphism, a genome shuffling, a large scale deletion, a genomic edit, a plasmid edit, and multiple edits, or any combination thereof.

30) The method of any one of the above embodiments, wherein the additional repair fragment introduced in each of the one or more additional rounds target a different locus and are associated with a different selection marker gene from a previous round of editing.

31) The method of embodiment 2, wherein the additional gRNA introduced in each of the one or more additional rounds target a different locus and are associated with a different antibiotic selection marker gene from a previous round of editing.

32) The method of embodiment 1, further comprising step (e), wherein step (e) comprises introducing a final plasmid comprising a final repair fragment in a terminal round of repeating steps (a)-(c), wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a sequence for a different selection marker gene than the selection marker gene introduced in a previous round of selection, wherein the microbial host cell comprises a site-specific restriction enzyme or a sequence encoding a site-specific restriction enzyme is introduced into the microbial host cell along with the final plasmid that targets the final locus in the genome of the microbial host cell.

33) The method of embodiment 2, further comprising step (e), wherein step (e) comprises introducing a final plasmid, a final gRNA and a final repair fragment in a terminal round of repeating steps (a)-(c), wherein the final gRNA comprises a sequence complementary to a final locus in the genome of the microbial host cell, wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a different selection marker gene than the selection marker gene introduced in a previous round of selection, and wherein the final plasmid comprises at least one or both of the final gRNA and the final repair fragment.

34) The method of embodiment 3, further comprising step (e), wherein step (e) comprises introducing a final plasmid comprising a final repair fragment in a terminal round of repeating steps (a)-(c), wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a different selection marker gene than the selection marker gene introduced in a previous round of selection.

35) The method of any one of embodiments 32-34, wherein the final locus is a different locus from any locus edited previously.

36) The method of embodiment 33, wherein the final locus is a different locus from any locus targeted by a gRNA previously introduced into the microbial host cell.

37) The method of any one of embodiments 32-36, further comprising a step (f), wherein step (f) comprises introducing a gRNA comprising a guide sequence complementary to a sequence present on or associated with the final repair fragment to facilitate removal of the final repair fragment following the terminal round via an RNA-guided DNA endonuclease.

38) The method of any one of embodiments 1-3, wherein the microbial host cell comprises a set of proteins from one or more heterologous recombination systems.

39) The method of any one of embodiments 1-3, wherein the microbial host cell comprises a set of proteins from a heterologous recombination system selected from a lambda red recombination system, a RecET recombination system, a Red/ET recombination system, any homologs, orthologs or paralogs of proteins from a lambda red recombination system or a RecET recombination system, or any combination thereof.

40) The method of embodiment 39, wherein the set of proteins from the lambda red recombination system comprise a beta protein, a gam protein, and an exo protein.

41) The method of any one of embodiments 38-40, wherein the set of proteins from the heterologous recombination system are introduced into the microbial host cell on a plasmid comprising genes encoding the set of proteins from the heterologous recombination system prior to step (a).

42) The method of any one of embodiments 38-41, wherein the set of proteins from the heterologous recombination system are stably expressed by the microbial host cell due to integration of genes encoding the set of proteins from the heterologous recombination system into the microbial host cell's genome.

43) The method of any one of embodiments 38-42, wherein the set of proteins from the heterologous recombination system are in an operon operably linked to an inducible promoter.

44) The method of embodiment 43, wherein the inducible promoter is inducible by addition or depletion of a reagent or by a change in temperature.

45) The method of embodiment 44, wherein the reagent is selected from the group consisting of arabinose, isopropyl beta-D-1-thiogalactopyranoside (IPTG), and tetracycline.

46) The method of any one of the above embodiments, wherein the introducing steps comprise transforming the microbial host cell.

47) The method of any one of the above embodiments, wherein the microbial host cell is a eukaryotic cell.

48) The method of embodiment 47, wherein the microbial host cell is a yeast cell.

49) The method of embodiment 48, wherein the yeast cell is *Saccharomyces cerevisiae* 50) The method of embodiment 47, wherein the microbial host cell is a filamentous fungus.

51) The method of embodiment 50, wherein the filamentous fungus is *Aspergillus niger*.

52) The method of any one of embodiments 1-46, wherein the microbial host cell is a prokaryotic cell.

53) The method of embodiment 52, wherein the prokaryotic host cell is *Escherichia coli* or *Corynebacterium glutamicum*.

54) A method for clearing a previously present plasmid from a microbial host cell, the method comprising:
  a. introducing into the microbial host cell comprising a previously present plasmid a first plasmid comprising a first selection marker gene; and
  b. growing the microbial host cells from step (a) in a media selective for microbial host cells expressing the selection marker gene and isolating microbial host cells from cultures derived therefrom, wherein the previously present and the introduced first plasmids comprise an identical origin of replication, thereby clearing the previously present plasmid from a microbial host cell; wherein a counterselection is not performed to facilitate clearance of a previously present plasmid.

55) The method of embodiment 54, further comprising step (c), comprising growing the microbial host cells isolated in step (b) in media not selective for the selection marker gene and isolating microbial host cells from cultures derived therefrom.

56) The method of embodiment 55, further comprising repeating steps (a)-(c) in one or more rounds, wherein each of the one or more rounds comprises introducing an additional plasmid comprising a different selection marker gene than the selection marker gene introduced in a previous round of selection, wherein the previously present and additionally introduced plasmids comprise an identical origin of replication.

57) The method of any one of embodiments 54-56, wherein the previously present plasmid is a native plasmid or a heterologous plasmid.

58) A method for iteratively clearing a previously introduced plasmid from a microbial host cell, the method comprising:
  a. introducing into the microbial host cell a first plasmid comprising a first selection marker gene;
  b. growing the microbial host cells from step (a) in a media selective for microbial host cells expressing the selection marker gene and isolating microbial host cells from cultures derived therefrom;
  c. growing the microbial host cells isolated in step (b) in media not selective for the selection marker gene and isolating microbial host cells from cultures derived therefrom; and
  d. repeating steps (a)-(c) in one or more rounds, wherein each of the one or more rounds comprises introducing an additional plasmid comprising a different selection marker gene than the selection marker gene introduced in a previous round of selection, and wherein the first and the additional plasmids comprise an identical origin of replication to each other first or additional plasmid previously introduced into the microbial host cell, thereby iteratively clearing the previously introduced first or additional plasmid from a microbial host cell; wherein a counterselection is not performed to facilitate clearance of a previously introduced plasmid.

59) The method of embodiment 54 or embodiment 58, wherein the counterselection is not performed after at least one round, after every round, or after any round of editing.

60) The method of embodiment 54 or embodiment 58, wherein the counterselection is an antibiotic, chemical, or temperature-based counterselection, and the counterselection is not performed after at least one round, after every round, or after any round of editing.

61) The method of any one of embodiments 54-60, wherein the selection marker gene comprises an antibiotic or auxotrophic selection marker gene.

62) The method of any one of embodiments 54-61, wherein the introducing steps comprise transforming the microbial host cell.

63) The method of any one of embodiments 54-62, wherein the microbial host cell is a eukaryotic cell.

64) The method of embodiment 63, wherein the microbial host cell is a yeast cell.

65) The method of embodiment 64, wherein the yeast cell is *Saccharomyces cerevisiae* 66) The method of embodiment 63, wherein the microbial host cell is a filamentous fungus.

67) The method of embodiment 66, wherein the filamentous fungus is *Aspergillus niger*.

68) The method of any one of embodiments 54-62, wherein the microbial host cell is a prokaryotic cell.

69) The method of embodiment 68, wherein the prokaryotic host cell is *Escherichia coli* or *Corynebacterium glutamicum*.

70) The method of any one of the above embodiments, further comprising genotyping microbial host cells grown in a media selective for microbial host cells expressing a selection marker gene or in a media not selective for a selection marker gene.

71) A method for generating a library of genetically edited microbial strains, the method comprising:
  (a) introducing a selection marker gene and a first genetic edit into the genome of each individual microbial host cell from a plurality of microbial host cells, wherein the first genetic edit introduced into the genome of each individual microbial host cell from the plurality of microbial host cells is different than the first genetic edit introduced into the genome of each other individual microbial host cell from the plurality of microbial host cells;
  (b) clearing the selection marker gene from each of the individual microbial host cells from step (a) to generate individual microbial host cells comprising a first genetic edit that is cleared of the selectable marker gene;
  (c) mixing each of the individual microbial host cells from step (b) to form a main culture;
  (d) dividing the main culture of step (c) into separate microbial host cell cultures; and
  (e) repeating steps (a)-(d) for one or more additional rounds, wherein each of the one or more additional rounds comprises introducing a different selection marker gene than the selection marker gene introduced in a previous round of selection and a different genetic edit than the first genetic edit introduced in a previous round, thereby generating a library of genetically edited microbial strains.

72) The method of embodiment 71, wherein the introducing the selectable marker gene and the first genetic edit in step (a) comprises introducing into the individual microbial host cell a first plasmid comprising a first repair fragment and the selection marker gene, wherein the individual microbial host cell comprises a site-specific restriction enzyme or a sequence encoding a site-specific restriction enzyme is introduced into the individual microbial host cell along with the first plasmid, wherein the site-specific restriction enzyme targets a first locus in the genome of the individual microbial host cell, and wherein the first repair fragment comprises homology arms separated by a sequence for the first genetic edit in or adjacent to the first locus in the genome of the individual microbial host cell, wherein the homology arms comprise sequence homologous to sequence that flanks the first locus in the genome of the individual microbial host cell.

73) The method of embodiment 72, wherein the one or more additional rounds of step (e) comprises introducing into each individual microbial host cell from the main culture of step (c) an additional plasmid comprising an additional repair fragment, wherein the additional repair fragment comprises homology arms separated by a sequence for a genetic edit in or adjacent to a locus in the genome of the microbial host cell, wherein the homology arms comprise sequence homologous to sequence that flanks the locus in the genome of the microbial host cell, wherein the additional plasmid comprises a different selection marker gene than the selection marker gene introduced in a previous round of selection, and wherein the microbial host cell comprises a site-specific restriction enzyme or a sequence encoding a site-specific restriction enzyme is introduced into the microbial host cell along with the additional plasmid that targets the first locus or another locus in the genome of the microbial host cell.

74) The method of embodiment 71, wherein the introducing the selectable marker gene and first genetic edit comprises introducing into the individual microbial host cell a first plasmid, a first guide RNA (gRNA) and a first repair fragment, wherein the gRNA comprises a sequence complementary to a first locus in the genome of the individual microbial host cell, wherein the first repair fragment comprises homology arms separated by a sequence for the first genetic edit in or adjacent to a first locus in the genome of the individual microbial host cell, wherein the homology arms comprise sequence homologous to sequence that flanks the first locus in the genome of the individual microbial host cell, wherein the first plasmid comprises the selection marker gene and at least one or both of the gRNA and the repair fragment, and wherein:
  i. the individual microbial host cell comprises an RNA-guided DNA endonuclease; or
  ii. an RNA-guided DNA endonuclease is introduced into the individual microbial host cell along with the first plasmid.

75) The method of embodiment 74, wherein the one or more additional rounds of step (e) comprises introducing into each individual microbial host cell from the main culture of step (c) an additional plasmid, an additional gRNA and an additional repair fragment, wherein the additional gRNA comprises sequence complementary to a locus in the genome of the microbial host cell, wherein the additional repair fragment homology arms separated by a sequence for a genetic edit in or adjacent to a locus in the genome of the microbial host cell, wherein the homology arms comprise sequence homologous to sequence that flanks the locus in the genome of the microbial host cell, wherein the additional plasmid comprises a different selection marker gene than the selection marker gene introduced in a previous round of selection, and wherein the additional plasmid comprises at least one or both of the additional gRNA and the additional repair fragment.

76) The method of embodiment 71, wherein the introducing the selectable marker gene and first genetic edit comprises introducing into the individual microbial host cell a first plasmid comprising a first repair fragment and the selection marker gene, wherein the first repair fragment comprises homology arms separated by a sequence for the first genetic edit in or adjacent to a first locus in the genome of the individual microbial host cell, wherein the homology arms comprise sequence homologous to sequence that flanks the first locus in the genome of the individual microbial host cell.

77) The method of embodiment 76, wherein the one or more additional rounds of step (e) comprises introducing into each individual microbial host cell from the main culture of step (c) an additional plasmid comprising an additional repair fragment, wherein the additional repair fragment comprises homology arms separated by sequence for a genetic edit in or adjacent to a locus in the genome of the microbial host cell, wherein the homology arms comprise sequence homologous to sequence that flanks the locus in the genome of the microbial host cell, and wherein the additional plasmid comprises a different selection marker gene than the selection marker gene introduced in a previous round of selection.

78) The method of any one of embodiments 71-77, wherein the clearing the selection marker gene comprises: (a) growing the individual microbial host cells from step in a media selective for individual microbial host cells expressing the selection marker gene and isolating microbial host cells from cultures derived therefrom; and (b) growing the microbial host cells isolated in step (a) in media not selective for the selection marker gene and isolating microbial host cells from cultures derived therefrom.

79) The method of any one of embodiments 71-78, wherein a counterselection is not performed after at least one round of editing to facilitate clearance of a previously introduced selection marker gene.

80) The method of embodiment 79, wherein the counterselection is not performed after every round of editing.

81) The method of embodiment 79, wherein the counterselection is not performed after any round of editing.

82) The method of embodiment 79, wherein the counterselection is not performed after at least one round, after every round, or after any round of editing.

83) The method of any one of embodiments 79-82, wherein the counterselection is an antibiotic, chemical, or temperature-based counterselection.

84) The method of any one of embodiments 72-77, wherein the first and the additional plasmids, comprise an identical origin of replication to each other or additional plasmids previously introduced into the microbial host cell.

85) The method of any one of embodiments 71-84, wherein the selection marker gene comprises an antibiotic or auxotrophic selection marker gene.

86) The method of any one of embodiments 72-77, wherein each additional repair fragment comprises sequence for the same genetic edit as one or more of the genetic edits present on a previous repair fragment.

87) The method of any one of embodiments 72-77, wherein each additional repair fragment comprises sequence for a different genetic edit as one or more of the genetic edits present on a previous repair fragment.

88) The method of embodiment 72, wherein the site-specific restriction enzyme cleaves a sequence at the first locus in the genome of the microbial host cell.

89) The method of embodiment 73, wherein the site-specific restriction enzyme cleaves a sequence at the locus targeted in each of the one or more additional rounds in the genome of the microbial host cell.

90) The method of embodiment 72, wherein the site-specific restriction enzyme is selected from the group consisting of an RNA-guided DNA endonuclease, a meganuclease, a transcription activator-like effector nucleases (TALEN), and a zinc-finger nuclease (ZFN).

91) The method of embodiment 73, wherein the site-specific restriction enzyme is selected from the group consisting of an RNA-guided DNA endonuclease, a meganuclease, a transcription activator-like effector nucleases (TALEN), and a zinc-finger nuclease (ZFN).

92) The method of embodiment 72, wherein the site-specific restriction enzyme is encoded on a plasmid, encoded in the genome, translated from RNA, or introduced into the cell as protein.

93) The method of embodiment 73, wherein the site-specific restriction enzyme is encoded on a plasmid, encoded in the genome, translated from RNA, or introduced into the cell as protein.

94) The method of embodiment 90, wherein the RNA-guided DNA endonuclease cleaves a sequence at the first locus in the genome of the microbial host cell.

95) The method of embodiment 91, wherein the RNA-guided DNA endonuclease cleaves a sequence at the locus targeted in each of the one or more additional rounds in the genome of the microbial host cell.

96) The method of embodiment 74, wherein the RNA-guided DNA endonuclease cleaves a sequence at the first locus in the genome of the microbial host cell and the locus in the genome of the microbial host cell in each of the one or more additional rounds.

97) The method of any one of embodiments 94-96, wherein the RNA-guided DNA endonuclease is selected from Cas9, Cas12a, Cas12b, Cas12c, Cas12d, Cas12e, Cas13a, Cas13b, Cas13c, Cpf1, and MAD7, or homologs, orthologs or paralogs thereof.

98) The method of embodiment 74, wherein the RNA-guided DNA endonuclease is encoded on a plasmid, encoded in the genome, translated from RNA, or introduced into the cell as protein.

99) The method of embodiment 74, wherein the first plasmid comprises the first gRNA and the first repair fragment.

100) The method of embodiment 75, wherein the additional plasmid comprises the additional gRNA and the additional repair fragment.

101) The method of embodiment 74 or 75, wherein the first gRNA and/or the additional gRNA is provided as a linear fragment.

102) The method of embodiment 74 or 75, wherein the first repair fragment and/or the additional repair fragment is/are provided as a linear fragment, and, optionally, wherein the first repair fragment and/or the additional repair fragment is provided as ssDNA or dsDNA.

103) The method of embodiment 74 or 75, wherein the first gRNA and/or the additional gRNA comprise a CRISPR RNA (crRNA) and a trans-activating crRNA (tracrRNA).

104) The method of embodiment 74 or 75, wherein the first gRNA and/or the additional gRNA is a single gRNA (sgRNA).

105) The method of any one of embodiments 72-77, wherein the genetic edit is selected from the group consisting of an insertion, a deletion, a single nucleotide polymorphism, a genome shuffling, a large scale deletion, a genomic edit, a plasmid edit, and multiple edits, or any combination thereof.

106) The method of any one of embodiments 73, 75 or 77, wherein the additional repair fragment introduced in each of the one or more additional rounds target a different locus and are associated with a different selection marker gene from a previous round of editing.

107) The method of embodiment 75, wherein the additional gRNA introduced in each of the one or more additional rounds target a different locus and are associated with a different antibiotic selection marker gene from a previous round of editing.

108) The method of embodiment 73, further comprising step (f), wherein step (f) comprises introducing a final plasmid comprising a final repair fragment in a terminal round of repeating steps (a)-(d), wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a sequence for a different selection marker gene than the selection marker gene introduced in a previous round of selection, wherein the microbial host cell comprises a site-specific restriction enzyme or a sequence encoding a site-specific restriction enzyme is introduced into the microbial host cell along with the final plasmid that targets the final locus in the genome of the microbial host cell.

109) The method of embodiment 75, further comprising step (f), wherein step (f) comprises introducing a final plasmid, a final gRNA and a final repair fragment in a terminal round of repeating steps (a)-(d), wherein the final gRNA comprises a sequence complementary to a final locus in the genome of the microbial host cell, wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a different selection marker gene than the selection marker gene introduced in a previous round of selection, and wherein the final plasmid comprises at least one or both of the final gRNA and the final repair fragment.

110) The method of embodiment 77, further comprising step (f), wherein step (f) comprises introducing a final plasmid comprising a final repair fragment in a terminal round of repeating steps (a)-(d), wherein the final repair fragment comprises homology arms separated by a sequence for a genetic edit in or adjacent to a final locus in the genome of the microbial host cell, wherein the homology arms comprise sequence homologous to sequence that flanks the final locus in the genome of the microbial host cell, and wherein the final plasmid comprises a different selection marker gene than the selection marker gene introduced in a previous round of selection.

111) The method of any one of embodiments 108-110, wherein the final locus is a different locus from any locus edited previously.

112) The method of embodiment 109, wherein the final locus is a different locus from any locus targeted by a gRNA previously introduced into the microbial host cell.

113) The method of any one of embodiments 108-110, further comprising a step (f), wherein step (f) comprises introducing a gRNA comprising a guide sequence complementary to a sequence present on or associated with the final repair fragment to facilitate removal of the final repair fragment following the terminal round via an RNA-guided DNA endonuclease.

114) The method of embodiment 71, wherein each individual microbial host cell comprises a set of proteins from one or more heterologous recombination systems.

115) The method of embodiment 71, wherein each individual microbial host cell comprises a set of proteins from a heterologous recombination system selected from a lambda red recombination system, a RecET recombination system, a Red/ET recombination system, any homologs, orthologs or paralogs of proteins from a lambda red recombination system or a RecET recombination system, or any combination thereof.

116) The method of embodiment 115, wherein the set of proteins from the lambda red recombination system comprise a beta protein, a gam protein, and an exo protein.

117) The method of embodiment 114, wherein the set of proteins from the heterologous recombination system are introduced into each individual microbial host cell on a plasmid comprising genes encoding the set of proteins from the heterologous recombination system prior to step (a).

118) The method of embodiment 114, wherein the set of proteins from the heterologous recombination system are stably expressed by each individual microbial host cell due to integration of genes encoding the set of proteins from the heterologous recombination system into the microbial host cell's genome.

119) The method of embodiment 114, wherein the set of proteins from the heterologous recombination system are in an operon operably linked to an inducible promoter.

120) The method of embodiment 119, wherein the inducible promoter is inducible by addition or depletion of a reagent or by a change in temperature.

121) The method of embodiment 120, wherein the reagent is selected from the group consisting of arabinose, isopropyl beta-D-1-thiogalactopyranoside (IPTG), and tetracycline.

122) The method of embodiment 71, wherein the introducing steps comprise transforming each individual microbial host cell.

123) The method of embodiment 71, wherein each individual microbial host cell is a eukaryotic cell.

124) The method of embodiment 123, wherein each individual microbial host cell is a yeast cell.

125) The method of embodiment 124, wherein the yeast cell is *Saccharomyces cerevisiae*.

126) The method of embodiment 123, wherein the microbial host cell is a filamentous fungus.

127) The method of embodiment 126, wherein the filamentous fungus is *Aspergillus niger*.

128) The method of embodiment 71, wherein each individual microbial host cell is a prokaryotic cell.

129) The method of embodiment 128, wherein the prokaryotic host cell is *Escherichia coli* or *Corynebacterium glutamicum*.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

What is claimed:
1. A method for iteratively editing a microbial host cell's genome, the method comprising:
(a) introducing into the microbial host cell an editing plasmid, a first guide RNA (gRNA) and a first repair fragment, wherein the gRNA comprises a sequence complementary to a first locus in the genome of the microbial host cell, wherein the first repair fragment comprises homology arms separated by a sequence for a genetic edit in or adjacent to the first locus in the genome of the microbial host cell, wherein the homology arms comprise sequence homologous to sequence that flanks the first locus in the genome of the microbial host cell, wherein the editing plasmid comprises a selection marker gene and at least one or both of a gene encoding the first gRNA and the first repair fragment, and wherein:
(i) the microbial host cell comprises an RNA-guided DNA endonuclease; or
(ii) an RNA-guided DNA endonuclease is introduced into the microbial host cell along with the editing plasmid;
(b) growing the microbial host cell from step (a) in media selective for microbial host cells expressing the selection marker gene in the editing plasmid, thereby creating an edited microbial host cell;
(c) introducing into the edited microbial host cell of the previous step an additional editing plasmid, an additional gRNA and an additional repair fragment, wherein the additional gRNA comprises sequence complementary to an additional locus in the genome of the edited microbial host cell, wherein the additional repair fragment comprises homology arms separated by a sequence for a genetic edit in or adjacent to the additional locus in the genome of the edited microbial host cell, wherein the homology arms comprise sequence homologous to sequence that flanks the additional locus in the genome of the edited microbial host cell, wherein the additional editing plasmid comprises a selection marker gene that is different from the selection marker gene introduced in the previous introducing step, and wherein the additional editing plasmid comprises at least one or both of a gene encoding the additional gRNA and the additional repair fragment, thereby iteratively editing the microbial host cell genome; and

(d) growing the edited microbial host cell from the previous step in media selective for microbial host cells expressing the selection marker gene in the additional editing plasmid of the previous step, thereby clearing the editing plasmids lacking the selection marker gene in the additional editing plasmid of the previous step from the edited microbial host cell from the previous step; wherein a counterselection is not performed before step (c).

2. The method of claim 1, comprising step (e) repeating steps (c) and (d) one or more times for one or more additional rounds of gene editing.

3. The method of claim 2, wherein the additional repair fragment introduced in each of the one or more additional rounds of editing, comprises homology arms with sequence homologous to sequence that flanks a different locus in the genome and wherein the additional repair fragment comprises a selection marker gene that is different from the selection marker gene introduced in a previous round of editing.

4. The method of claim 2, wherein the additional gRNA introduced in each of the one or more additional rounds of editing targets a different locus in the genome and is associated with a different selection marker gene from a previous round of editing.

5. The method of claim 1, wherein the editing plasmid of step (a) and the additional editing plasmid of step (c) comprise an identical origin of replication.

6. The method of claim 1, wherein the additional repair fragment comprises sequence for the same genetic edit as one or more of the genetic edits present on a previous repair fragment.

7. The method of claim 1, wherein the additional repair fragment comprises sequence for a different genetic edit as one or more of the genetic edits present on a previous repair fragment.

8. The method of claim 1, wherein a plurality of different first repair fragments are introduced, wherein each repair fragment in the plurality of first repair fragments comprises a sequence for a genetic edit in or adjacent to different loci.

9. The method of claim 1, wherein a plurality of different additional repair fragments are introduced, wherein the plurality of additional repair fragments comprise a sequence for a genetic edit in or adjacent to different loci.

10. The method of claim 1, wherein the RNA-guided DNA endonuclease cleaves a sequence at the first locus from step (a) in the genome of the microbial host cell and the additional locus from step (c) in the genome of the microbial host cell.

11. The method of claim 1, wherein the RNA-guided DNA endonuclease is selected from Cas9, Cas12a, Cas12b, Cas12c, Cas12d, Cas12e, Cas13a, Cas13b, Cas13c, Cpf1, and MAD7, or homologs, orthologs or paralogs thereof.

12. The method of claim 1, wherein the editing plasmid comprises the gene encoding the first gRNA and the first repair fragment.

13. The method of claim 1, wherein the additional editing plasmid comprises the gene encoding the additional gRNA and the additional repair fragment.

14. The method of claim 1, wherein the gene encoding the first gRNA and/or the additional gRNA is provided as a linear fragment.

15. The method of claim 1, wherein the first repair fragment and/or the additional repair fragment is/are provided as a linear fragment, and, wherein the first repair fragment and/or the additional repair fragment is provided as ssDNA or dsDNA.

16. The method of claim 1, wherein the genetic edit is selected from the group consisting of an insertion, a deletion, a single nucleotide polymorphism, a genome shuffling, a large scale deletion, a genomic edit, a plasmid edit, and multiple edits, or any combination thereof.

17. The method of claim 1, further comprising a final plasmid, a final gRNA and a final repair fragment in a terminal round of editing, wherein the final gRNA comprises a sequence complementary to a final locus in the genome of the microbial host cell, wherein the final repair fragment comprises homology arms separated by a sequence for a genetic edit in or adjacent to the final locus in the genome of the microbial host cell, wherein the homology arms comprise sequence homologous to sequence that flanks the final locus in the genome of the microbial host cell, and wherein the final plasmid comprises a selection marker gene that is different from the selection marker gene introduced in the previous round of selection, and wherein the final plasmid comprises at least one or both of a gene encoding the final gRNA and the final repair fragment.

18. The method of claim 17, wherein the final locus is a different locus from any locus targeted by a gRNA previously introduced into the microbial host cell.

19. The method of claim 17, further comprising introducing a gRNA comprising a guide sequence complementary to a sequence present on the final plasmid comprising the final repair fragment to facilitate removal of the final repair fragment.

20. The method of claim 1, wherein the microbial host cell is a yeast cell or a filamentous fungus.

21. The method of claim 20, wherein the yeast cell is *Saccharomyces cerevisiae*.

22. The method of claim 20, wherein the filamentous fungus is *Aspergillus niger*.

23. The method of claim 1, wherein the microbial host cell is *Escherichia coli* or *Corynebacterium glutamicum*.

24. A method for iteratively editing a microbial host cell's genome, the method comprising:
(a) introducing into the microbial host cell an editing plasmid, a first guide RNA (gRNA) and a first repair fragment, wherein the gRNA comprises a sequence complementary to a first locus in the genome of the microbial host cell, wherein the first repair fragment comprises homology arms separated by a sequence for a genetic edit in or adjacent to the first locus in the genome of the microbial host cell, wherein the homology arms comprise sequence homologous to sequence that flanks the first locus in the genome of the microbial host cell, wherein the editing plasmid comprises a selection marker gene and at least one or both of a gene encoding the first gRNA and the first repair fragment, and wherein:
(i) the microbial host cell comprises an RNA-guided DNA endonuclease; or
(ii) an RNA-guided DNA endonuclease is introduced into the microbial host cell along with the editing plasmid;
(b) growing the microbial host cell from step (a) in media selective for microbial host cells expressing the selection marker gene in the editing plasmid, thereby creating an edited microbial host cell;
(c) introducing into the edited microbial host cell of the previous step an additional editing plasmid, an additional gRNA and an additional repair fragment, wherein the additional gRNA comprises sequence complementary to an additional locus in the genome of the edited microbial host cell, wherein the additional repair fragment comprises homology arms separated by a sequence for a genetic edit in or adjacent to the additional locus in the genome of the edited microbial host cell, wherein the homology arms comprise sequence homologous to sequence that flanks the additional locus in the genome of the edited microbial host cell, wherein the additional editing plasmid comprises a selection marker gene that is different from the selection marker gene introduced in the previous introducing step, wherein the additional editing plasmid comprises the same origin of replication as the editing plasmid, and wherein the additional editing plasmid comprises at least one or both of a gene encoding the additional gRNA and the additional repair fragment, thereby iteratively editing the microbial host cell genome; and (d) growing the edited microbial host cell from the previous step in media selective for microbial host cells expressing the selection marker gene in the additional editing plasmid of the previous step, thereby clearing the editing plasmids lacking the selection marker gene in the additional editing plasmid of the previous step from the edited microbial host cell from the previous step; wherein a counterselection is not performed before step (c).

25. The method of claim 24, wherein the microbial host cell is a filamentous fungus.

26. The method of claim 25, wherein the filamentous fungus is *Aspergillus niger*.

27. The method of claim 24, comprising step (e) repeating steps (c) and (d) one or more times for one or more additional rounds of gene editing.

* * * * *